US012577279B2

(12) United States Patent
Brandenburg et al.

(10) Patent No.: US 12,577,279 B2
(45) Date of Patent: Mar. 17, 2026

(54) INFLUENZA VIRUS VACCINES AND USES THEREOF

(71) Applicant: Janssen Vaccines & Prevention B.V., Leiden (NL)

(72) Inventors: Boerries Brandenburg, Utrecht (NL); Johannes Petrus Maria Langedijk, Amsterdam (NL); Tina Ritschel, Oegstgeest (NL); Ferdinand Jacobus Milder, Zwolle (NL); Mandy Antonia Catharina Jongeneelen, Leiden (NL)

(73) Assignee: Janssen Vaccines & Prevention B.V., Leiden (NL)

(*) Notice: Subject to any disclaimer, the term of this patent is extended or adjusted under 35 U.S.C. 154(b) by 917 days.

(21) Appl. No.: 17/754,922

(22) PCT Filed: Oct. 15, 2020

(86) PCT No.: PCT/EP2020/079017
§ 371 (c)(1),
(2) Date: Apr. 15, 2022

(87) PCT Pub. No.: WO2021/074286
PCT Pub. Date: Apr. 22, 2021

(65) Prior Publication Data
US 2023/0312654 A1 Oct. 5, 2023

Related U.S. Application Data

(60) Provisional application No. 62/915,186, filed on Oct. 15, 2019.

(51) Int. Cl.
*A61K 39/00* (2006.01)
*A61K 39/145* (2006.01)
*C07K 14/005* (2006.01)

(52) U.S. Cl.
CPC ............ *C07K 14/005* (2013.01); *A61K 39/00* (2013.01)

(58) Field of Classification Search
CPC .................. C07K 14/005; A61K 39/00; A61K 2039/575; A61K 39/12; A61K 39/145; C12N 2760/16222; C12N 2760/16234; A61P 31/16
See application file for complete search history.

(56) References Cited

FOREIGN PATENT DOCUMENTS

| | | |
|---|---|---|
| EP | 2785372 A | 10/2014 |
| WO | 2013043729 A1 | 3/2013 |
| WO | WO-2019145310 A1 * | 8/2019 ............. A61K 39/12 |

OTHER PUBLICATIONS

Di Lella S, Herrmann A, Mair CM. Modulation of the pH Stability of Influenza Virus Hemagglutinin: A Host Cell Adaptation Strategy. Biophys J. Jun. 7, 2016;110(11):2293-2301. (Year: 2016).*
Byrd-Leotis L, Galloway SE, Agbogu E, Steinhauer DA. Influenza hemagglutinin (HA) stem region mutations that stabilize or desta-bilize the structure of multiple HA subtypes. J Virol. Apr. 2015;89(8):4504-16. (Year: 2015).*
Impagliazzo et al (2016). A stable trimeric influenza hemagglutinin stem as a broadly protective immunogen. Science. Sep. 18, 2015;349(6254):1301-6. (Year: 2015).*
International Search Report issued Apr. 25, 2021 in PCT/EP2020/079017.
Written Opinion issued Apr. 25, 2021 in PCT/EP2020/079017.
Santos, Jefferson J.S., et al., "Development of an Alternative Modi-fied Live Influenza B Virus Vaccine," Journal of Virology, vol. 91, No. 12, May 26, 2017.
International Search Report issued Apr. 25, 2021 in PCT/EP2020/079017, 7 pages.
Written Opinion issued Apr. 25, 2021 in PCT/EP2020/079017, 10 pages.
Santos, Jefferson J.S., et al., "Development of an Alternative Modi-fied Live Influenza B Virus Vaccine," Journal of Virology, vol. 91, No. 12, May 26, 2017, 20 pages.

* cited by examiner

*Primary Examiner* — Janet L Andres
*Assistant Examiner* — Samadhan Jaising Jadhao
(74) *Attorney, Agent, or Firm* — Ice Miller LLP

(57) ABSTRACT

Provided herein are isolated mutant influenza hemagglutinin polypeptides, methods for providing isolated mutant hemag-glutinin polypeptides, compositions comprising the same, vaccines comprising the same and methods of their use, in particular in the detection, prevention and/or treatment of influenza.

39 Claims, 23 Drawing Sheets
Specification includes a Sequence Listing.

| 461 | ID. | CR9114 (%) |
|---|---|---|
| - | UFV170090 | 100 |
| M | UFV171700 | 137 |
| L | UFV171701 | 107 |
| W | UFV171702 | 61 |
| Y | UFV171703 | 90 |
| R | UFV171741 | 281 |

| 227 | 238 | ID. | CR9114 (%) |
|-----|-----|-----|------------|
| - | - | UFV170090 | 100 |
| Q | - | UFV170519 | 145 |
| N | - | UFV170520 | 145 |
| F | - | UFV170521 | 141 |
| I | - | UFV170522 | 128 |
| Y | - | UFV170523 | 136 |
| - | N | UFV170515 | 85 |
| - | Q | UFV170516 | 87 |
| - | I | UFV170517 | 108 |
| - | F | UFV170518 | 102 |
| Q | N | UFV170524 | 124 |
| Q | I | UFV170525 | 245 |

*"-" symbol indicates the WT residue is maintained at the indicated position*

FIG. 2C

| 384 | 476 | ID. | CR9114 (%) |
|---|---|---|---|
| - | - | UFV170090 | 100 |
| W | - | UFV170541 | 21 |
| F | - | UFV170542 | 35 |
| N | - | UFV170543 | 31 |
| Q | - | UFV170544 | 21 |
| I | - | UFV170545 | 24 |
| - | W | UFV170546 | 80 |
| - | F | UFV170547 | 94 |
| - | Y | UFV170548 | 114 |
| - | I | UFV170549 | 72 |
| - | N | UFV170550 | 141 |
| - | Q | UFV170551 | 125 |
| W | W | UFV170552 | 9 |
| W | F | UFV170553 | 12 |
| F | W | UFV170554 | 32 |
| W | Y | UFV170555 | 12 |
| I | I | UFV170556 | 231 |
| N | N | UFV170557 | 35 |
| Q | Q | UFV170558 | 61 |
| N | Q | UFV170559 | 53 |

FIG. 2D

| 227 | 238 | 384 | 476 | Foldon | ID. | Expression (%) | CR9114 (%) | Temperature stability $Tm_{50}$ (°C) |
|---|---|---|---|---|---|---|---|---|
| - | - | - | - | + | UFV170090 | 100 | 100 | 59.5 |
| Q | I | - | - | + | UFV170525 | 88 | 143 | 63.4 |
| - | - | I | I | + | UFV170556 | 139 | 229 | 59.0 |
| - | - | I | I | - | UFV171348 | 244 | 78 | 58.3 |
| Q | I | I | I | - | UFV171387 | 212 | 173 | 64.7 |

*"-" symbol indicates the wild type residue is maintained at the indicated position;*
*"+" symbol indicates a C-terminal Foldon Trimerization is present*

FIG. 2E

| 136 | 137 | 141 | 151 | ID. | Expression (%) | Trimer (%) | CR9114 (%) | CR8071 (%) | SD84 (%) |
|---|---|---|---|---|---|---|---|---|---|
| - | - | - | - | UFV171990 | 100 | 100 | 100 | 100 | 100 |
| + | - | - | - | UFV171993 | 100 | 93 | 96 | 94 | 80 |
| - | - | + | - | UFV171992 | 88 | 92 | 86 | 82 | 75 |
| - | - | - | + | UFV171991 | 92 | 104 | 90 | 86 | 48 |
| - | - | - | - | UFV170090ᶠ | 100 | 100 | 100 | 100 | 100 |
| - | + | - | - | UFV171472ᶠ | 69 | 88 | 119 | 104 | 60 |

*"-" symbol indicates the wild type residue is maintained at the indicated position*
*"+" symbol indicates the presence of N-linked glycan motif at indicated position*
*"F" symbol indicates the presence of a Foldon trimerization domain*

| 175 | 219 | 257 | 258 | ID. | Expression (%) | Trimer (%) | CR9114 (%) | SD84 (%) |
|-----|-----|-----|-----|-----|---------------|-----------|-----------|----------|
| - | - | - | - | UFV171990 | 100 | 100 | 100 | 100 |
| - | F | - | - | UFV172064 | 56 | 42 | 56 | 53 |
| - | W | - | - | UFV172065 | 43 | 32 | 33 | 189 |
| - | Y | - | - | UFV172066 | 55 | 31 | 43 | 63 |
| - | R | - | - | UFV172067 | 25 | 22 | 35 | 49 |
| - | E | - | - | UFV172068 | 27 | 18 | 31 | 44 |
| - | - | - | E | UFV172069 | 34 | 32 | 39 | 45 |
| - | - | - | D | UFV172070 | 29 | 19 | 33 | 41 |
| - | - | - | V | UFV172071 | 45 | 4 | 21 | 18 |
| - | - | - | F | UFV172072 | 11 | 59 | 76 | 82 |
| - | - | E | - | UFV172073 | 75 | 90 | 88 | 17 |
| - | - | D | - | UFV172074 | 55 | 43 | 56 | 27 |
| - | - | V | - | UFV172075 | 70 | 89 | 94 | 579 |
| - | - | F | - | UFV172076 | 36 | 15 | 41 | 30 |
| F | - | - | - | UFV172077 | 62 | 66 | 59 | 78 |
| W | - | - | - | UFV172078 | 74 | 78 | 71 | 56 |
| Y | - | - | - | UFV172079 | 42 | 26 | 36 | 74 |

*"-" symbol indicates the wild type residue is maintained at the indicated position*

FPPR (369-383)

| FPPR 369 ... 383 | ID. | Expression (%) | Trimer (%) | CR9114 (%) | CR8071 (%) | SD84 (%) |
|---|---|---|---|---|---|---|
| AGFLEGGWEGMIAGW | UFV171990 | 100 | 100 | 100 | 100 | 100 |
| AGF-----EGMIAGW | UFV172678 | 103 | 109 | 115 | 97 | 114 |
| AGFL-----GMIAGW | UFV172680 | 83 | 51 | 55 | 67 | 54 |
| AGFLE------IAGW | UFV172681 | 111 | 92 | 90 | 91 | 86 |
| AGF-------MIAGW | UFV172683 | 98 | 55 | 66 | 68 | 43 |
| AGFL----EGMIAGW | UFV172686 | 96 | 100 | 97 | 104 | 167 |
| AGFLE---EGMIAGW | UFV172687 | 102 | 101 | 100 | 102 | 136 |
| AGFLEGG-----AGW | UFV172691 | 110 | 108 | 74 | 97 | 145 |
| AGFLEGGW-----GW | UFV172690 | 107 | 117 | 24 | 101 | 147 |

*"---" symbol indicates the deletion of the respective number of wild type residues at these positions*

‐ ‐ ‐  *Reference polypeptide UFV180284; C-terminally truncated at TM domain (after residue 549).*
———  *Polypeptides with alternative C-terminal truncations.*

FIG. 7A

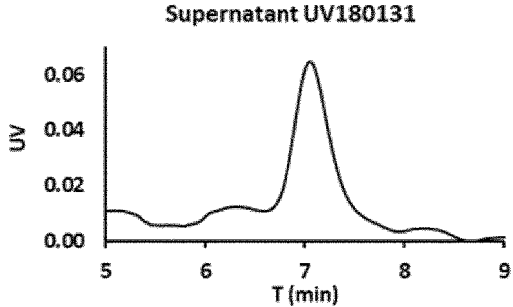
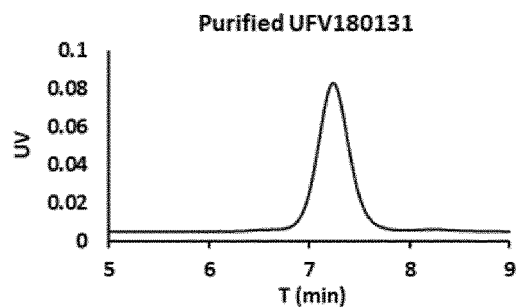

FIG. 7B

| N-linked glycan motif | | | Stabilizing mutations | RBS | FPPR deletion | ID. | Expression (mg/L) | CR9114 $EC_{50}$ (nM) | CR8071 $EC_{50}$ (nM) | SD84 $EC_{50}$ (nM) | Temp. stability $Tm_{50}$ (°C) |
|---|---|---|---|---|---|---|---|---|---|---|---|
| 136 | 141 | 151 | | 257 | | | | | | | |
| - | - | - | - | - | - | UFV170088 | 270 | 0.6 | 0.4 | 12.9 | 59.7 |
| + | + | + | + | E | 372-376 | UFV180131 | 541 | 1.5 | 1.1 | n.b. | 68.3 |
| E | + | + | + | E | 372-376 | UFV180137 | 580 | 1.5 | 1.0 | n.b. | 69.2 |
| E | + | + | + | E | 376-380 | UFV180251 | 605 | 2.6 | 0.8 | n.b. | 69.4 |
| E | + | + | + | E | 376-380 | UFV180284 | 378 | 2.0 | 1.0 | n.b. | 69.3 |

*"+"* indicates presence of an N-linked glycan motif at indicated positions (136, 141, and 151) and the presence of the stabilizing mutations (K277Q, H238I, H384I, A461R, and H476I) as well as the receptor binding site mutation (Q257E).
*"-"* indicates the symbol indicates the wild type residue is maintained at the indicated position.
*"n.b."* indicates no binding was observed.

FIG. 7C

| Parental ID. | C-terminal truncation | Cleavage site knock out | ID. | Expression (mg/L) | CR9114 $EC_{50}$ (nM) | CR8071 $EC_{50}$ (nM) | mAb172498 $EC_{50}$ (nM) | Temp. stability $Tm_{50}$ (°C) |
|---|---|---|---|---|---|---|---|---|
| UFV180131 | 532-585 | R362Q | UFV180846 | 325 | 1.8 | 3.8 | n.b. | 68.3 |
| UFV180137 | 532-585 | R362Q | UFV180847 | 384 | 1.4 | 3.5 | n.b. | 69.3 |
| UFV180251 | 532-585 | R362Q | UFV180848 | 253 | 4.6 | 4.1 | n.b. | 69.3 |
| UFV180284 | 532-585 | R362Q | UFV180849 | 271 | 2.9 | 4.6 | n.b. | 69.2 |

*"n.b."* indicates no binding was observed.

FIG. 7D -cont.
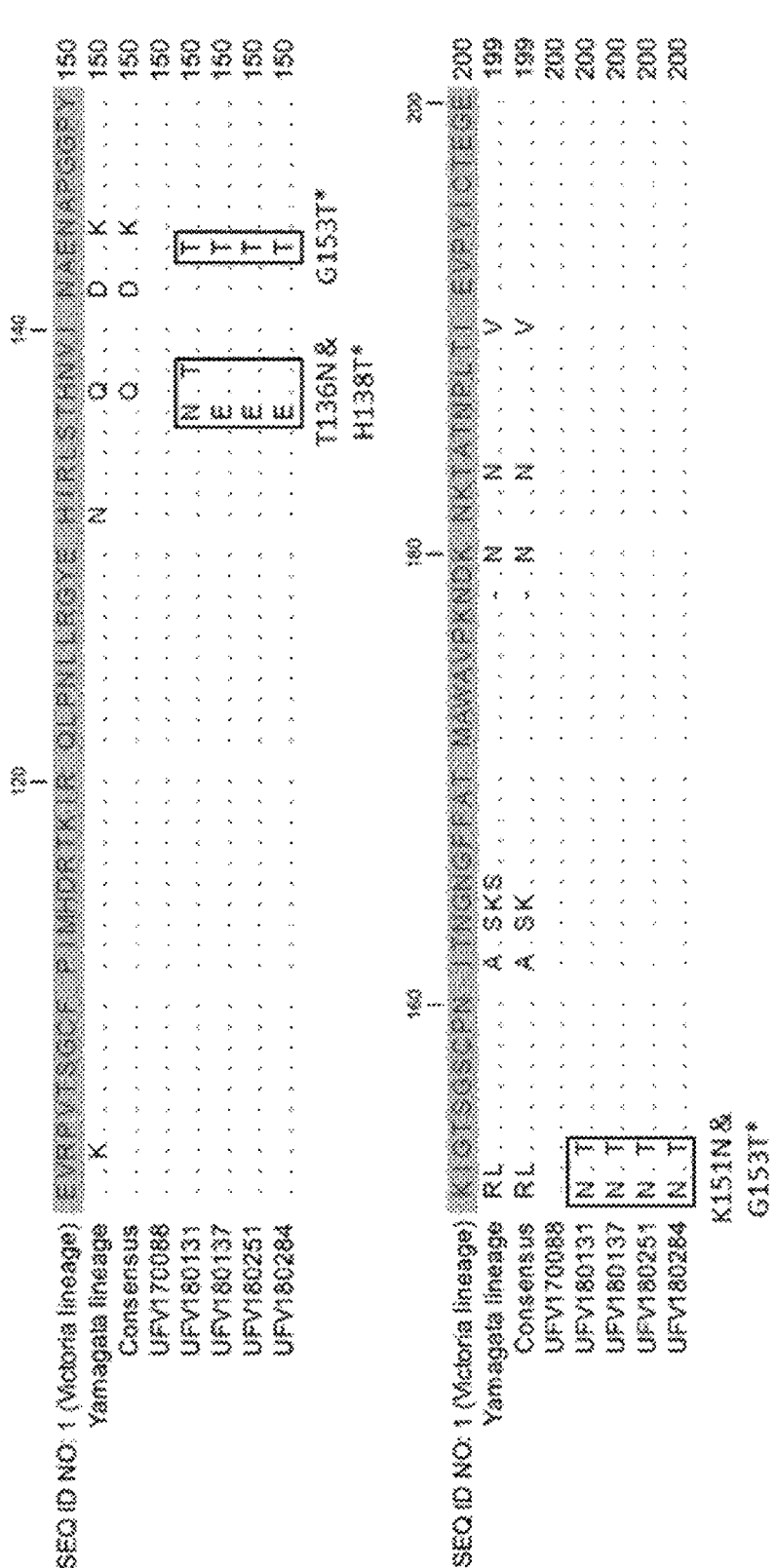

FIG 7D-cont.
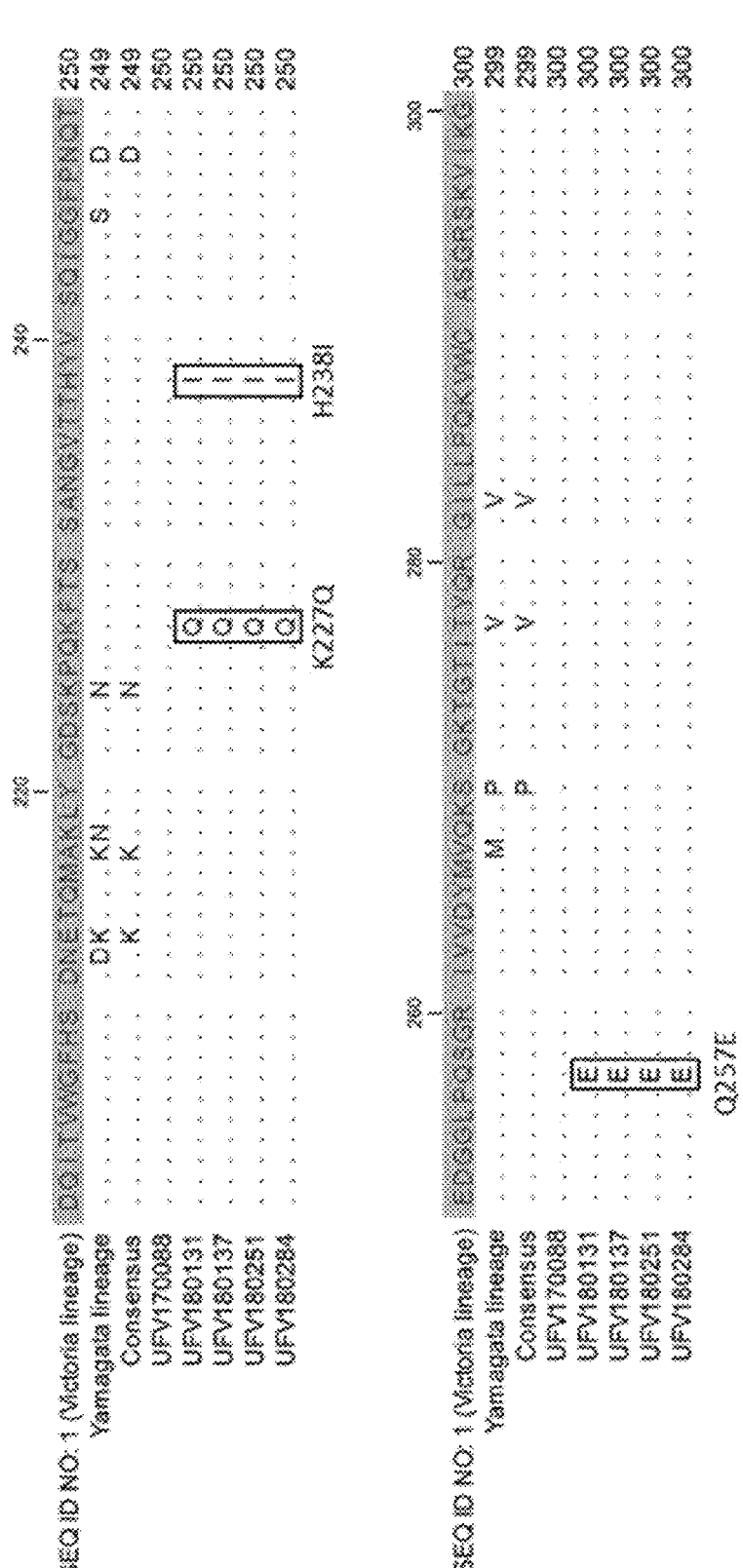

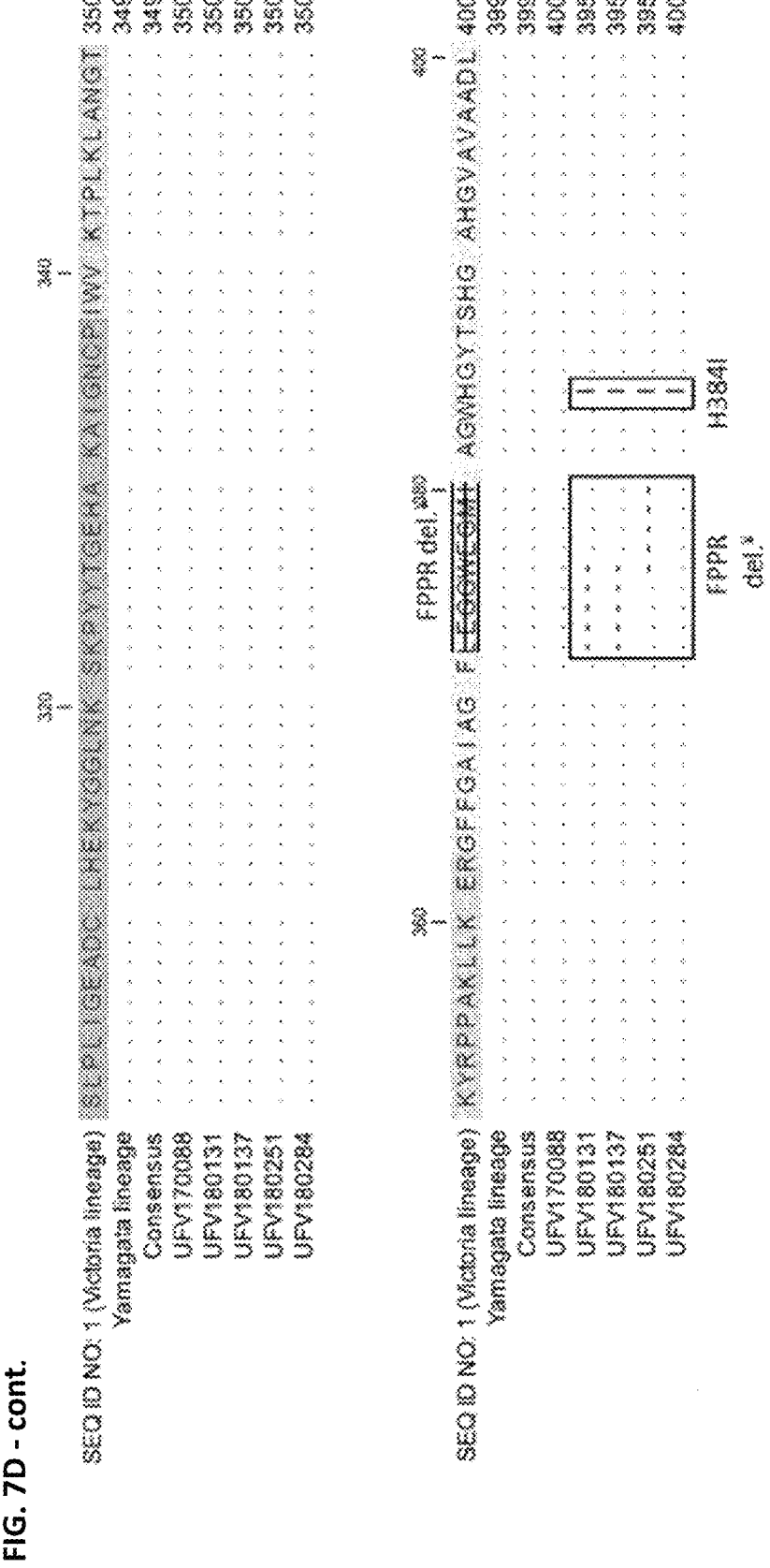
FIG. 7D – cont.

FIG. 7D - cont.
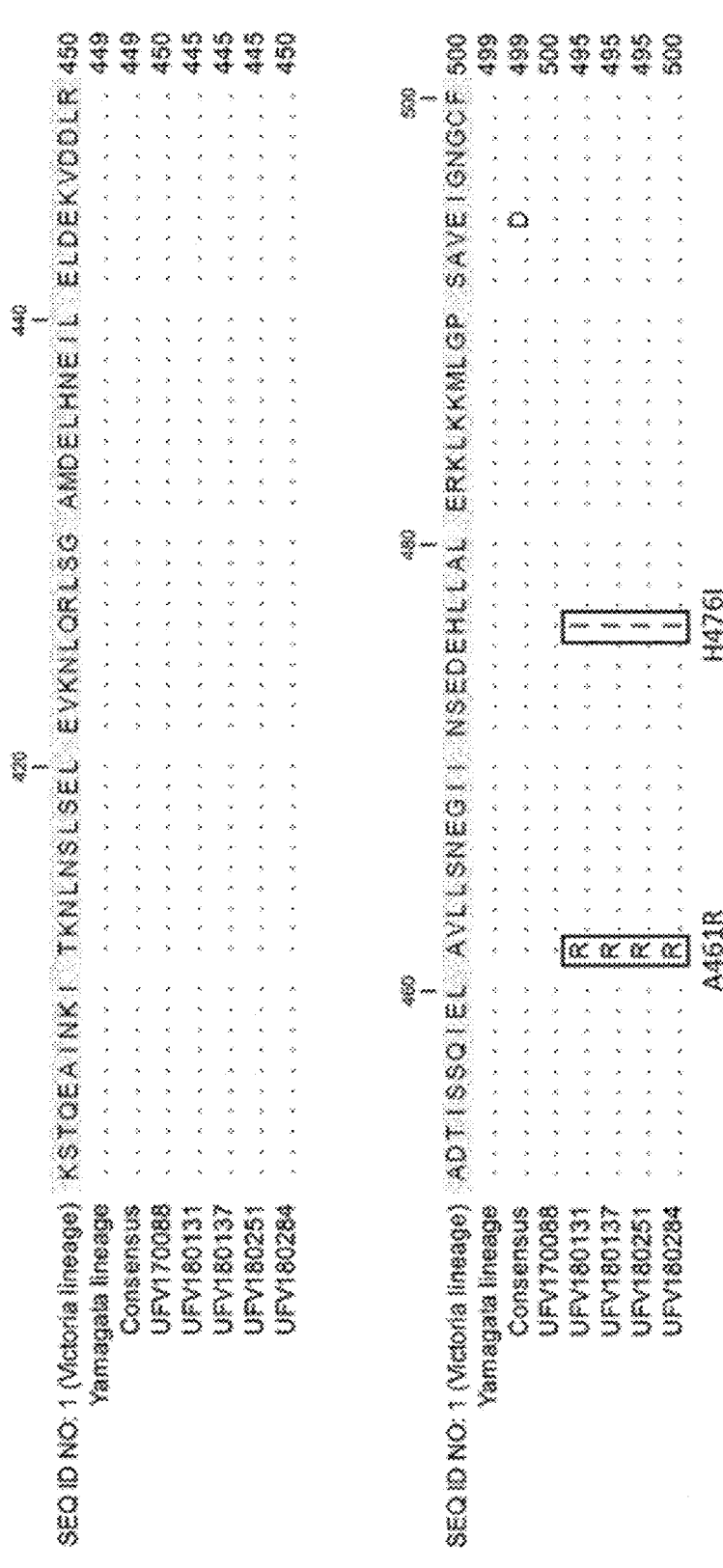

FIG. 7D - cont.
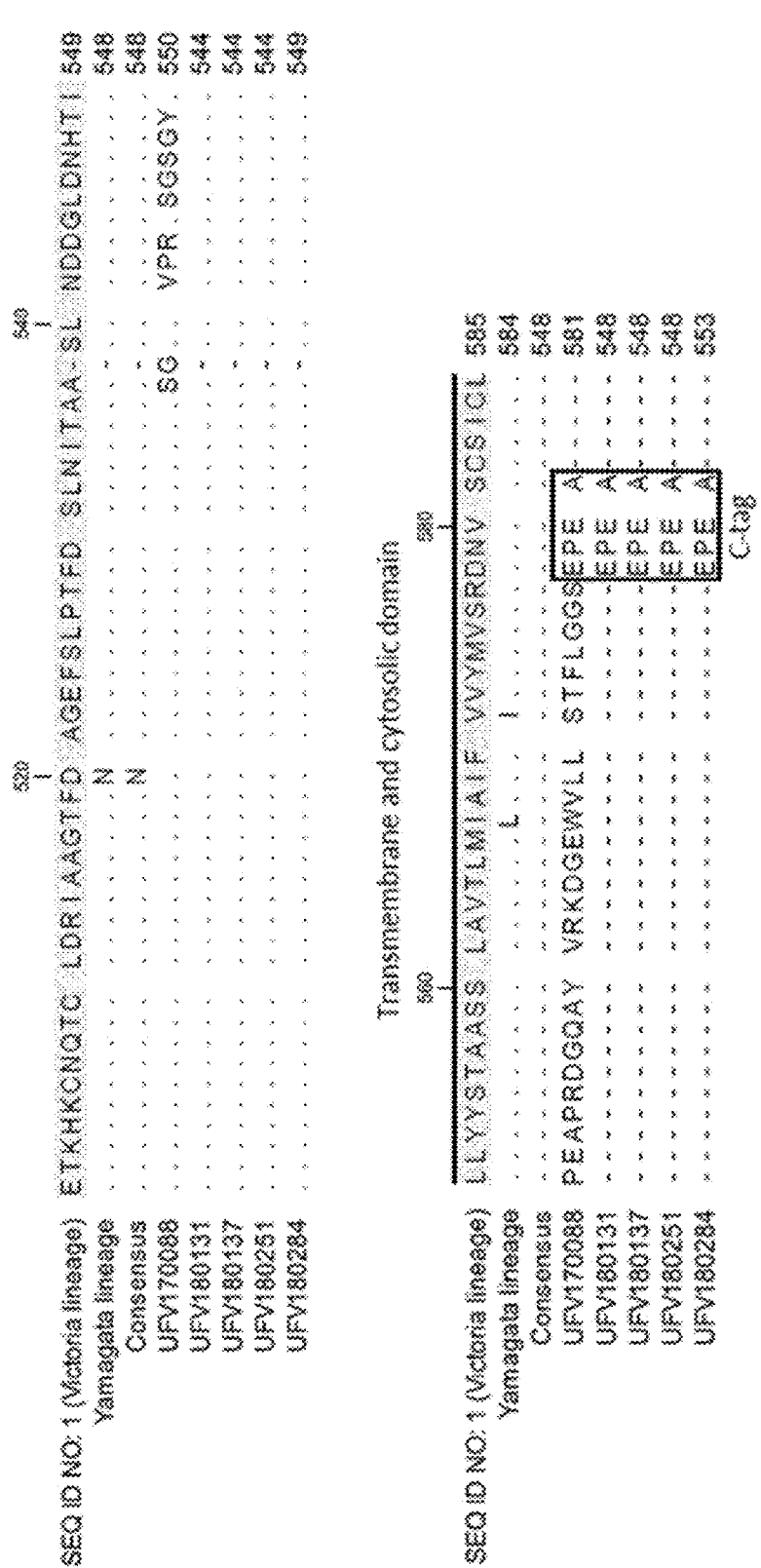

FIG. 7E - cont.
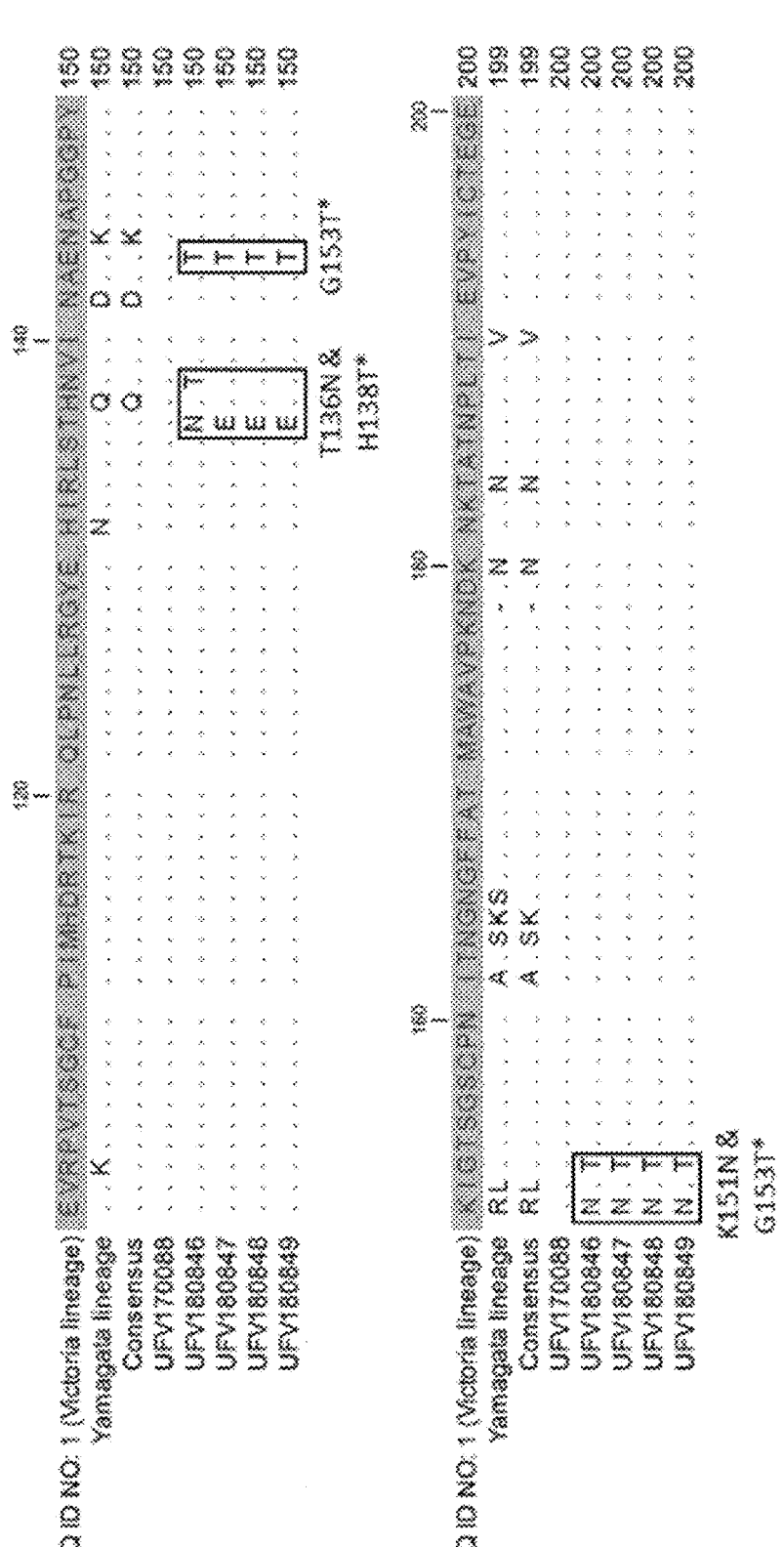

FIG. 7E - cont.
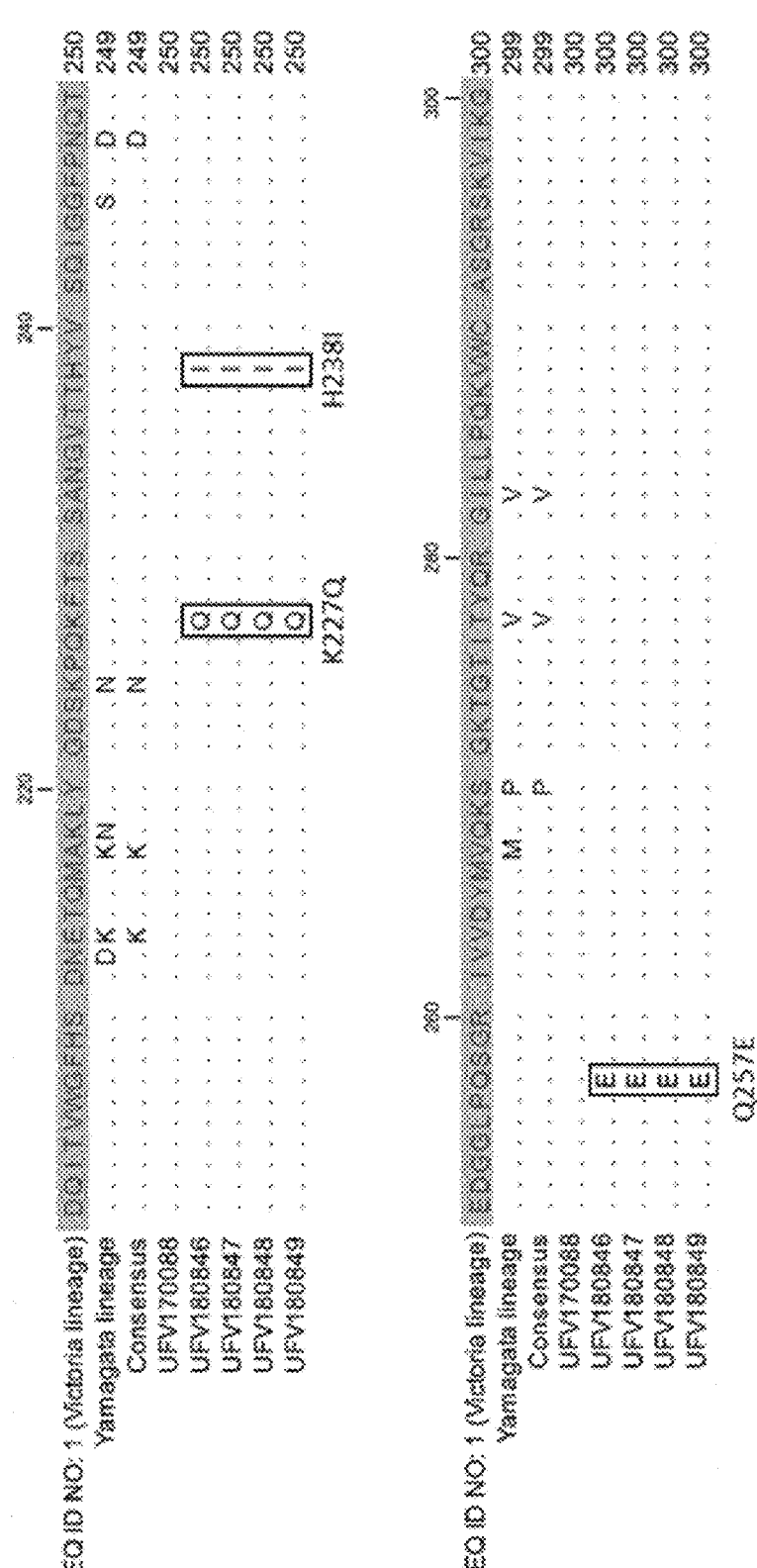

FIG. 7E - cont.
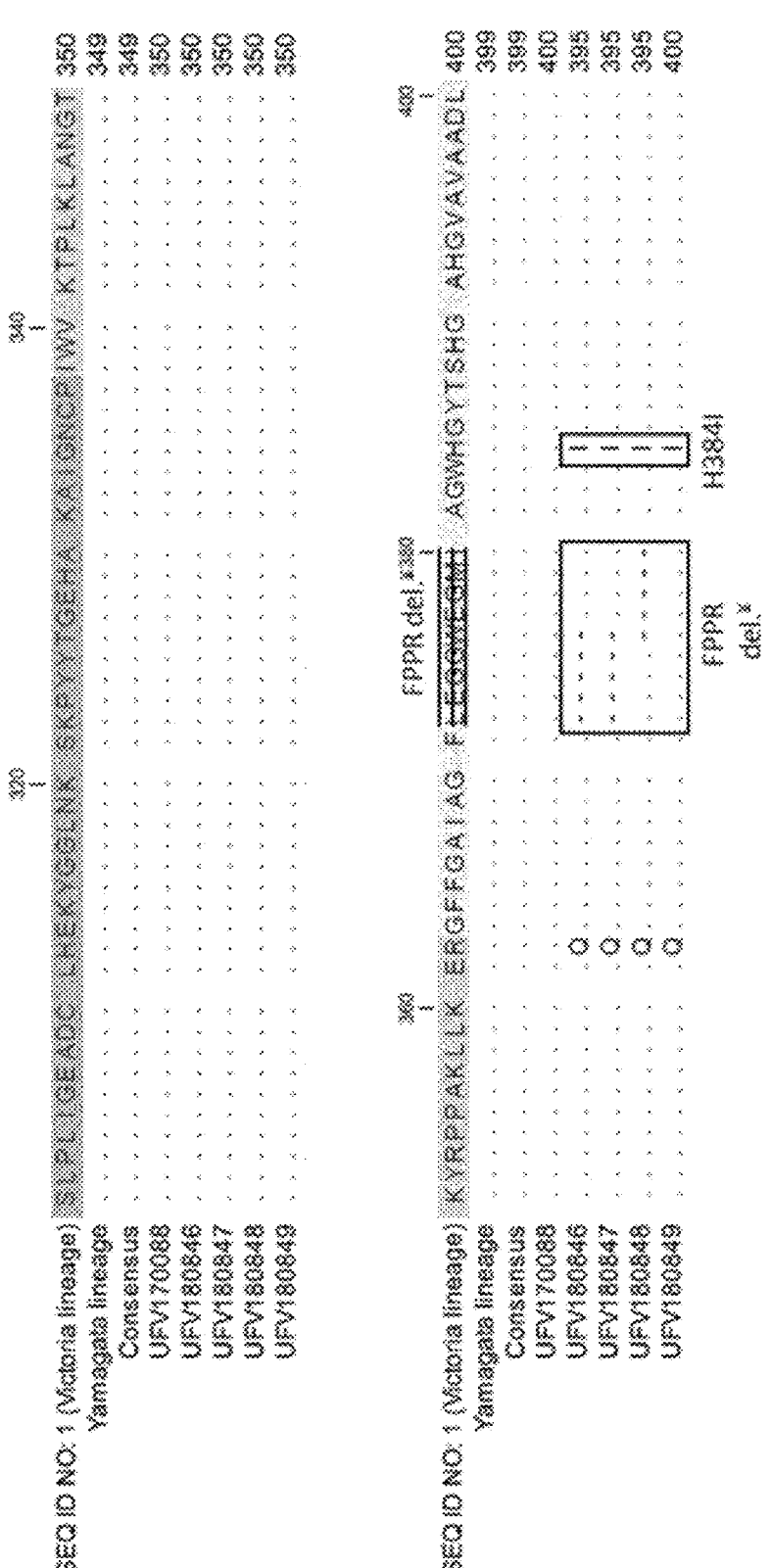

FIG. 7E - cont.
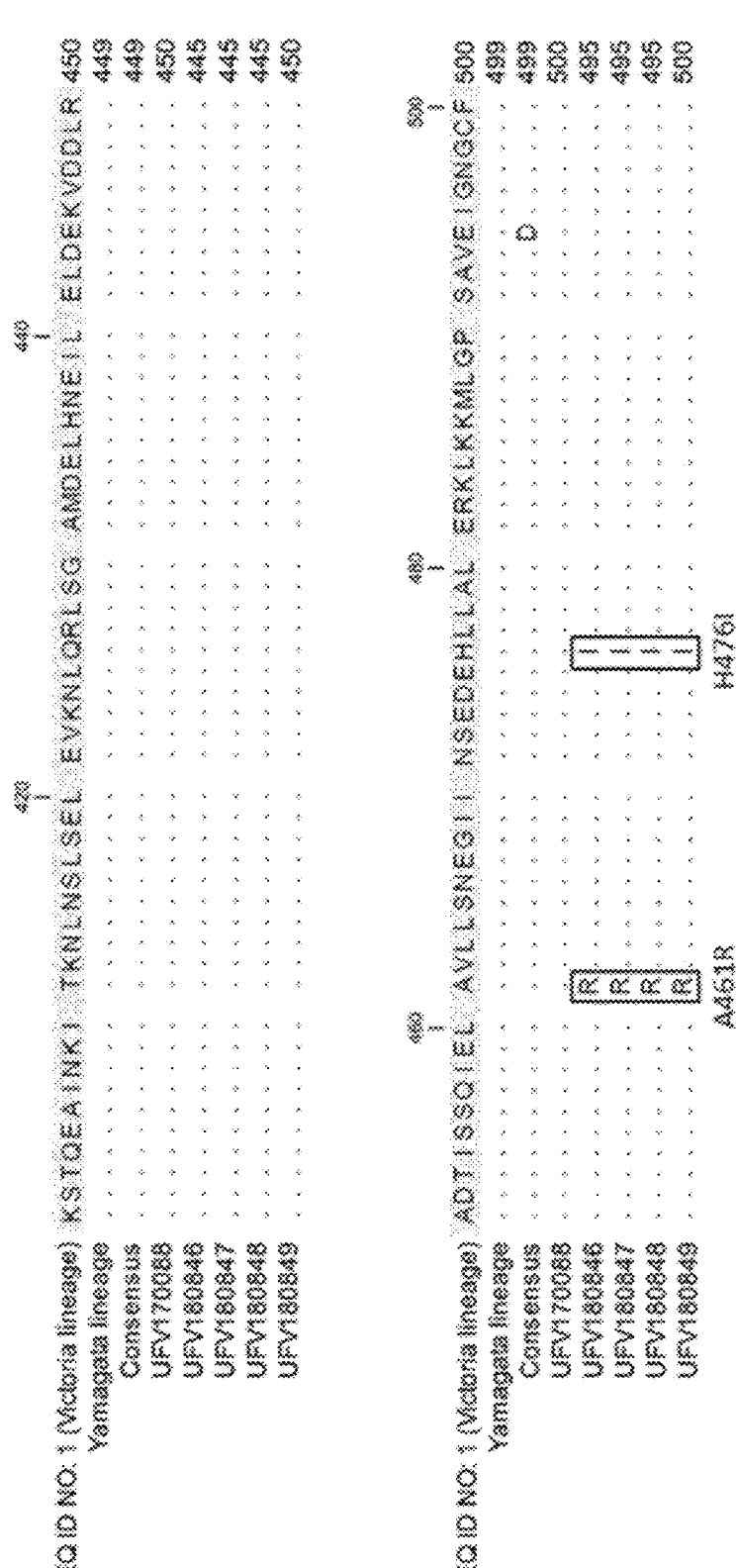

FIG. 7E - cont.
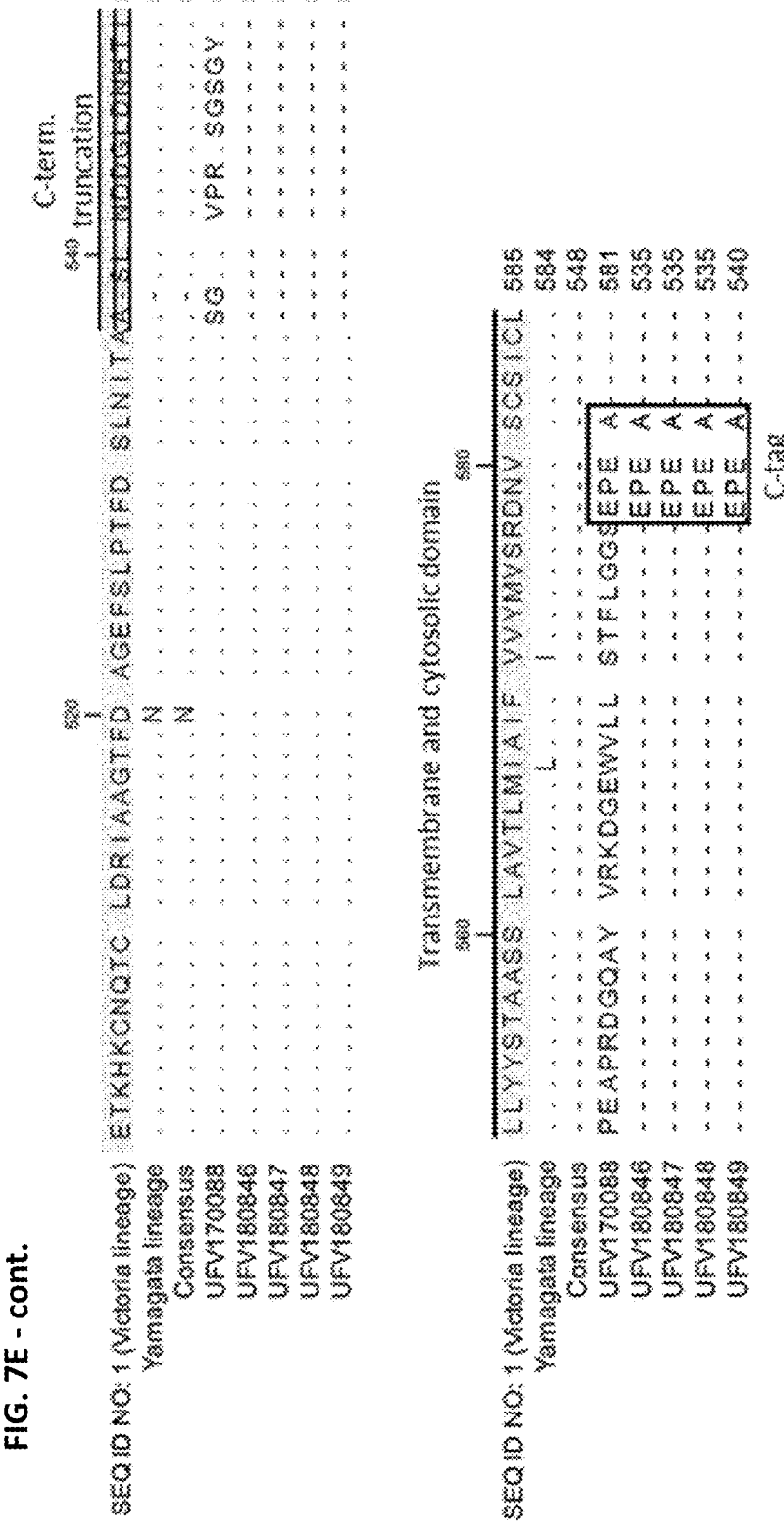

| Strain | Wild type ID. | Expression (mg/mL) | Stabilized[1] ID. | Expression (mg/mL) | Fold increase |
|---|---|---|---|---|---|
| B/Lee/1940 | UFV180567 | 100 | UFV180566[2] | 185 | 1.9 |
| B/Yamagata/16/1988 | UFV180565 | 62 | UFV180400[2] | 170 | 2.7 |
| B/Florida/04/2006 | UFV180571 | 42 | UFV180570[2] | 158 | 3.8 |
| B/Iowa/06/2017 | UFV190909 | 66 | UFV190521 | 106 | 1.6 |

"1"     indicates the presence of stabilizing mutations (K227Q, H238I, H384I, A461R, and H476I)
"2"     indicates the presence of FPPR deletion 372-376.

INFLUENZA VIRUS VACCINES AND USES THEREOF

CROSS-REFERENCE TO RELATED APPLICATION

This application is a Section 371 of International Application No. PCT/EP2020/079017 filed Oct. 15, 2020, which was published in the English language Apr. 22, 2021, under International Publication No. WO 2021/074286 A1, which claims priority to U.S. patent application Ser. No. 62/915, 186 filed Oct. 15, 2019, the disclosures of which are incorporated herein by reference in their entireties.

STATEMENT REGARDING FEDERALLY FUNDED RESEARCH

This invention was made, at least in part, with Government support under Agreement HHSO10020170018C, awarded by HHS. The Government has certain rights in the invention.

INTRODUCTION

The invention relates to the field of medicine. Provided herein are isolated influenza hemagglutinin polypeptides, methods for providing hemagglutinin polypeptides, compositions comprising the same, vaccines comprising the same and methods of their use, in particular in the detection, prevention and/or treatment of influenza.

REFERENCE TO SEQUENCE LISTING SUBMITTED ELECTRONICALLY

This application contains a sequence listing, which is submitted electronically via EFS-Web as an ASCII formatted sequence listing with a file name "688097.562US Sequence Listing" and a creation date of Sep. 16, 2019 and having a size of 468 kb. The sequence listing submitted via EFS-Web is part of the specification and is herein incorporated by reference in its entirety.

BACKGROUND

Influenza A and B viruses are major human pathogens, causing a respiratory disease (commonly referred to as "influenza" or "the flu") that ranges in severity from subclinical infection to primary viral pneumonia which can result in death. The WHO estimates that annual epidemics of influenza result in ~1 billion infections, 3-5 million cases of severe illness and 300,000-500,000 deaths. The severity of pandemic influenza depends on multiple factors, including the virulence of the pandemic virus strain and the level of pre-existing immunity. The most severe influenza pandemic, in 1918, resulted in >40 million deaths worldwide. Influenza vaccines are formulated every year to match the circulating strains, as they evolve antigenically owing to antigenic drift. Nevertheless, vaccine efficacy is not optimal and is dramatically low in the case of an antigenic mismatch between the vaccine and the circulating virus strain. Antiviral agents that target the influenza virus enzyme neuraminidase have been developed for prophylaxis and therapy. However, the use of these antivirals is still limited. Emerging approaches to combat influenza include the development of universal influenza virus vaccines that provide protection against antigenically distant influenza viruses (Krammer et al., Nat. Rev. Disease Primers 4:3 (2018)).

During the last three decades two distinct influenza B lineages have co-circulated in the population to a varying extent each season, and the dominant B lineage in a specific season has proved hard to predict, complicating the decision of which lineage to include in the trivalent vaccine (TIV) (Ambrose et al., Hum. Vaccin. Immunother. 8:81-8 (2012); US Centers for Disease Control and Prevention, "Seasonal influenza activity surveillance reports 2001-2018" www.cdc.gov/flu/weekly/pastreports.htm (accessed on Jul. 2, 2018); European Centre for Disease Prevention and Control/WHO Regional Office for Europe, "Annual epidemiological reports on seasonal influenza 2001-2018," ecdc.europa.eu/en/seasonal-influenza/surveillance-and-disease-data/aer (accessed on Jul. 2, 2018)). The importance of an effective coverage of influenza B by vaccination is demonstrated by its contribution to the overall burden of seasonal influenza. According to data from the US Centers for Disease Control, and reports from several European countries, influenza B was responsible for 0.8-82% of the total laboratory confirmed influenza cases between 2001 and 2018 with a seasonal average of 25% (Ambrose et al., Hum. Vaccin. Immunother. 8:81-8 (2012); US Centers for Disease Control and Prevention, "Seasonal influenza activity surveillance reports 2001-2018" www.cdc.gov/flu/weekly/pastreports.htm (accessed on Jul. 2, 2018); European Centre for Disease Prevention and Control/WHO Regional Office for Europe, "Annual epidemiological reports on seasonal influenza 2001-2018," ecdc.europa.eu/en/seasonal-influenza/surveillance-and-disease-data/aer (accessed on Jul. 2, 2018); Dijkstra et al., Epidemiol. Infect. 137:473-9 (2009); Peltola et al., Clin. Infect. Dis. 36:299-305 (2003)). Moreover, influenza B is a major contributor to the total morbidity and mortality from influenza, with attributable hospitalization rate similar to influenza A/H3N2 and greater than A/H1N1 (Thompson et al., JAMA 292:1333-40 (2004)), accounting for 15% of all influenza attributable respiratory and circulatory-related death in the United States and 34% among paediatric patients (Ambrose et al., Hum. Vaccin. Immunother. 8:81-8 (2012); Thompson et al., JAMA 289:179-86 (2003)). These principles prompted several health authorities, including the World Health Organization and the US Advisory Committee on Immunization Practices, to recommend quadrivalent influenza vaccine (QIV) containing two influenza B antigens (one of each B lineage) as one of the options for seasonal vaccination (Grohskopf et al., MMWR Recomm. Rep. 66:1-20 (2017); Grohskopf et al., MMWR Recomm. Rep. 67:643-5 (2018); World Health Organization, "Recommended composition of influenza virus vaccines for use in the 2017-2018 northern hemisphere influenza season," www.whaint/influenza/vaccines/virus/recommendations/2018_19_north/en (accessed on Jul. 2, 2018)).

The current immunization practice relies on early identification of circulating influenza viruses to allow for timely production of an effective seasonal influenza vaccine. Apart from the inherent difficulties in predicting the strains that will be dominant during the next season, antiviral resistance and immune escape also play a role in failure of current vaccines to prevent morbidity and mortality. In addition to this the possibility of a pandemic caused by a highly virulent viral strain originating from animal reservoirs and reassorted to increase human to human spread, poses a significant and realistic threat to global health.

Influenza type B virus strains are almost exclusively found in humans. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and B/Victoria/2/87 (B/Victoria) lineages (Ferguson et al., 2003). Although the spectrum of disease caused by influenza B viruses is generally milder than that caused by influenza A viruses, severe illness requiring hospitalization is still frequently observed with influenza B infection.

It is known that antibodies that neutralize the influenza virus are primarily directed against hemagglutinin (HA). Hemagglutinin or HA is a trimeric glycoprotein that is anchored to the viral coat and has a dual function: it is responsible for binding to the cell surface receptor sialic acid and, after uptake, it mediates the fusion of the viral and endosomal membrane leading to release of the viral RNA in the cytosol of the cell. HA comprises a large head domain and a smaller stem domain. Attachment to the viral membrane is mediated by a C-terminal anchoring sequence connected to the stem domain. The protein is post-translationally cleaved in a designated loop to yield two polypeptides, HA1 and HA2 (the full sequence is referred to as HA0). The membrane distal head region is mainly derived from HA1 and the membrane proximal stem region primarily from HA2.

The reason that the seasonal influenza vaccine must be updated every year is the large variability of the virus. In the hemagglutinin molecule this variation is particularly manifested in the head domain where antigenic drift and shift have resulted in a large number of different variants. Since this is also the area that is immunodominant, most neutralizing antibodies are directed against this domain and act by interfering with receptor binding. The combination of immunodominance and large variation of the head domain also explains why infection with a particular strain does not lead to immunity to other strains: the antibodies elicited by the first infection only recognize a limited number of strains closely related to the virus of the primary infection.

Thus, there is a need for developing a universal influenza virus vaccine that stimulates the production of a robust, broadly protective response against current and future influenza virus strains (both seasonal and pandemic), in particular, providing protection against the influenza B virus for effective prevention and therapy of influenza.

SUMMARY

Provided herein are isolated mutant influenza hemagglutinin polypeptides, methods for providing the isolated hemagglutinin polypeptides, compositions comprising the same, vaccines comprising the same, and methods of using the compositions and vaccines.

Provided herein are isolated mutant influenza hemagglutinin polypeptides. The isolated mutant influenza hemagglutinin polypeptides comprise at least two stabilizing mutations in the polypeptide, wherein the stabilizing mutations comprise substitution mutations at (a) amino acid positions 227 and/or 238; and/or (b) amino acid positions 384 and/or 476, wherein the amino acid position corresponds to the amino acid position of SEQ ID NO:1. In certain embodiments, (a) amino acid position 227 is substituted with an amino acid selected from the group consisting of Q, N, F, I, and Y, and/or amino acid position 238 is substituted with an amino acid selected from the group consisting of N, Q, I, and F; and/or (b) amino acid position 384 is substituted with an amino acid selected from the group consisting of W, F, N, Q, and I, and/or amino acid position 476 is substituted with an amino acid selected from the group consisting of W, F, Y, I, N, and Q. In certain embodiments, (a) amino acid position 227 is substituted with a Q and amino acid position 238 is substituted with an I; and/or (b) amino acid position 384 is substituted with an I and amino acid position 476 is substituted with an I. In certain embodiments, the isolated mutant influenza hemagglutinin polypeptide further comprises one additional stabilizing mutation in the polypeptide. The additional stabilizing mutation is a substitution at amino acid position 461, wherein the amino acid position corresponds to the amino acid position in SEQ ID NO:1. In certain embodiments, amino acid position 461 is substituted with an amino acid selected from the group consisting of M, L, W, Y, and R. In certain embodiments, amino acid position 461 is substituted with an R. The isolated mutant influenza hemagglutinin polypeptide can, for example, comprise an amino acid sequence selected from SEQ ID NO:19, SEQ ID NO:35, SEQ ID NO:39 or SEQ ID NO:40. The isolated mutant influenza hemagglutinin polypeptide can, for example, comprise an amino acid sequence of SEQ ID NO:8.

In certain embodiments, the isolated mutant influenza hemagglutinin polypeptide further comprises at least one additional glycan motif in a head domain of the polypeptide. The glycan motif can, for example, comprise a substitution of an amino (N)-linked glycosylation motif in at least one amino acid position selected from the group consisting of (a) 136 or 137, (b) 141, and (c) 151, wherein the amino acid position corresponds to the amino acid position of SEQ ID NO:1. The glycan motif can, for example, comprise a substitution of the N-linked glycosylation motif at amino acid positions 136 and 141, 136 and 151, 137 and 141, 137 and 151, or 141 and 151. In certain embodiments, the glycan motif comprises the substitution of the N-linked glycosylation motif at amino acid positions 141 and 151. In certain embodiments, the mutant influenza hemagglutinin polypeptide comprises an amino acid sequence selected from SEQ ID NO:42, SEQ ID NO:43, SEQ ID NO:44, or SEQ ID NO:45.

In certain embodiments, the isolated mutant influenza hemagglutinin polypeptide further comprises or solely comprises a receptor binding site mutation in the polypeptide. The receptor binding site mutation can, for example, comprise a substitution at an amino acid position selected from the group consisting of (a) 175, (b) 219, (c) 257, and (d) 258, wherein the amino acid position corresponds to the amino acid position of SEQ ID NO:1. In certain embodiments, (a) 175 is substituted with an amino acid selected from the group consisting of F, W, and Y; (b) 219 is substituted with an amino acid selected from the group consisting of F, W, Y, R, and E; (c) 257 is substituted with an amino acid selected from the group consisting of E, D, V, F; or (d) 258 is substituted with an amino acid selected from the group consisting of E, D, V, and F. In certain embodiments, (a) 175 is substituted with a W, (b) 219 is substituted with an E, (c) 257 is substituted with an E, or (d) 258 is substituted with an E. In certain embodiments, the mutant influenza hemagglutinin polypeptide comprises an amino acid sequence selected from SEQ ID NO:50, SEQ ID NO:51, SEQ ID NO:55, or SEQ ID NO:61.

In certain embodiments, the isolated mutant influenza hemagglutinin polypeptide further comprises an amino acid substitution at position 136, wherein the amino acid position corresponds to the amino acid position of SEQ ID NO:1.

In certain embodiments, the isolated mutant influenza hemagglutinin polypeptide, further comprises or solely comprises a fusion peptide proximal region (FPPR) deletion mutation. The FPPR deletion mutation can, for example, comprise a deletion of at least three to seven amino acid residues between amino acid position 369 and 382, wherein the amino acid position corresponds to the amino acid position of SEQ ID NO:1. The FPPR deletion mutation can, for example, comprise a deletion selected from the group consisting of Δ372-376, Δ372-378, Δ373-377, Δ373-376, Δ374-379, Δ374-376, Δ376-380, and Δ377-381. In certain embodiments, the FPPR deletion mutation is a deletion selected from Δ372-376 or Δ376-380. In certain embodiments, the mutant influenza hemagglutinin polypeptide comprises an amino acid sequence selected from SEQ ID NO:62 or SEQ ID NO:68.

In certain embodiments, the isolated mutant influenza hemagglutinin polypeptide comprises an amino acid sequence selected from SEQ ID NO:70, SEQ ID NO:81, SEQ ID NO:82, SEQ ID NO:83, or SEQ ID NO:84.

In certain embodiments, the isolated mutant influenza hemagglutinin polypeptide can comprise a foldon domain. In certain embodiments, the isolated mutant influenza hemagglutinin polypeptide further comprises a carboxy (C)-terminal truncation starting at an amino acid position from amino acid 532 to amino acid position 549, wherein the amino acid positon corresponds to the amino acid position of SEQ ID NO:1. In certain embodiments, the C-terminal truncation starts at amino acid position 532, 534, 536, 539, 541, 543, 545, 547, or 549, wherein the amino acid position corresponds to the amino acid position of SEQ ID NO:1.

In certain embodiments, the mutant influenza hemagglutinin polypeptide further comprises an amino acid substitution at a cleavage site at amino acid position 362, wherein wherein the amino acid position corresponds to the amino acid position of SEQ ID NO:1. The cleavage site substitution at amino acid position 362 can, for example, be a Q.

Also provided is an isolated nucleic acid encoding an isolated mutant influenza hemagglutinin polypeptide described herein.

Also provided is a vector comprising an isolated nucleic acid described herein.

Also provided is a host cell comprising a vector described herein.

Also provided is a pharmaceutical composition comprising an isolated mutant influenza hemagglutinin polypeptide, an isolated mutant influenza hemagglutinin nucleic acid, and/or a vector described herein and a pharmaceutically acceptable carrier.

Also provided are methods of inducing an immune response against an influenza virus in a subject in need thereof. The methods comprise administering to the subject in need thereof a pharmaceutical composition described herein.

Also provided are methods of producing an isolated mutant influenza hemagglutinin polypeptide. The methods comprise culturing a host cell described herein under conditions capable of producing the mutant influenza hemagglutinin polypeptide and recovering the mutant influenza hemagglutinin polypeptide from the cell or culture.

Also provided are methods of producing a pharmaceutical composition described herein. The methods comprise combining the isolated mutant influenza polypeptide with a pharmaceutically acceptable carrier.

The various embodiments and uses of the polypeptides according to the invention will become clear from the following detailed description of the invention.

BRIEF DESCRIPTION OF THE FIGURES

FIG. 1A shows the threedimensional representation of the polypeptides of the invention (representing the ectodomain of influenza B HA; pdb ID 4NRJ, Ni et al., Virology 450-451:71-83 (2014)). FIG. 1B shows a schematic drawing of a certain polypeptide of the invention UFV180846 (SEQ ID NO:2) with the positions of the substitutions indicated; * introduction of N-linked glycosylation motifs, ¥ fusion peptide proximal region (FPPR) deletion: residues 372-376 are omitted, φ C-terminus truncated in this example after residue 536 (numbering refers to WT HA; SEQ ID NO:1).

FIGS. 2A-2F show the analysis of EXPI-293 expressed polypeptides with stabilizing mutations, normalized to reference wild type FL HA B/Brisbane/60/08 containing a Foldon trimerization domain (UFV170090) (SEQ ID NO:3). FIG. 2A shows a schematic representation of the monomeric HA ectodomain with the positions of the amino acid substitutions indicated in spheres. Specified are the residues as present in wild type (WT) HA. FIG. 2B shows AlphaLISA binding of monoclonal antibody CR9114 to polypeptides of the invention carrying various amino acid substitutions at position 461. Binding is shown as a relative % of respective reference HA sequence. FIG. 2C shows AlphaLISA binding of monoclonal antibody CR9114 to polypeptides of the invention carrying various amino acid substitutions at positions 227 and 236. Binding is shown as a relative % of respective reference HA sequence. FIG. 2D shows AlphaLISA binding of monoclonal antibody CR9114 to polypeptides of the invention carrying various amino acid substitutions at positions 384 and 476. Binding is shown as a relative % of respective reference HA sequence. FIG. 2E shows the expression level and CR9114 binding as determined by AlphaLISA and temperature stability as determined by DSF of polypeptides with combinations of stabilizing substitutions. Binding is shown as a relative % of respective reference HA sequence. FIG. 2F shows SEC profiles of polypeptides; dotted line representing the WT HA (UFV170090) including Foldon trimerization domain. The black lines representing stabilized polypeptides with (UFV170525 (SEQ ID NO:19), and UFV170556 (SEQ ID NO:35)) and without (UFV171348 (SEQ ID NO:39) and UFV171387 (SEQ ID NO:40)) a foldon trimerization domain. The '–' symbol as present in FIGS. 2B, 2C, 2D, and 2E indicates WT residues are present at position indicated in the column header. In FIG. 2E, the '+' and '–' symbol in the Foldon column indicate the presence or absence of the C-terminal foldon trimerization domain, respectively.

FIG. 3A shows a schematic representation of the wild type monomeric HA with the positions of the point substitutions indicated in spheres. FIG. 3B shows the protein expression levels, trimer content, and antibody binding as determined by AlphaLISA. Values are normalized to reference polypeptide UFV171990 (SEQ ID NO:41) for UFV171991 (SEQ ID NO:45), UFV171992 (SEQ ID NO:44), and UFV171993 (SEQ ID NO:42); and reference polypeptide UFV170090 (SEQ ID NO:3) for UFV171472 (SEQ ID NO:42). The '+' symbol indicates the presence of an N-linked glycosylation motif at the particular position. Symbol F indicates the presence of Foldon trimerization domain.

FIG. 4A shows a schematic representation of monomeric HA with positions of the point substitutions indicated in spheres. FIG. 4B shows the protein expression levels, trimer content, and antibody binding as determined by AlphaLISA. Values are normalized to reference polypeptide UFV171990 (SEQ ID NO:41). The '−' symbol indicates the particular position is not mutated and the WT residue is present.

FIG. 5A shows a schematic representation of the monomeric ectodomain of HA with the area of the deleted position in the FPPR indicated in black spheres. FIG. 5B shows the protein expression levels, trimer content, and antibody binding as determined by AlphaLISA. Values are normalized to reference polypeptide UFV171990 (SEQ ID NO:41).

FIGS. 7A-7E show the analysis of EXPI-CHO culture supernatant expressing soluble polypeptides and in vitro characterization of purified polypeptides. Various combinations of substitutions were evaluated; amino (N)-linked glycan motifs in the head domain, stabilizing substitutions, receptor binding site substitution 257E and FPPR deletions. FIG. 7A shows SEC profiles of supernatant of cells expressing UFV180131 (SEQ ID NO:81) (left panel) and of purified UFV180131 (SEQ ID NO:81) (right panel). FIG. 7B shows the expression level of polypeptides as determine by OCTET. $EC_{50}$ values of stem (CR9114), neck (CR8071), and head domain (SD84) specific antibodies to purified HA as determined by ELISA. Temperature stability of purified polypeptides by Differential Scanning Fluorimetry. The '−' symbol indicates that a particular position is not mutated and the WT residue is present. FIG. 7C shows the protein expression levels of construct UFV180846 (SEQ ID NO:84) expressed in EXPI-CHO culture supernatants as determined by OCTET, $EC_{50}$ values of stem (CR9114), neck (CR8071), and head domain (34B5 (WO2015/148806)) specific antibodies to purified HA as determined by ELISA, and temperature stability of the purified polypeptide by Differential Scanning Fluorimetry. FIG. 7D shows an alignment of the Victoria lineage (SEQ ID NO:1), the Yamagata lineage (SEQ ID NO:94), the consensus sequence (SEQ ID NO:95), UFV170088 (SEQ ID NO:80), UFV180131 (SEQ ID NO:81), UFV180137 (SEQ ID NO:82), UFV180251 (SEQ ID NO:83), and UFV180284 (SEQ ID NO:). FIG. 7E shows an alignment of the Victoria lineage (SEQ ID NO:1), the Yamagata lineage (SEQ ID NO:94), the consensus sequence (SEQ ID NO:95), UFV170088 (SEQ ID NO:80), UFV180846 (SEQ ID NO:84), UFV180847 (SEQ ID NO:91); UFV180848 (SEQ ID NO:92), and UFV180849 (SEQ ID NO:93).

DEFINITIONS

Figure 1A:
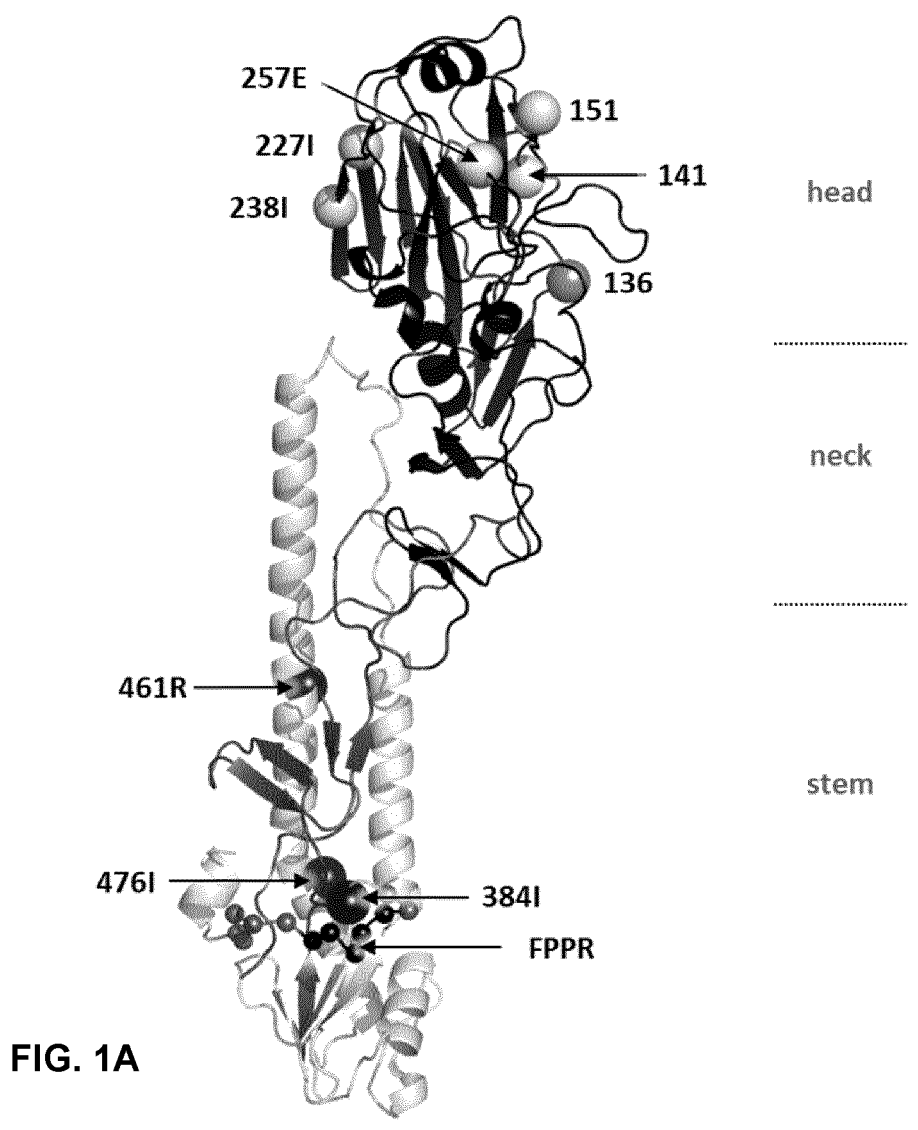
FIGS. 1A-1B show the structure and design elements of the polypeptides of the invention.

Definitions of terms as used in the present invention are given below.

An amino acid according to the invention can be any of the twenty naturally occurring (or 'standard' amino acids) or variants thereof, such as e.g. D-proline (the D-enantiomer of proline), or any variants that are not naturally found in proteins, such as e.g. norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 1 shows the abbreviations and properties of the standard amino acids.

The term "amino acid sequence identity" refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, are determined using sequence alignment techniques well-known in the art, such as by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, 'GAP' (Devereux et al. (1984)).

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (e.g. Met, Ala, Val, Leu), neutral hydrophilic (e.g. Cys, Ser, Thr), acidic (e.g. Asp, Glu), basic (e.g. Asn, Gln, His, Lys, Arg), conformation disrupters (e.g. Gly, Pro) and aromatic (e.g. Trp, Tyr, Phe).

As used herein, the terms "disease" and "disorder" are used interchangeably to refer to a condition in a subject. In some embodiments, the condition is a viral infection, in particular an influenza virus infection. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve a reduction or amelioration of the severity of an influenza virus infection, disease or symptom associated therewith, such as, but not limited to a reduction in the duration of an influenza virus infection, disease or symptom associated therewith, the prevention of the progression of an influenza virus infection, disease or symptom associated therewith, the prevention of the development or onset or recurrence of an influenza virus infection, disease or symptom associated therewith, the prevention or reduction of the spread of an influenza virus from one subject to another subject, the reduction of hospitalization of a subject and/or hospitalization length, an increase of the survival of a subject with an influenza virus infection or disease associated therewith, elimination of an influenza virus infection or disease associated therewith, inhibition or reduction of influenza virus replication, reduction of influenza virus titer; and/or enhancement and/or improvement of the prophylactic or therapeutic effect(s) of another therapy. In certain embodiments, the effective amount does not result in complete protection from an influenza virus disease but results in a lower titer or reduced number of influenza viruses compared to an untreated subject. Benefits of a reduction in the titer, number or total burden of influenza virus include, but are not limited to, less severe symptoms of the infection, fewer symptoms of the infection and a reduction in the length of the disease associated with the infection.

The term "host," as used herein, is intended to refer to an organism or a cell into which a vector such as a cloning vector or an expression vector has been introduced. The organism or cell can be prokaryotic or eukaryotic. Preferably, the host comprises isolated host cells, e.g. host cells in culture. The term "host cells" merely signifies that the cells are modified for the (over)-expression of the polypeptides of the invention. It should be understood that the term host is intended to refer not only to the particular subject organism or cell but to the progeny of such an organism or cell as well. Because certain modifications can occur in succeeding generations due to either mutation or environmental influences, such progeny may not, in fact, be identical to the parent organism or cell, but are still included within the scope of the term "host" as used herein.

The term "included" or "including" as used herein is deemed to be followed by the words "without limitation."

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection can also be a latent infection, i.e., one in which the virus is not replicating. In certain embodiments, an infection refers to the pathological state resulting from the presence of the virus in a cell or a subject, or by the invasion of a cell or subject by the virus.

Influenza viruses are classified into influenza virus types: genus A, B and C. The term "subtype" specifically includes all individual "strains," within each subtype, which usually result from mutations and show different pathogenic profiles, including natural isolates as well as man-made mutants or reassortants and the like. Such strains can also be referred to as various "isolates" of a viral subtype. Accordingly, as used herein, the terms "strains" and "isolates" can be used interchangeably. The current nomenclature for human influenza virus strains or isolates includes the type (genus) of virus, i.e. A, B or C, the geographical location of the first isolation, strain number and year of isolation.

As used herein, the term "influenza virus disease" refers to the pathological state resulting from the presence of an influenza virus, e.g. an influenza A or B virus in a cell or subject or the invasion of a cell or subject by an influenza virus. In specific embodiments, the term refers to a respiratory illness caused by an influenza virus.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. The nucleic acid molecules can be modified chemically or biochemically or can contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

As used herein, in certain embodiments the numbering of the amino acids in hemagglutinin is based on the numbering of amino acids in hemagglutinin of a wild type influenza virus, e.g. the numbering of the amino acids of the influenza strain B/Brisbane/60/08 (SEQ ID NO: 1). As used in the present invention, the wording "amino acid position "x" thus means the amino acid corresponding to the amino acid at position x in hemagglutinin of the particular wild type influenza virus, e.g. B/Brisbane/60/08 (SEQ ID NO: 1). It will be understood by the skilled person that equivalent amino acids in other influenza virus strains and/or subtypes can be determined by multiple sequence alignment. Note that, in the numbering system used throughout this application 1 refers to the N-terminal amino acid of an immature hemagglutinin protein (SEQ ID NO: 1). The mature sequence starts e.g. on position 16 of SEQ ID NO: 1. It will be understood by the skilled person that the leader sequence (or signal sequence) that directs transport of a protein during production (e.g. corresponding to amino acids 1-15 of SEQ ID NO: 1), generally is not present in the final polypeptide, that is e.g. used in a vaccine. In certain embodiments, the polypeptides according to the invention thus comprise an amino acid sequence without the leader sequence, i.e. the amino acid sequence is based on the amino acid sequence of hemagglutinin without the signal sequence.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked and O-linked glycosylation), protease cleavage and lipid modification (e.g. S-palmitoylation).

The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

As used herein, the term "wild-type" in the context of a virus refers to influenza viruses that are prevalent, circulating naturally and producing typical outbreaks of disease.

As used herein, the term "glycan motif" or "N-linked glycosylation motif" refers to a specific amino acid motif of a polypeptide, such that the specific amino acid motif can be glycosylated through the addition of a glycan molecule. An N-linked glycosylation motif comprises the specific amino acid motif of NxT/S (wherein x is not a P). In a polypeptide, wherein an N-linked glycosylation motif or glycan motif is substituted, the amino acid position listed correlates with the asparagine of the NxT/S amino acid motif. By way of an example, in the polypeptides described below, for positions 136, 137, and 151 an N and T were introduced into the polypeptide, with the N being introduced at position 136, 137, and 151 with a threonine being introduced at positions 138, 139, and 153, respectively, whereas for position 141, an asparagine (N) was present in the wild type sequence, and the motif was completed by introducing a threonine at position 143.

DETAILED DESCRIPTION

Influenza viruses have a significant impact on global public health, causing millions of cases of severe illness each year, thousands of deaths, and considerable economic losses. Current trivalent and quadrivalent influenza vaccines elicit a potent neutralizing antibody response to the vaccine strains and closely related isolates, but rarely extend to more diverged strains within a subtype or to other subtypes. In addition, selection of the appropriate vaccine strains presents many challenges and frequently results in sub-optimal protection. Furthermore, predicting the subtype of the next pandemic virus, including when and where it will arise, is currently impossible.

Hemagglutinin (HA) is the major envelope glycoprotein from influenza viruses which is the major target of neutralizing antibodies. Hemagglutinin has two main functions during the entry process. First, hemagglutinin mediates attachment of the virus to the surface of target cells through interactions with sialic acid receptors. Second, after endocytosis of the virus, hemagglutinin subsequently triggers the fusion of the viral and endosomal membranes to release its genome into the cytoplasm of the target cell. HA comprises a large ectodomain of ~500 amino acids that is cleaved by host-derived enzymes to generate 2 polypeptides that remain linked by a disulfide bond. The majority of the N-terminal fragment (HAL 320-330 amino acids) forms a membrane-distal globular domain that contains the receptor-binding site and most determinants recognized by virus-neutralizing antibodies. The smaller C-terminal portion (HA2, ~180 amino acids) forms a stem-like structure that anchors the globular domain to the cellular or viral membrane. The degree of sequence homology between HA1 polypeptides is less than the degress of sequence homology between HA2 polypeptides. The most conserved region is the sequence around the cleavage site, particularly the HA2 N-terminal amino acids, which is conserved among all influenza A and B virus subtypes. Part of this region is exposed as a surface loop in the HA precursor molecule (HA0) but becomes inaccessible when HA0 is cleaved into HA1 and HA2 (Lorieau et al., Proc. Natl. Acad. Aci. USA 107:11341 (2010)).

Most neutralizing antibodies bind to the loops that surround the receptor binding site and interfere with receptor binding and attachment. Since these loops are highly variable, most antibodies targeting these regions are strain-specific, explaining why current vaccines elicit such limited, strain-specific immunity. Recently, however, fully human monoclonal antibodies against influenza virus hemagglutinin with broad cross-neutralizing potency were generated. Functional and structural analysis have revealed that these antibodies interfere with the membrane fusion process and are directed against highly conserved epitopes in the stem domain of the influenza HA protein (Throsby et al., 2008; Ekiert et al. 2009, WO 2008/028946, WO2010/130636, WO 2013/007770).

Isolated Mutant Hemagglutinin Polypeptides

According to the present invention new isolated mutant hemagluttinin polypeptides have been designed presenting epitopes for recognition by broadly protecting antibodies. These polypeptides can be used to create a universal epitope-based vaccine inducing protection against a broad range of influenza strains. The polypeptides are stabilized and then the highly variable and immunodominant part, i.e. the head domain, is shielded, immunodampened, through the introduction of glycan molecules. The head can have multiple glycans to shield the epitopes from being recognized by the immune system, thus redirecting the immune response towards the more conserved neck and stem domain to produce broadly protective antibodies.

The isolated mutant hemagluttinin polypeptides of this invention are capable of presenting the conserved epitopes to the immune system in the absence of dominant epitopes that are present in the membrane distal head domain. To this end, part of the primary sequence of the hemagluttinin polypeptide making up the head domain is shielded with glycan molecules. The resulting polypeptide sequence is further modified by introducing specific amino acid substitutions that stabilize the native 3-dimensional structure of the remaining part of the hemagglutinin polypeptide.

According to the invention, the isolated mutant hemagglutinin polypeptides comprise one or more additional mutations, i.e. amino acid substitutions and/or glycan motif substitutions, in the head domain, the stem domain, and/or the receptor binding site substitution, as compared to the amino acid sequence of corresponding wild-type influenza virus hemagglutinin polypeptide, i.e. the influenza virus on which the mutant hemagglutinin polypeptides are based.

According to embodiments of the invention, the isolated mutant hemagglutinin polypeptides comprise amino acid substitutions, glycan motif substitutions, receptor binding site substitutions, and/or deletion mutations. When referencing the substitutions and deletion mutations, an amino acid position(s) for the substitution(s) and/or deletion(s) is provided. The amino acid position corresponds to the amino acid sequence of SEQ ID NO:1, as provided herein. By way of an example, an amino acid substitution at amino acid position 227 would correspond to an amino acid substitution of the lysine (K) at position 227 of SEQ ID NO:1. By way of another example, an amino acid substitution at amino acid position 238 would correspond to an amino acid substitution of the histidine at position 238 of SEQ ID NO:1. The specific amino acid position and residue can vary based on the starting hemagglutinin polypeptide sequence of a specific influenza strain; however, one skilled in the art would be capable of performing a sequence alignment to identify the corresponding amino acid position and residue that corresponds to the position on SEQ ID NO:1.

In embodiments of the invention, amino acid substitutions at the specific amino acid positions will be chosen based on factors which include, but are not limited to, potential for steric hindrance, charge attraction, charge repulsion, common properties of the amino acid side chain, secondary and/or tertiary structure considerations, and/or frequency of use in respective host cells. A person skilled in the art would understand which factors to consider when designing amino acid substitutions for the isolated mutant influenza hemagglutinin polypeptides of the invention.

In certain aspects of the invention, provided herein are isolated mutant influenza hemagglutinin polypeptides comprising at least two stabilizing mutations in the polypeptide, wherein the stabilizing mutations comprise substitution mutations at (a) amino acid positions 227 and/or 238; and/or (b) amino acid positions 384 and/or 476, wherein the amino acid position corresponds to the amino acid position of SEQ ID NO:1. In certain embodiments, (a) amino acid position 227 is substituted with an amino acid selected from the group consisting of Q, N, F, I, and Y, and/or amino acid position 238 is substituted with an amino acid selected from the group consisting of N, Q, I, and F; and/or (b) amino acid position 384 is substituted with an amino acid selected from the group consisting of W, F, N, Q, and I, and/or amino acid position 476 is substituted with an amino acid selected from the group consisting of W, F, Y, I, N, and Q. In certain embodiments, (a) amino acid position 227 is substituted with a Q and amino acid position 238 is substituted with an I; and/or (b) amino acid position 384 is substituted with an I and amino acid position 476 is substituted with an I.

In certain embodiments, the isolated mutant influenza hemagglutinin polypeptide further comprises one additional stabilizing mutation in the polypeptide. The additional stabilizing mutation is a substitution at amino acid position 461, wherein the amino acid position corresponds to the amino acid position in SEQ ID NO:1. In certain embodiments, amino acid position 461 is substituted with an amino acid selected from the group consisting of M, L, W, Y, and R. In certain embodiments, amino acid position 461 is substituted with an R.

The isolated mutant influenza hemagglutinin polypeptide can, for example, comprise an amino acid sequence selected from SEQ ID NO:19, SEQ ID NO:35, SEQ ID NO:39 or SEQ ID NO:40. The isolated mutant influenza hemagglutinin polypeptide can, for example, comprise the amino acid sequence of SEQ ID NO:8 or SEQ ID No: 108.

In certain aspects of the invention, the isolated mutant influenza hemagglutinin polypeptide further comprises at least one additional glycan motif in a head domain of the polypeptide. The glycan motif can, for example, comprise a substitution of an amino (N)-linked glycosylation motif in at least one amino acid position selected from the group consisting of (a) 136 or 137, (b) 141, and (c) 151, wherein the amino acid position corresponds to the amino acid position of SEQ ID NO:1. The glycan motif can, for example, comprise a substitution of the N-linked glycosylation motif at amino acid positions 136 and 141, 136 and 151, 137 and 141, 137 and 151, or 141 and 151. In certain embodiments, the glycan motif comprises the substitution of the N-linked glycosylation motif at amino acid positions 141 and 151. In certain embodiments, the mutant influenza hemagglutinin polypeptide comprises an amino acid sequence selected from SEQ ID NO:42, SEQ ID NO:43, SEQ ID NO:44, or SEQ ID NO:45.

In certain aspects of the invention, the isolated mutant influenza hemagglutinin polypeptide further comprises or solely comprises a receptor binding site mutation in the polypeptide. The receptor binding site mutation can, for example, comprise a substitution at an amino acid position selected from the group consisting of (a) 175, (b) 219, (c) 257, and (d) 258, wherein the amino acid position corresponds to the amino acid position of SEQ ID NO:1. In certain embodiments, (a) 175 is substituted with an amino acid selected from the group consisting of F, W, and Y; (b) 219 is substituted with an amino acid selected from the group consisting of F, W, Y, R, and E; (c) 257 is substituted with an amino acid selected from the group consisting of E, D, V, F; or (d) 258 is substituted with an amino acid selected from the group consisting of E, D, V, and F. In certain embodiments, (a) 175 is substituted with a W, (b) 219 is substituted with an E, (c) 257 is substituted with an E, or (d) 258 is substituted with an E. In certain embodiments, the mutant influenza hemagglutinin polypeptide comprises an amino acid sequence selected from SEQ ID NO:50, SEQ ID NO:51, SEQ ID NO:55, or SEQ ID NO:61.

In certain embodiments, the isolated mutant influenza hemagglutinin polypeptide further comprises an amino acid substitution at position 136, wherein the amino acid position corresponds to the amino acid position of SEQ ID NO:1.

In certain aspects of the invention, the isolated mutant influenza hemagglutinin polypeptide, further comprises or solely comprises a fusion peptide proximal region (FPPR) deletion mutation. The FPPR deletion mutation can, for example, comprise a deletion of at least three to seven amino acid residues between amino acid position 369 and 382, wherein the amino acid position corresponds to the amino acid position of SEQ ID NO:1. The FPPR deletion mutation can, for example, comprise a deletion selected from the group consisting of Δ372-376, Δ372-378, Δ373-377, Δ373-376, Δ374-379, Δ374-376, Δ376-380, and Δ377-381. In certain embodiments, the FPPR deletion mutation is a deletion selected from Δ372-376 or Δ376-380. In certain embodiments, the mutant influenza hemagglutinin polypeptide comprises an amino acid sequence selected from SEQ ID NO:62 or SEQ ID NO:68.

In certain embodiments, the isolated mutant hemagglutinin polypeptide comprises an amino acid sequence selected from SEQ ID NO:70, SEQ ID NO:81, SEQ ID NO:82, SEQ ID NO:83, or SEQ ID NO:84.

In certain embodiments, the mutant influenza hemagglutinin polypeptide further comprises an amino acid substitution at a cleavage site at amino acid position 362, wherein wherein the amino acid position corresponds to the amino acid position of SEQ ID NO:1. The cleavage site substitution at amino acid position 362 can, for example, be a Q.

In certain embodiments, the isolated mutant influenza hemagglutinin polypeptide is derived from a hemagglutinin of an influenza B virus. In particular, the isolated mutant influenza hemagglutinin polypeptide can be derived from hemagglutinin of an influenza B virus from the B/Yamagata lineage (as represented by B/Yamagata/16/88) or from the B/Victoria lineage (as represented by B/Victoria/2/87). In certain embodiments, the polypeptide is derived from B/Brisbane/60/08, B/Iowa/06/2017, or B/Lee/40.

In certain embodiments, the isolated mutant influenza hemagglutinin polypeptide can comprise a heterologous trimerization domain (e.g., a foldon).

In certain embodiments, the isolated mutant influenza hemagglutinin polypeptide further comprises a carboxy (C)-terminal truncation starting at an amino acid position from amino acid 532 to amino acid position 549, wherein the amino acid positon corresponds to the amino acid position of SEQ ID NO:1. In certain embodiments, the C-terminal truncation starts at amino acid position 532, 534, 536, 539, 541, 543, 545, 547, or 549, wherein the amino acid position corresponds to the amino acid position of SEQ ID NO:1.

Influenza hemagglutinin (HA) in its native form exists as a trimer on the cell or virus membrane. In certain embodiments the intracellular and transmembrane sequence is removed so that a secreted (soluble) polypeptide is produced following expression in cells. Methods to express and purify secreted ectodomains of HA have been described (see e.g. Dopheide et al 2009; Ekiert et al 2009, 2011; Stevens et al 2004, 2006; Wilson et al 1981). A person skilled in the art will understand that these methods can also be applied directly to the isolated mutant hemagglutinin polypeptides of the invention in order to achieve expression of secreted (soluble) polypeptide. Therefore, these polypeptides are also encompassed in the invention.

Optionally, a his-tag sequence (HHHHHH (SEQ ID NO: 85) or HHHHHHH (SEQ ID NO: 86)) may be linked to the (optionally truncated) isolated mutant hemagglutining polypeptide, for purification purposes, optionally connected through a linker. Optionally the linker may contain a proteolytic cleavage site to enzymatically remove the his-tag after purification.

In certain embodiments, the polypeptides are further stabilized by introducing a sequence known to form trimeric structures, i.e. GYIPEAPRDGQAYVRKDGEWVLLSTFL (SEQ ID NO: 87) at the C-terminus of isolated mutant hemagglutinin polypeptide, optionally connected through a linker. Thus, in certain embodiments, the C-terminal part of the isolated mutant hemagglutinin polypeptide has been replaced by the amino acid sequence GYIPEAPRDGQAY-VRKDGEWVLLSTFL (SEQ ID NO: 87), optionally connected through a linker. The linker can contain a cleavage site for processing afterwards according to protocols well known to those skilled in the art. To facilitate purification of the soluble form, a tag sequence may be added, e.g. a histidine tag (HHHHHH (SEQ ID NO: 85) or HHHHHHH (SEQ ID NO: 86)) or FLAG tag (DYKDDDDK) (SEQ ID NO: 88) or a combination of these, optionally connected via short linkers. The linker may optionally contain (part of) a proteolytic cleavage site, e.g., IEGR (SEQ ID NO: 89) (Factor X) or LVPRGS (SEQ ID NO: 90) (thrombin) for processing afterwards according to protocols well known to those skilled in the art. The processed proteins are also encompassed in the invention.

The mutant influenza hemagglutinin polypeptides can be prepared according to any technique deemed suitable to one of skill, including techniques described below.

Thus, the immunogenic polypeptides of the invention can be synthesized as DNA sequences by standard methods known in the art and cloned and subsequently expressed, in vitro or in vivo, using suitable restriction enzymes and methods known in the art. The present invention thus also relates to nucleic acid molecules encoding the above described polypeptides. The invention further relates to vectors comprising the nucleic acids encoding the polypeptides of the invention. In certain embodiments, a nucleic acid molecule according to the invention is part of a vector, e.g. a plasmid. Such vectors can easily be manipulated by methods well known to the person skilled in the art and can, for instance, be designed for being capable of replication in prokaryotic and/or eukaryotic cells. In addition, many vectors can directly or in the form of an isolated desired fragment therefrom be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. When host cells are used, it is preferred that the vector is an integrating vector. Alternatively, the vector can be an episomally replicating vector.

The person skilled in the art is capable of choosing suitable expression vectors and inserting the nucleic acid sequences of the invention in a functional manner. To obtain expression of nucleic acid sequences encoding polypeptides, it is well known to those skilled in the art that sequences capable of driving expression can be functionally linked to the nucleic acid sequences encoding the polypeptide, resulting in recombinant nucleic acid molecules encoding a protein or polypeptide in expressible format. In general, the promoter sequence is placed upstream of the sequences that should be expressed. Many expression vectors are available in the art, e.g. the pcDNA and pEF vector series of Invitrogen, pMSCV and pTK-Hyg from BD Sciences, pCMV-Script from Stratagene, etc, which can be used to obtain suitable promoters and/or transcription terminator sequences, polyA sequences, and the like. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression can include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest can be from the natural promoter or derivative thereof or from an entirely heterologous promoter (Kaufman, 2000). Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al, 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001), actin promoter, an immunoglobulin promoter, heat shock promoters, and the like. Testing for promoter function and strength of a promoter is a matter of routine for a person skilled in the art, and in general can encompass cloning a test gene such as lacZ, luciferase, GFP, etc. behind the promoter sequence, and test for expression of the test gene. Of course, promoters can be altered by deletion, addition, mutation of sequences therein, and tested for functionality, to find new, attenuated, or improved promoter sequences. According to the present invention, strong promoters that give high transcription levels in the eukaryotic cells of choice are preferred.

The constructs can be transfected into eukaryotic cells (e.g. plant, fungal, yeast or animal cells) or suitable prokaryotic expression systems like E. coli using methods that are well known to persons skilled in the art. In some cases a suitable 'tag' sequence (such as for example, but not limited to, a his-, myc-, strep-, or flag-tag) or complete protein (such as for example, but not limited to, maltose binding protein or glutathione S transferase) can be added to the sequences of the invention to allow for purification and/or identification of the polypeptides from the cells or supernatant. Optionally a sequence containing a specific proteolytic site can be included to afterwards remove the tag by proteolytic digestion.

Purified polypeptides can be analyzed by spectroscopic methods known in the art (e.g. circular dichroism spectroscopy, Fourier Transform Infrared spectroscopy and NMR spectroscopy or X-ray crystallography) to investigate the presence of desired structures like helices and beta sheets. ELISA, Octet and FACS and the like can be used to investigate binding of the polypeptides of the invention to the broadly neutralizing antibodies described previously (CR9114, CR8071, CR8033) (Dreyfus et al., Science 337 (6100):1343-8 (2012)). Thus, polypeptides according to the invention having the correct conformation can be selected.

Pharmaceutical/Immunogenic Compositions and Methods of Use

The invention further relates to immunogenic compositions comprising a therapeutically effective amount of at least one of the polypeptides and/or nucleic acids of the invention. The immunogenic compositions preferably further comprise a pharmaceutically acceptable carrier. In the present context, the term "pharmaceutically acceptable" means that the carrier, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The term "carrier" refers to a diluent, adjuvant, excipient, or vehicle with which the composition is administered. Saline solutions and aqueous dextrose and glycerol solutions can, e.g., be employed as liquid carriers, particularly for injectable solutions. The exact formulation should suit the mode of administration. The polypeptides and/or nucleic acid molecules preferably are formulated and administered as a sterile solution. Sterile solutions are prepared by sterile filtration or by other methods known in the art. The solutions can then be lyophilized or filled into pharmaceutical dosage containers. The pH of the solution generally is in the range of pH 3.0 to 9.5, e.g. pH 5.0 to 7.5.

The invention also relates to influenza mutant hemagglutinin polypeptides, nucleic acid molecules and/or vectors as described above for use in inducing an immune response against influenza HA protein. The invention also relates to methods for inducing an immune response in a subject, the method comprising administering to a subject, a polypeptide, nucleic acid molecule and/or immunogenic composition as described above. A subject according to the invention preferably is a mammal that is capable of being infected with an infectious disease-causing agent, in particular an influenza virus, or otherwise can benefit from the induction of an immune response, such subject for instance being a rodent, e.g. a mouse, a ferret, or a domestic or farm animal, or a non-human-primate, or a human. Preferably, the subject is a human subject. The invention thus provides methods for inducing an immune response to an influenza virus hemagglutinin (HA) in a subject utilizing the polypeptides, nucleic acids and/or immunogenic compositions described herein.

Since it is well known that small proteins and/or nucleic acid molecules do not always efficiently induce a potent immune response, it can be necessary to increase the immunogenicity of the polypeptides and/or nucleic acid molecules by adding an adjuvant. In certain embodiments, the immunogenic compositions described herein comprise, or are administered in combination with, an adjuvant. The adjuvant for administration in combination with a composition described herein can be administered before, concomitantly with, or after administration of said composition. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, pertussis toxin PT, or tetanus toxoid TT, Matrix M (Isconova). In addition, known immunopotentiating technologies may be used, such as fusing the polypeptides of the invention to proteins known in the art to enhance immune response (e.g. tetanus toxoid, CRM197, rCTB, bacterial flagellins or others) or including the polypeptides in virosomes, or combinations thereof. Other nonlimiting examples that can be used are e.g. disclosed by Coffman et al. (2010).

In an embodiment, the influenza mutant hemagglutinin polypeptides of the invention are incorporated into viral-like particle (VLP) vectors. VLPs generally comprise a viral polypeptide(s) typically derived from a structural protein(s) of a virus. Preferably, the VLPs are not capable of replicating. In certain embodiments, the VLPs can lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art.

In a specific embodiment, the polypeptides of the invention are incorporated into a virosome. A virosome containing a polypeptide according to the invention can be produced using techniques known to those skilled in the art. For example, a virosome can be produced by disrupting a purified virus, extracting the genome, and reassembling particles with the viral proteins (e.g., the mutant influenza hemagglutinin polypeptides described herein) and lipids to form lipid particles containing viral proteins.

The invention also relates to the above-described polypeptides, nucleic acids and/or immunogenic compositions for inducing an immune response in a subject against influenza HA, in particular for use as a vaccine. The influenza mutant hemagglutinin polypeptides, nucleic acids encoding such polypeptides, or vectors comprising such nucleic acids or polypeptides described herein thus can be used to elicit protective antibodies against influenza viruses, for example, against the neck or stem domain of the influenza virus hemagglutinin. The invention in particular relates to polypeptides, nucleic acids, and/or imunogenic compositions as described above for use as a vaccine in the prevention and/or treatment of a disease or condition caused by an influenza virus.

The polypeptides of the invention can be used after synthesis in vitro or in a suitable cellular expression system, including bacterial and eukaryotic cells, or alternatively, can be expressed in vivo in a subject in need thereof, by expressing a nucleic acid coding for the immunogenic polypeptide. Such nucleic acid vaccines may take any form, including naked DNA, plasmids, or viral vectors including adenoviral vectors.

Administration of the polypeptides, nucleic acid molecules, and/or immunogenic compositions according to the invention can be performed using standard routes of administration. Non-limiting examples include parenteral administration, such as intravenous, intradermal, transdermal, intramuscular, subcutaneous, etc, or mucosal administration, e.g. intranasal, oral, and the like. The skilled person will be capable to determine the various possibilities to administer the polypeptides, nucleic acid molecules, and/or immunogenic compositions according to the invention, in order to induce an immune response. In certain embodiments, the polypeptide, nucleic acid molecule, and/or immunogenic composition (or vaccine) is administered more than one time, i.e. in a so-called homologous prime-boost regimen. In certain embodiments where the polypeptide, nucleic acid molecule, and/or immunogenic composition is administered more than once, the administration of the second dose can be performed after a time interval of, for example, one week or more after the administration of the first dose, two weeks or more after the administration of the first dose, three weeks or more after the administration of the first dose, one month or more after the administration of the first dose, six weeks or more after the administration of the first dose, two months or more after the administration of the first dose, 3 months or more after the administration of the first dose, 4 months or more after the administration of the first dose, etc, up to several years after the administration of the first dose of the polypeptide, nucleic acid molecule, and/or immunogenic composition. It is also possible to administer the vaccine more than twice, e.g. three times, four times, etc, so that the first priming administration is followed by more than one boosting administration. In other embodiments, the polypeptide, nucleic acid molecule, and/or immunogenic composition according to the invention is administered only once.

The polypeptides, nucleic acid molecules, and/or immunogenic compositions can also be administered, either as prime, or as boost, in a heterologous prime-boost regimen.

The invention further provides methods for preventing and/or treating an influenza virus disease in a subject utilizing the polypeptides, nucleic acids and/or compositions described herein. In a specific embodiment, a method for preventing and/or treating an influenza virus disease in a subject comprises administering to a subject in need thereof an effective amount of a polypeptide, nucleic acid and/or immunogenic composition, as described above. A therapeutically effective amount refers to an amount of the polypeptide, nucleic acid, and/or composition as defined herein, that is effective for preventing, ameliorating and/or treating a disease or condition resulting from infection by an influenza virus. Prevention encompasses inhibiting or reducing the spread of influenza virus or inhibiting or reducing the onset, development or progression of one or more of the symptoms associated with infection by an influenza virus. Ameloriation as used in herein can refer to the reduction of visible or perceptible disease symptoms, viremia, or any other measurable manifestation of influenza infection.

Those in need of treatment include those already inflicted with a condition resulting from infection with an influenza virus, as well as those in which infection with influenza virus is to be prevented. The polypeptides, nucleic acids and/or compositions of the invention thus can be administered to a naive subject, i.e., a subject that does not have a disease caused by influenza virus infection or has not been and is not currently infected with an influenza virus infection, or to subjects that already are and/or have been infected with an influenza virus.

In an embodiment, prevention and/or treatment can be targeted at patient groups that are susceptible to influenza virus infection. Such patient groups include, but are not limited to e.g., the elderly (e.g. ≥50 years old, ≥60 years old, and preferably ≥65 years old), the young (e.g. ≤5 years old, ≤1 year old), hospitalized patients and patients who have been treated with an antiviral compound but have shown an inadequate antiviral response.

In another embodiment, the polypeptides, nucleic acids and/or immunogenic compositions can be administered to a subject in combination with one or more other active agents, such as existing, or future influenza vaccines, monoclonal antibodies and/or antiviral agents, and/or antibacterial, and/or or immunomodulatory agents. The one or more other active agents can be beneficial in the treatment and/or prevention of an influenza virus disease or can ameliorate a symptom or condition associated with an influenza virus disease. In some embodiments, the one or more other active agents are pain relievers, anti-fever medications, or therapies that alleviate or assist with breathing.

Dosage regimens of the polypeptides and/or nucleic acid molecules of the invention can be adjusted to provide the optimum desired response (e.g., a therapeutic response). A suitable dosage range may for instance be 0.1-100 mg/kg body weight, preferably 1-50 mg/kg body weight, preferably 0.5-15 mg/kg body weight. The precise dosage of the polypeptides and/or nucleic acid molecules to be employed will e.g. depend on the route of administration, and the seriousness of the infection or disease caused by it and should be decided according to the judgment of the practitioner and each subject's circumstances. For example, effective doses vary depending on target site, physiological state of the patient (including age, body weight, health), and whether treatment is prophylactic or therapeutic. Usually, the patient is a human, but non-human mammals, including transgenic mammals can also be treated. Treatment dosages are optimally titrated to optimize safety and efficacy.

The polypeptides of the invention can also be used to verify binding of monoclonal antibodies identified as potential therapeutic candidates. In addition, the polypeptides of the invention can be used as diagnostic tool, for example to test the immune status of an individual by establishing whether there are antibodies in the serum of such individual capable of binding to the polypeptides of the invention. The invention thus also relates to an in vitro diagnostic method for detecting the presence of an influenza infection in a patient said method comprising the steps of a) contacting a biological sample obtained from said patient with a polypeptide according to the invention; and b) detecting the presence of antibody-antigen complexes. The polypeptides of the invention can also be used to identify new binding molecules or improve existing binding molecules, such as monoclonal antibodies and antiviral agents.

The invention is further illustrated in the following examples and figures. The examples are not intended to limit the scope of the invention in any way.

EMBODIMENTS

The invention provides also the following non-limiting embodiments.

Embodiment 1 is an isolated mutant influenza hemagglutinin polypeptide comprising at least two stabilizing mutations in the polypeptide, wherein the stabilizing mutations comprise substitution mutations at:

a. amino acid positions 227 and/or 238; and/or b. amino acid positions 384 and/or 476, wherein the amino acid position corresponds to the amino acid position of SEQ ID NO:1.

Embodiment 2 is the isolated mutant influenza hemagglutinin polypeptide of embodiment 1, wherein a. amino acid position 227 is substituted with an amino acid selected from the group consisting of Q, N, F, I, and Y, and/or amino acid position 238 is substituted with an amino acid selected from the group consisting of N, Q, I, and F; and/or b. amino acid position 384 is substituted with an amino acid selected from the group consisting of W, F, N, Q, and I, and/or amino acid position 476 is substituted with an amino acid selected from the group consisting of W, F, Y, I, N, and Q.

Embodiment 3 is the isolated mutant influenza hemagglutinin polypeptide of embodiment 2, wherein a. amino acid position 227 is substituted with a Q and amino acid position 238 is substituted with an I; and/or b. amino acid position 384 is substituted with an I and amino acid position 476 is substituted with an I.

Embodiment 4 is the isolated mutant influenza hemagglutinin polypeptide of any one of embodiments 1 to 3, further comprising one stabilizing mutation in the polypeptide, wherein the stabilizing mutation is a substitution at amino acid position 461, wherein the amino acid position corresponds to the amino acid position in SEQ ID NO:1.

Embodiment 5 is the isolated mutant influenza hemagglutinin polypeptide of embodiment 4, wherein amino acid position 461 is substituted with an amino acid selected from the group consisting of M, L, W, Y, and R.

Embodiment 6 is the isolated mutant influenza hemagglutinin polypeptide of embodiment 5, wherein amino acid position 461 is substituted with an R.

Embodiment 7 is the isolated mutant influenza hemagglutinin polypeptide of embodiment 3, wherein the mutant influenza hemagglutinin polypeptide comprises an amino acid sequence selected from SEQ ID NO:19, SEQ ID NO:35, SEQ ID NO:39 or SEQ ID NO:40.

Embodiment 8 is the isolated mutant influenza hemagglutinin polypeptide of embodiment 6, wherein the mutant influenza hemagglutinin polypeptide comprises an amino acid sequence of SEQ ID NO:8.

Embodiment 9 is the isolated mutant influenza hemagglutinin polypeptide of any one of embodiments 1 to 8, further comprising at least one additional glycan motif in a head domain of the polypeptide.

Embodiment 10 is the isolated mutant influenza hemagglutinin polypeptide of embodiment 9, wherein the glycan motif comprises a substitution of an amino (N)-linked glycosylation motif in at least one amino acid position selected from the group consisting of:

a. 136 or 137, b. 141, and c. 151, wherein the amino acid position corresponds to the amino acid position of SEQ ID NO:1.

Embodiment 11 is the isolated mutant influenza hemagglutinin polypeptide of embodiment 10, wherein the glycan motif comprises the substitution of the N-linked glycosylation motif at amino acid positions 136 and 141, 136 and 151, 137 and 141, 137 and 151, or 141 and 151.

Embodiment 12 is the isolated mutant influenza hemagglutinin polypeptide of embodiment 11, wherein the glycan motif comprises the substitution of the N-linked glycosylation motif at amino acid positions 141 and 151.

Embodiment 13 is the isolated mutant influenza hemagglutinin polypeptide of embodiment 10, wherein the mutant influenza hemagglutinin polypeptide comprises an amino acid sequence selected from SEQ ID NO:42, SEQ ID NO:43, SEQ ID NO:44, or SEQ ID NO:45.

Embodiment 14 is the isolated mutant influenza hemagglutinin polypeptide of claim any one of embodiments 1 to 13, further comprising a receptor binding site mutation in the polypeptide.

Embodiment 15 is the isolated mutant influenza hemagglutinin polypeptide of embodiment 14, wherein the receptor binding site mutation comprises a substitution at an amino acid position selected from the group consisting of:

a. 175, b. 219, c. 257, and d. 258, wherein the amino acid position corresponds to the amino acid position of SEQ ID NO:1.

Embodiment 16 is the isolated mutant influenza hemagglutinin polypeptide of embodiment 15, wherein a. 175 is substituted with an amino acid selected from the group consisting of F, W, and Y;

b. 219 is substituted with an amino acid selected from the group consisting of F, W, Y, R, and E;

c. 257 is substituted with an amino acid selected from the group consisting of E, D, V, F; or d. 258 is substituted with an amino acid selected from the group consisting of E, D, V, and F.

Embodiment 17 is the isolated mutant influenza hemagglutinin polypeptide of embodiment 16, wherein a. 175 is substituted with a W, b. 219 is substituted with an E, c. 257 is substituted with an E, or d. 258 is substituted with an E.

Embodiment 18 is the isolated mutant influenza hemagglutinin polypeptide of embodiment 17, wherein the mutant influenza hemagglutinin polypeptide comprises an amino acid sequence selected from SEQ ID NO:50, SEQ ID NO:51, SEQ ID NO:55, or SEQ ID NO:61.

Embodiment 19 is the isolated mutant influenza hemagglutinin polypeptide of any one of embodiments 14-18, wherein the polypeptide further comprises an amino acid substitution at position 136, wherein the amino acid position corresponds to the amino acid position of SEQ ID NO:1.

Embodiment 20 is the isolated mutant influenza hemagglutinin polypeptide of any one of embodiments 1-19, further comprising a fusion peptide proximal region (FPPR) deletion mutation.

Embodiment 21 is the isolated mutant influenza hemagglutinin polypeptide of embodiment 20, wherein the FPPR deletion mutation comprises a deletion of at least three to seven amino acid residues between amino acid position 369 and 382, wherein the amino acid position corresponds to the amino acid position of SEQ ID NO:1.

Embodiment 22 is the isolated mutant influenza hemagglutinin polypeptide of embodiment 21, wherein the FPPR deletion mutation comprises a deletion selected from the group consisting of Δ372-376, Δ372-378, Δ373-377, Δ373-376, Δ374-379, Δ374-376, Δ376-380, and Δ377-381.

Embodiment 23 is the isolated mutant influenza hemagglutinin polypeptide of embodiment 22, wherein the FPPR deletion mutation comprises a deletion selected from 4372-376 or 4376-380.

Embodiment 24 is the isolated mutant influenza hemagglutinin polypeptide of embodiment 23, wherein the mutant influenza hemagglutinin polypeptide comprises an amino acid sequence selected from SEQ ID NO:62 or SEQ ID NO:68.

Embodiment 25 is the isolated mutant influenza hemagglutinin polypeptide of any one of embodiments 1-24, wherein the mutant hemagglutinin polypeptide comprises an amino acid sequence selected from SEQ ID NO:70, SEQ ID NO:81, SEQ ID NO:82, SEQ ID NO:83, or SEQ ID NO:84.

Embodiment 26 is an isolated mutant influenza hemagglutinin polypeptide comprising a fusion peptide proximal region (FPPR) deletion mutation, wherein the FPPR deletion mutation comprises a deletion of at least three to seven amino acid residues between amino acid position 369 and 382, wherein the amino acid position corresponds to the amino acid position of SEQ ID NO:1.

Embodiment 27 is the isolated mutant influenza hemagglutinin polypeptide of embodiment 26, wherein the FPPR deletion mutation comprises a deletion selected from the group consisting of Δ372-376, Δ372-378, Δ373-377, Δ373-376, Δ374-379, Δ374-376, Δ376-380, and Δ377-381.

Embodiment 28 is the isolated mutant influenza hemagglutinin polypeptide of embodiment 26 or 27, wherein the FPPR deletion mutation comprises a deletion selected from 4372-376 or 4376-380.

Embodiment 29 is the isolated mutant influenza hemagglutinin polypeptide of embodiment 28, wherein the mutant influenza hemagglutinin polypeptide comprises an amino acid sequence selected from SEQ ID NO:62 or SEQ ID NO:68.

Embodiment 30 is an isolated mutant influenza hemagglutinin polypeptide comprising a receptor binding site mutation in the polypeptide, wherein the receptor binding site mutation comprises a substitution mutation at an amino acid position selected from the group consisting of:
   a. 175,
   b. 219,
   c. 257, and
   d. 258,
wherein the amino acid position corresponds to the amino acid position of SEQ ID NO:1.

Embodiment 31 is the isolated mutant influenza hemagglutinin polypeptide of embodiment 30, wherein
   a. 175 is substituted with an amino acid selected from the group consisting of F, W, and Y;
   b. 219 is substituted with an amino acid selected from the group consisting of F, W, Y, R, and E;
   c. 257 is substituted with an amino acid selected from the group consisting of E, D, V, F; or
   d. 258 is substituted with an amino acid selected from the group consisting of E, D, V, and F.

Embodiment 32 is the isolated mutant influenza hemagglutinin polypeptide of embodiment 31, wherein
   a. 175 is substituted with a W,
   b. 219 is substituted with an E,
   c. 257 is substituted with an E, or
   d. 258 is substituted with an E.

Embodiment 33 is the isolated mutant influenza hemagglutinin polypeptide of embodiment 32, wherein the mutant influenza hemagglutinin polypeptide comprises an amino acid sequence selected from SEQ ID NO:50, SEQ ID NO:51, SEQ ID NO:55, or SEQ ID NO:61.

Embodiment 34 is the isolated mutant influenza hemagglutinin polypeptide of any of embodiments 30-33, wherein the polypeptide further comprises an amino acid substitution at amino acid position 136, wherein the amino acid position corresponds to the amino acid position of SEQ ID NO:1.

Embodiment 35 is the isolated mutant influenza hemagglutinin polypeptide of any one of embodiments 1 to 17, 19 to 23, 26 to 28, 30 to 32, or 34, wherein the mutant influenza hemagglutinin polypeptide comprises a heterologous trimerization domain.

Embodiment 36 is the isolated mutant influenza hemagglutinin polypeptide of any one of claims 1 to 34, wherein the mutant influenza hemagglutinin polypeptide further comprises a carboxy (C)-terminal truncation starting at an amino acid position from amino acid 532 to amino acid position 549, wherein the amino acid position corresponds to the amino acid position of SEQ ID NO:1.

Embodiment 37 is the isolated mutant influenza hemagglutinin polypeptide of embodiment 36, wherein the C-terminal truncation starts at amino acid position 532, 534, 536, 539, 541, 543, 545, 547, or 549.

Embodiment 38 is the isolated mutant influenza hemagglutinin polypeptide of any one of embodiments 1-37, wherein the mutant influenza hemagglutinin polypeptide further comprises an amino acid substitution at a cleavage site at amino acid position 362, wherein wherein the amino acid position corresponds to the amino acid position of SEQ ID NO:1.

Embodiment 39 is the isolated mutant influenza hemagglutinin polypeptide of embodiment 38, wherein amino acid position 362 is substituted with a Q.

Embodiment 40 is an isolated nucleic acid encoding the isolated mutant influenza hemagglutinin polypeptide of any one of embodiments 1-39.

Embodiment 41 is a vector comprising the isolated nucleic acid of embodiment 40.

Embodiment 42 is a host cell comprising the vector of embodiment 41.

Embodiment 43 is a pharmaceutical composition comprising the isolated mutant influenza hemagglutinin polypeptide of any one of embodiments 1-39 and a pharmaceutically acceptable carrier.

Embodiment 44 is a pharmaceutical composition comprising the isolated nucleic acid of embodiment 40.

Embodiment 45 is a pharmaceutical composition comprising the vector of embodiment 41.

Embodiment 46 is a method of inducing an immune response against an influenza virus in a subject in need thereof, the method comprising administering to the subject in need thereof the pharmaceutical composition of any one of embodiments 43 to 45.

Embodiment 47 is a method of producing an isolated mutant influenza hemagglutinin polypeptide, the method comprising culturing the host cell of embodiment 42 under conditions capable of producing the mutant influenza hemagglutinin polypeptide and recovering the mutant influenza hemagglutinin polypeptide from the cell or culture.

Embodiment 48 is a method of producing the pharmaceutical composition of embodiment 43, the method comprising combining the isolated mutant influenza polypeptide with a pharmaceutically acceptable carrier.

EXAMPLES

TABLE 1

Standard amino acids, abbreviations and properties

| Amino Acid | 3-Letter | 1-Letter | Side chain polarity | Side chain charge (pH 7.4) |
|---|---|---|---|---|
| alanine | Ala | A | nonpolar | Neutral |
| arginine | Arg | R | polar | Positive |
| asparagine | Asn | N | polar | Neutral |
| aspartic acid | Asp | D | polar | Negative |
| cysteine | Cys | C | nonpolar | Neutral |
| glutamic acid | Glu | E | polar | Negative |
| glutamine | Gln | Q | polar | Neutral |
| glycine | Gly | G | nonpolar | Neutral |
| histidine | His | H | polar | Positive (10%)/ Neutral (90%) |
| isoleucine | Ile | I | nonpolar | Neutral |
| leucine | Leu | L | nonpolar | Neutral |
| lysine | Lys | K | polar | Positive |
| methionine | Met | M | nonpolar | Neutral |
| phenylalanine | Phe | F | nonpolar | Neutral |
| proline | Pro | P | nonpolar | Neutral |
| serine | Ser | S | polar | Neutral |
| threonine | Thr | T | polar | Neutral |
| tryptophan | Trp | W | nonpolar | Neutral |
| tyrosine | Tyr | Y | polar | Neutral |
| valine | Val | V | nonpolar | Neutral |

Example 1: Stem Based Polypeptides—Structure and Design Elements

The structure and location of alterations in the sequence of the polypeptides representing the ectodomain of influenza virus haemagglutinin (HA$_0$) are shown in FIG. 1A. When expressed as a soluble ectodomain, the polypeptides were carboxy (C)-terminally truncated; e.g. at position 536 of SEQ ID NO:1, as it is noted that for UFV180846, SEQ ID NO:2, the polypeptide is only 535 amino acids) omitting the native C-terminal transmembrane and cytosolic domain (amino acids 550-585). It is noted that for the numbering of the amino acid positions, the Wild Type HA B/Brisbane/60/08 (SEQ ID NO:1) numbering was used and included the signal peptide (residues 1-15).

Figure 1B:
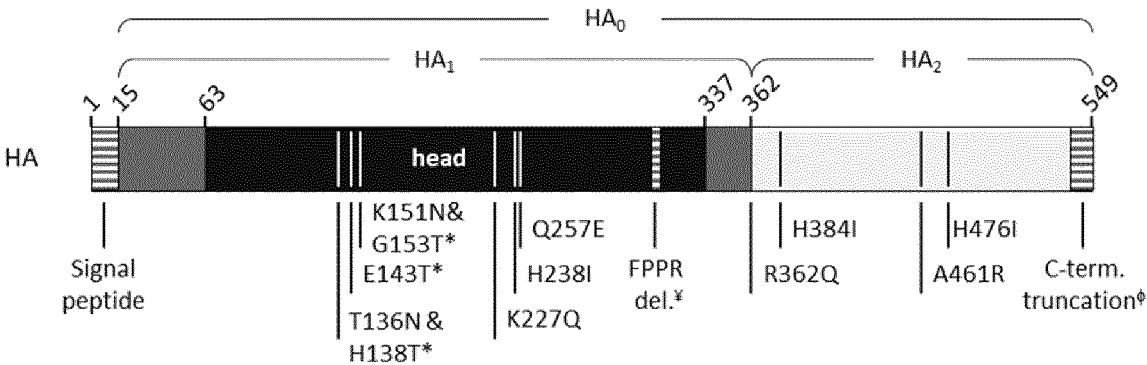

To stabilize HA, increase the expression, and ensure correct folding and trimerization similar to the parental wild-type full-length HA, substitutions were introduced in the polypeptides at positions 227, 238, 384, 461, and 476 (FIGS. 1A-1B).

To improve the HA stem epitope accessibility for broadly binding antibodies, e.g. mAb CR9114 (as described in WO2013/007770), the length of the flexible loop comprising the fusion proximal region (FPPR, amino acids 362-382) was reduced by a about 5 amino acids in certain polypeptides.

To obstruct receptor or antibody binding to the solvent exposed surfaces of the HA head domain in certain polypeptides, the conserved receptor binding site (RBS) was substituted (Q257E) and/or one or more amino acids residues were substituted to introduce the amino (N)-linked glycosylation motif (NxS/T, whereas x is not a P, i.e. at positions 136, 141 and 151) or alternatively substituted to a charged residue (i.e. at positions 136 and 257).

The polypeptides can be resistant to trypsin like protease cleavage by substituting the natural monobasic cleavage site amino acid arginine (R) at position 362 (FIG. 1B) into, e.g. glutamine (Q). In contrast to native pre-fusion HA, polypeptides of the invention including the R329Q substitution are trypsin like protease resistant and cannot be cleaved anymore. Without cleavage into HA$_1$ and HA$_2$ the influenza virus hemagglutinin protein is unable to undergo conformational changes to the post-fusion state and can subsequently not mediate viral fusion.

Example 2: Characterization of Stabilizing Mutations

Designs

Figures 2A, 2B:
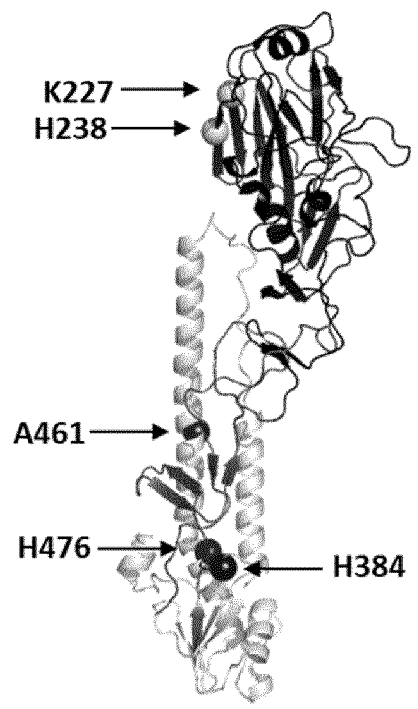

The soluble polypeptides represented the influenza virus hemagglutinin (HA) of influenza Type B. Multiple residue substitutions with the aim to stabilize and improve the folding of the polypeptides were tested at position 461 (FIG. 2B), at positions 227 and 238 (FIG. 2C), and at positions 384 and 476 (FIG. 2D). Expression and folding of the polypeptides were assessed in Expi293F cell culture supernatant.

Protein Expression in Mammalian Cells

DNA fragments encoding the polypeptides were synthesized (Genscript; Piscataway, NJ) and cloned in the pcDNA2004 expression vector (modified pcDNA3 plasmid with an enhanced CMV promotor).

The polypeptides contained a carboxy (C)-terminal foldon trimerization domain (except for UFV171348, SEQ ID NO:39 and UFV171387, SEQ ID NO:40) and a FLAG-Linker-His tag for screening purposes and purification. They were produced in the eukaryotic suspension cell line Expi293F at micro scale (200 µL). In short, cells were transiently transfected with industrial grade DNA in 96-half-deepwell plates (System Duetz) at a cell density of 2.5× 10E+06 vc/mL using the ExpiFectamine 293 transfection kit (Gibco, ThermoFisher Scientific; Waltham, MA) and incubated in Expi293 Expression Medium (Gibco, ThermoFisher Scientific) at 37° C., 250 rpm, 8% CO$_2$ and 75% humidity. Cell culture supernatants containing secreted polypeptides were harvested at day 3 and clarified by centrifugation (10 minutes at 400×g) followed by filtration (96-well Filter plates, 0.22 µm PVDF membrane, Corning; Corning, NY).

Culture Supernatant Analysis

Expression and folding of the polypeptides were assessed by amplified luminescent proximity homogeneous assay (AlphaLISA, FIGS. 2B-2D) according to the manufacturer's instructions (PerkinElmer; Waltham, MA). This in-solution and in-binding-equilibrium assay is based on successful binding of both a donor and acceptor bead to the polypeptides via specific antibodies. When in close proximity, laser irradiation of the donor bead at 680 nm generated a flow of singlet oxygen, triggering chemical events in a nearby acceptor bead, resulting in chemiluminescent emission at 615 nm. Expression levels were measured via the Expression-AlphaLISA setup by simultaneous addition of Nickel donor beads (that binds/complexes with the His tag) and beads coupled to an antibody directed against the FLAG tag to the cell culture supernatant. This Expression-AlphaLISA setup recognized the C-terminal FLAG-Linker-His tag irrespective of the folding of the polypeptides. The correct folding of the polypeptides was assessed in a Binding-AlphaLISA by simultaneous addition of Nickel donor beads, human IgG antibody CR9114 (as described in WO2013/007770) at a concentration of 2 nM, and anti-human IgG acceptor beads to the cell culture supernatant. A signal was only obtained if the polypeptide correctly folded and permitted the binding of the influenza virus HA specific IgGs.

For all AlphaLISA setups, the detector beads were added at a concentration of 10 µg/mL. The culture supernatants were tested at different dilutions to avoid the hook-effect according to the manufacturer's instructions. Readout was performed 2 hours after incubation at room temperature in the dark using the EnSight™ multimode plate reader (Perki-nElmer). Data were normalized to reference construct UFV170090 (SEQ ID NO:3), wild type HA B/Brisbane/60/08 (SEQ ED NO:1) including a foldon trimerization domain and a FLAG-Linker-His tag, that was set to 100%.

The thermo-stability of the polypeptides was determined by Differential Scanning Fluorimetry (DSF) by monitoring the fluorescent emission of added Sypro Orange Dye (ThermoFisher Scientific) to the culture supernatant. Upon gradual increase of the temperature, from 25° C. to 95° C. (60° C. per hour), the polypeptides unfolded, and the fluorescent dye bound to the exposed hydrophobic residues leading to a characteristic change in emission. The melting curves were measured using a ViiA7 real time PCR machine (Applied Biosystems; Foster City, CA), and the $Tm_{50}$ values were calculated by the Spotfire suite (Tibco Software Inc.; Palo Alto, CA). The $Tm_{50}$ values represent the temperature at which 50% of the protein is unfolded and thus are a measure for the temperature stability of the polypeptides.

The content of the expressed polypeptides in the Expi293F cell culture harvests was assessed by analytical Size Exclusion Chromatography (SEC) in an Ultra High-Performance Liquid Chromatography (UHPLC) using a Vanquish system (ThermoFisher Scientific) with a BEH 200A column (Waters, injection volume 40 μL, flow 0.35 mL/min.). The elution was monitored by a Helios light scattering detector (Wyatt Technology; Goleta, CA). The SEC profiles were analyzed by the Astra 6 software package (Wyatt Technology).

Results and Conclusion

Most of the alternative amino acids at position 461 were well tolerated, except for the Tryptophan (UFV171702, SEQ ID NO:6) that resulted in a decrease of −40% mAb CR9114 binding of (FIG. 2B). Polypeptide UFV171741 (SEQ ID NO:8) that included an arginine residue at position 461 displayed −2.8-fold increase in mAb CR9114 binding. Substitution of the residue at position 227 resulted in an −1.5-fold increase of CR9114 binding for the amino acids tested, whereas substitutions at position 238 did not affect antibody binding (FIG. 2C). A combination of a glutamine and isoleucine at these positions, respectively, resulted in a significant increase of CR9114 binding (~2.5-fold). Introducing substitutions to position 384 resulted in a 3 to 4-fold decrease in CR9114 binding, whereas substitutions at position 476 were well tolerated or resulted in a modest increase in binding levels (UFV170550 (SEQ ID NO:29) and UFV170551 (SEQ ID NO:30)). Polypeptides with both residues substituted displayed a significant decrease in CR9114 binding, except when both residues were substituted to an isoleucine. This combination (UFV170556 (SEQ ID NO:35)) displayed a −2.3-fold increase in CR9114 binding (FIG. 2C). Temperature stability of the polypeptide, as determined by DSF, indicated a 3.9° C. increase in $Tm_{50}$ upon introduction of the Q227 and 1238 substitutions (UFV170525 (SEQ ID NO:19) vs UFV170090 (SEQ ID NO:3), whereas the expression level was not significantly affected (FIG. 2D).

Figure 2F:
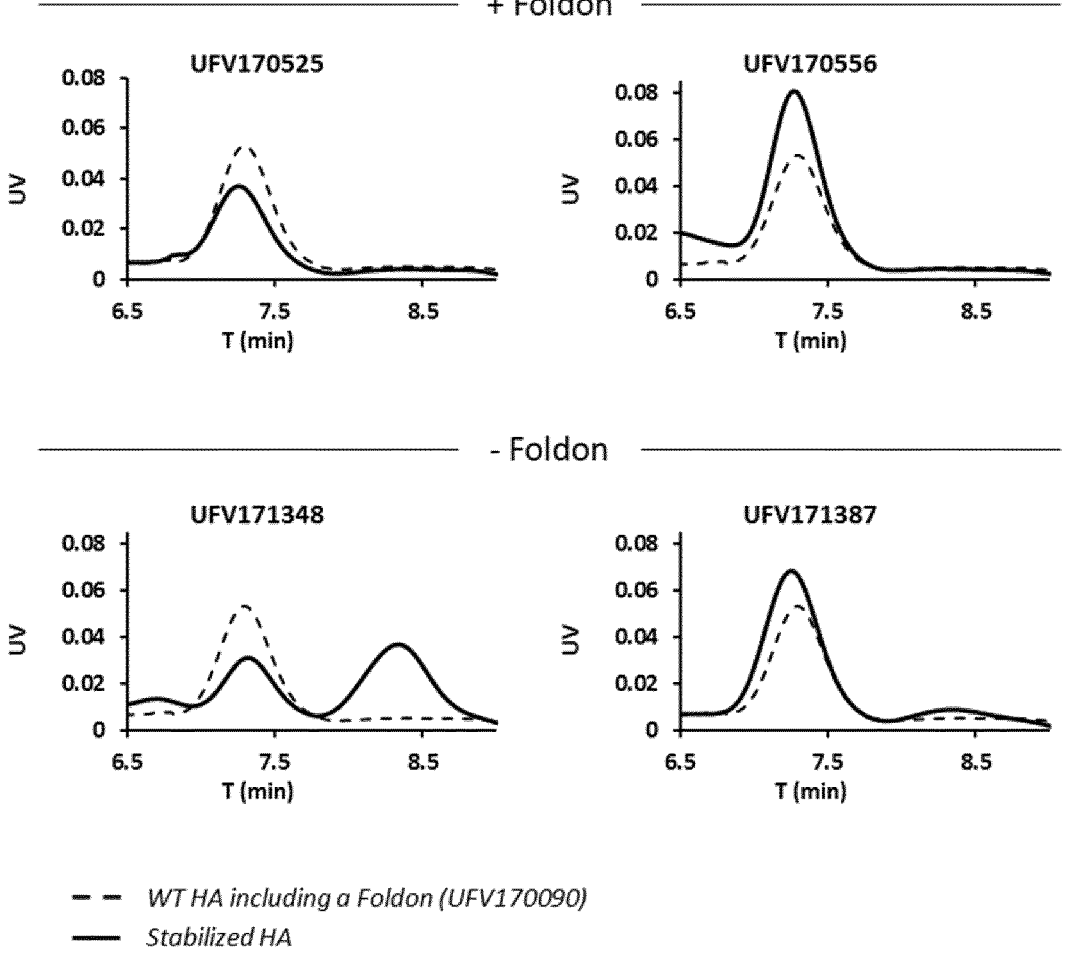

No noteworthy effect of substitutions I384 and I476 on the temperature stability was observed (0.5° C. decrease), however, the polypeptide including these mutations (UFV170556 (SEQ ID NO:35)) displayed an increased expression level (~1.4-fold) and increased binding of CR9114 (~2-fold). Removal of the foldon trimerization domain also resulted in an increase in expression level (UFV171348 (SEQ ID NO:39)) versus UFV170556 (SEQ ID NO:35)), however, a decrease in CR9114 binding was observed. The combination of all four (4) favorable substitutions at positions 227, 238, 384, and 476 resulted in a polypeptide that expressed well (2-fold increase to reference) and bound CR9114 well (~1.7-fold increase to reference). Strikingly, the polypeptide was very stable ($Tm_{50}$ of 64.7° C., 5.2° C. higher than parent construct) and expressed as a soluble trimeric polypeptide in the absence of a foldon trimerization domain (FIG. 2F).

Taken together the results showed that by substituting four (4) residues in the core of the HA, a polypeptide was generated that formed soluble trimers in the absence of heterologous trimerization domains, which represent a correctly folded and stable pre-fusion conformation of wild type influenza B HA.

Figures 3A, 3B:
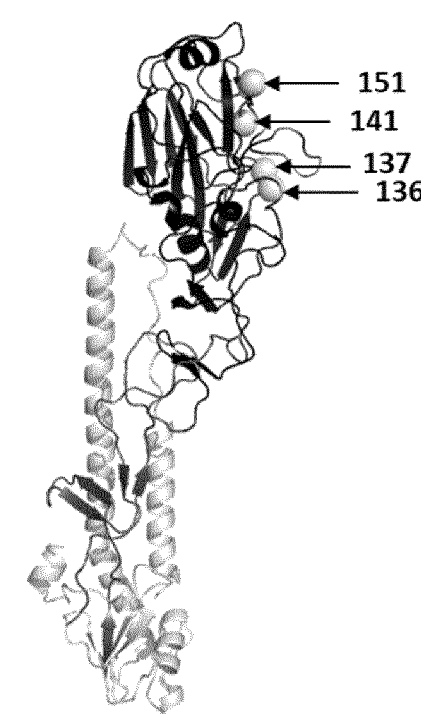
FIGS. 3A-3B show the analysis of EXPI-293 expressed polypeptides with introduced amino (N)-linked glycosylation motifs in the head domain.

Example 3: Characterization of Added N-Linked Glycosylation Motifs to the Head Domain Designs At various positions N-linked glycosylation motifs NxT/S (wherein x is not a P) were introduced to the head domain of the polypeptides. For positions 136, 137, and 151 an N and T were introduced, whereas for position 141 an asparagine was present in the wild type sequence and the motif was completed by introducing a threonine at position 143 (FIG. 3A).

Culture Supernatant Analysis

DNA fragments encoding the polypeptides of the invention were synthesized as described in Example 2. The polypeptides including a FLAG-Linker-His tag for screening purposes and purification were produced in the eukaryotic suspension cell line Expi293F at micro scale (200 μL). UFV171472 (SEQ ID NO:43) was expressed with a Foldon trimerization domain, the other polypeptides were expressed without a Foldon trimerization domain.

Expression and folding of the polypeptides of the invention were assessed by AlphaLISA as described in Example 2. Binding of CR8071 (Dreyfus et al., Science 337(6100): 1343-8 (2012)) and SD84 (Laursen et al., Science 362 (6414):598-602 (2018)) was performed at a concentration of 1.5 nM and 2 nM respectively. The trimer-AlphaLISA setup was used to determine the content of trimeric polypeptides present in the culture supernatant. The trimer-AlphaLISA assay relied on human IgGs such as 46B8C (WO2015/148806A1), which specifically bound to monomeric HA. If a 1:1 mix of differently labeled 46B8C (biotin or DIG labeled) was added to HA, an AlphaLISA signal was only be detected if a multimer, permitting binding of at least two antibodies, was present. It was shown previously that this trimer-AlphaLISA setup preferably detected trimers and was insensitive for dimers, multimers or monomers. Trimer-AlphaLISA was performed by simultaneous addition of Streptavidin donor beads and anti-DIG IgG acceptor beads to the culture supernatant in the presence of biotinylated- and DIG-labelled 46B8C IgGs (each at 1 nM). Data for polypeptides UFV171991 (SEQ ID NO:45), UFV171992 (SEQ ID NO:44), and UFV171993 (SEQ ID NO:42) were normalized to reference construct UFV171990 (SEQ ID NO:41), representing a stabilized B/Brisbane/60/08 HA. For polypeptide UFV171472 (SEQ ID NO:43), data was normalized to reference construct UFV170090 (SEQ ID NO:3), wild type HA B/Brisbane/60/08 including a Foldon trimerization domain. Reference constructs were set to 100%.

Results and Conclusion

The introduction of additional N-linked glycosylation motifs to the head domain of the polypeptides of the invention at positions 136, 137, 141, or 151 was possible (FIG. 3B) and only a minimal decrease in expression levels were observed (up to ~30% for UFV171472 (SEQ ID NO:43)). Binding of stem (CR9114) and neck (CR8071) specific antibodies was maintained, whereas an expected decrease in head domain specific binder SD84 was observed. The highest reduction in SD84 binding was observed for polypeptides with a N-linked glycan introduction at position 137 (UFV171472, SEQ ID NO:43) or at position 151 (UFV171991, SEQ ID NO:45). The head-binding of SD84 was reduced by 40% and 52% respectively relative to the polypeptide without additional N-linked glycosylation sites.

Example 4: Characterization of Receptor Binding Site Modifications

Designs

Figures 4A, 4B:
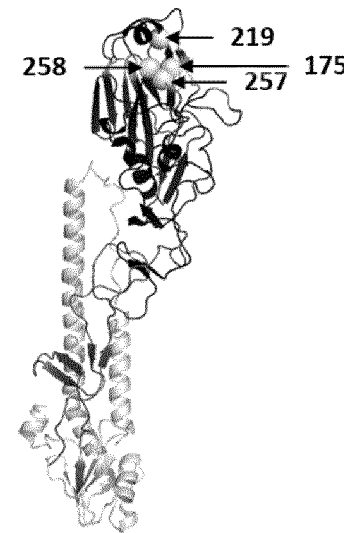
FIGS. 4A-4B show the analysis of EXPI-293 expressed polypeptides with introduced mutations near the receptor binding site.

To reduce the affinity of the conserved receptor binding to its natural ligand sialic acid and to alter the conserved epitope for head-binding antibodies in and around the receptor binding site, point substitutions were introduced in the polypeptides disclosed herein. At position 175, alternative hydrophobic residues were introduced, whereas both hydrophobic and charged residues were evaluated for positions 219, 257, and 258 (FIG. 4A).

Culture Supernatant Analysis

DNA fragments encoding the polypeptides were synthesized as described in Example 2. The polypeptides including a FLAG-Linker-His tag for screening purposes were produced in the eukaryotic suspension cell line Expi293F at micro scale (200 μL). Expression and folding of the polypeptides were assessed by AlphaLISA as described in Examples 2 and 3. Data was normalized to reference construct UFV171990 (SEQ ID NO:41), representing a stabilized B/Brisbane/60/08 HA including FLAG-Linker-His tag, that was set to 100%.

Results and Conclusion

Compared to the reference, all polypeptides with altered residues near or in the receptor binding site displayed reduced expression levels (FIG. 4B). Substitutions at positions 219 and 258 are tolerated least; UFV172072 (SEQ ID NO:54) and UFV172064 (SEQ ID NO:46) were the lowest (11%) and highest (56%) expressed polypeptides. Substitutions at positions 175 and 257 were accepted better with regard to protein expression. Polypeptides UFV172073 (SEQ ID NO:55), UFV172075 (SEQ ID NO:57), and UFV172078 (SEQ ID NO:60) were minimally affected and reach a level of 75%, 70%, and 74% relative to the reference. Similarly, these three polypeptides displayed the highest trimer content; 90%, 89%, and 78% respectively. Furthermore, binding of stem binding monoclonal antibody CR9114 was preserved (71-94%), while binding of head domain specific SD84 was considerably altered; UFV172073 (SEQ ID NO:55) hardly bound (17%), while UFV172075 (SEQ ID NO:57) displayed a drastic increase in binding (579%). For UFV172078, with a substitution at position 175 (SEQ ID NO:60), binding of SD84 was only minimally affected (74%).

Overall, substitutions in and around the receptor binding site were not well tolerated. Polypeptides including the 257E, 257V, or 175W substitution displayed a small but acceptable decrease in expression level, trimer content, and binding of mAb CR9114. The only observed difference with these polypeptides was with binding of SD84.

Example 5: Characterization of Fusion Peptide Proximal Region (FPPR) Deletions in the Polypeptides of the Invention Designs The residues of the structurally undefined loop following the $HA_0$ cleavage site at position 362 was referred to as the Fusion Peptide Proximal Region (FPPR, residues 369-383, FIG. 1A and FIG. 5A). Polypeptides comprising an FPPR deletion of varying length, from 3 to 7 residues, and position were evaluated with the aim to increase the HA stability and accessibility of conserved stem epitopes.

Culture Supernatant Analysis

DNA fragments encoding the polypeptides were synthesized as described in Example 2. The polypeptides including a FLAG-Linker-His tag for screening purposes were produced in the eukaryotic suspension cell line Expi293F at micro scale (200 μL). Expression and folding of the polypeptides were assessed by AlphaLISA as described in Examples 2 and 3. Data was normalized to reference construct UFV171990 (SEQ ID NO:41), representing a stabilized B/Brisbane/60/08 HA including FLAG-Linker-His tag, that was set to 100%.

Results and Conclusion

Figures 5A, 5B:
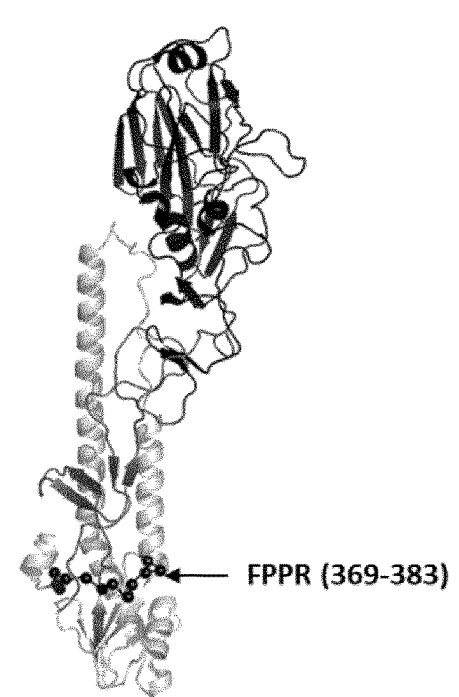
FIGS. 5A-5B show the analysis of EXPI-293 expressed polypeptides with deletions in the Fusion Peptide Proximal Region (FPPR).

Partial deletions of the FPPR did not alter the protein expression levels notably (83-110%, FIG. 5B). For two polypeptides, UFV172680 (SEQ ID NO:63) and UFV172683 (SEQ ID NO:65), a −2-fold decrease in trimer formation was observed, whereas all other polypeptides showed similar trimer content compared to the reference. Larger differences were observed for the binding of stem specific mAb CR9114. With 24% CR9114 binding compared to the reference, UFV172690 (SEQ ID NO:69) showed the lowest binding, which suggested that deletions beyond position 380 were not well tolerated. UFV172680 (SEQ ID NO:63), UFV172683 (SEQ ID NO:65), and UFV172691 (SEQ ID NO:68) also displayed reduced CR9114 binding with 55%, 66%, and 74%, respectively, compared to reference. Binding of neck specific mAb CR8071 was only minimally affected, and the relative binding was within the range of 67% to 104% compared to reference. Binding of head domain specific SD84 displayed a larger spread in binding; UFV172683 (SEQ ID NO:65) showed with a 7 amino acid deletion, the lowest binding (43%), and UFV172686 (SEQ ID NO:66) displayed the highest binding (167%).

Overall, partial deletions of the FPPR were well tolerated; expression level, trimer formation and correct folding were maintained or showed a minimal decrease, even if up to 7 amino acids of this highly conserved loop were removed. Folding of CR9114 was clearly impaired when deletions reach position 381, which was presumably too close to the conserved HA stem epitopes. Polypeptides UFV172680 (SEQ ID NO:63) and UFV172683 (SEQ ID NO:65) showed decreased binding for all assessed antibodies.

Example 6: Alternative Truncations at the C-Terminus

Designs

Hemagglutinin is a membrane protein that is located at the surface of the viral particles and infected cells with the C-terminal part of the protein embedded in the viral membrane. For the soluble versions of the polypeptides, the transmembrane domain was deleted by a truncation at the start of the transmembrane domain (TM). Additionally, alternative truncation positions were evaluated in the stabilized HA B/Brisbane/60/08 reference polypeptide UFV180284 (SEQ ID NO:70). Whereas the reference polypeptide was expressed without a Foldon trimerization domain and including a C-tag, the variants with alternative C-terminal truncations were expressed as tag-free soluble trimeric polypeptides (Table 2).

TABLE 2

Alternative C-terminal truncations of the polypeptides derived
from the ectodomain of HA from B/Brisbane/60/08.

| | C-terminus of HA ectodomain | | | | | | | | | | |
| | 531 | 532 | 533 | 534 | 535 | 536 | 537 | 538 | 539 | 540 | 541 |
|---|---|---|---|---|---|---|---|---|---|---|---|
| B/Brisbane/ 60/08 | S | L | N | I | T | A | A | S | L | N | D |
| UFV180454 | S | L | N | I | T | A | A | S | L | N | D |
| UFV180455 | S | L | N | I | T | A | A | S | L | N | D |
| UFV180456 | S | L | N | I | T | A | A | S | L | N | D |
| UFV180457 | S | L | N | I | T | A | A | S | L | N | D |
| UFV180458 | S | L | N | I | T | A | A | S | L | N | D |
| UFV180459 | S | L | N | I | T | A | A | S | L | — | — |
| UFV180460 | S | L | N | I | T | A | — | — | — | — | — |
| UFV180461 | S | L | N | I | — | — | — | — | — | — | — |
| UFV180462 | S | L | — | — | — | — | — | — | — | — | — |

| | C-terminus of HA ectodomain | | | | | | | | TM | | |
| | 542 | 543 | 544 | 545 | 546 | 547 | 548 | 549 | 550 | 551 | 552 |
|---|---|---|---|---|---|---|---|---|---|---|---|
| B/Brisbane/ 60/08 | D | G | L | D | N | H | T | I | L | L | Y |
| UFV180454 | D | G | L | D | N | H | T | I | — | — | — |
| UFV180455 | D | G | L | D | N | H | — | — | — | — | — |
| UFV180456 | D | G | L | D | — | — | — | — | — | — | — |
| UFV180457 | D | G | — | — | — | — | — | — | — | — | — |
| UFV180458 | — | — | — | — | — | — | — | — | — | — | — |
| UFV180459 | — | — | — | — | — | — | — | — | — | — | — |
| UFV180460 | — | — | — | — | — | — | — | — | — | — | — |
| UFV180461 | — | — | — | — | — | — | — | — | — | — | — |
| UFV180462 | — | — | — | — | — | — | — | — | — | — | — |

"—" indicates the truncated residues between positions 533 and 552.

"TM" stands for trans-membrane domain.

Putative N-glycan sites are highlighted at amino acid position 533 and 546.

Culture Supernatant Analysis

DNA fragments encoding the polypeptides listed in Table 2 were synthesized and expressed in EXPI-293 cell cultures as described in Example 2 and 4. The harvested culture supernatants were analyzed for the presence of expressed trimeric polypeptide by analytical SEC using HPLC as described in Example 2.

Results and Conclusion

Figure 6:
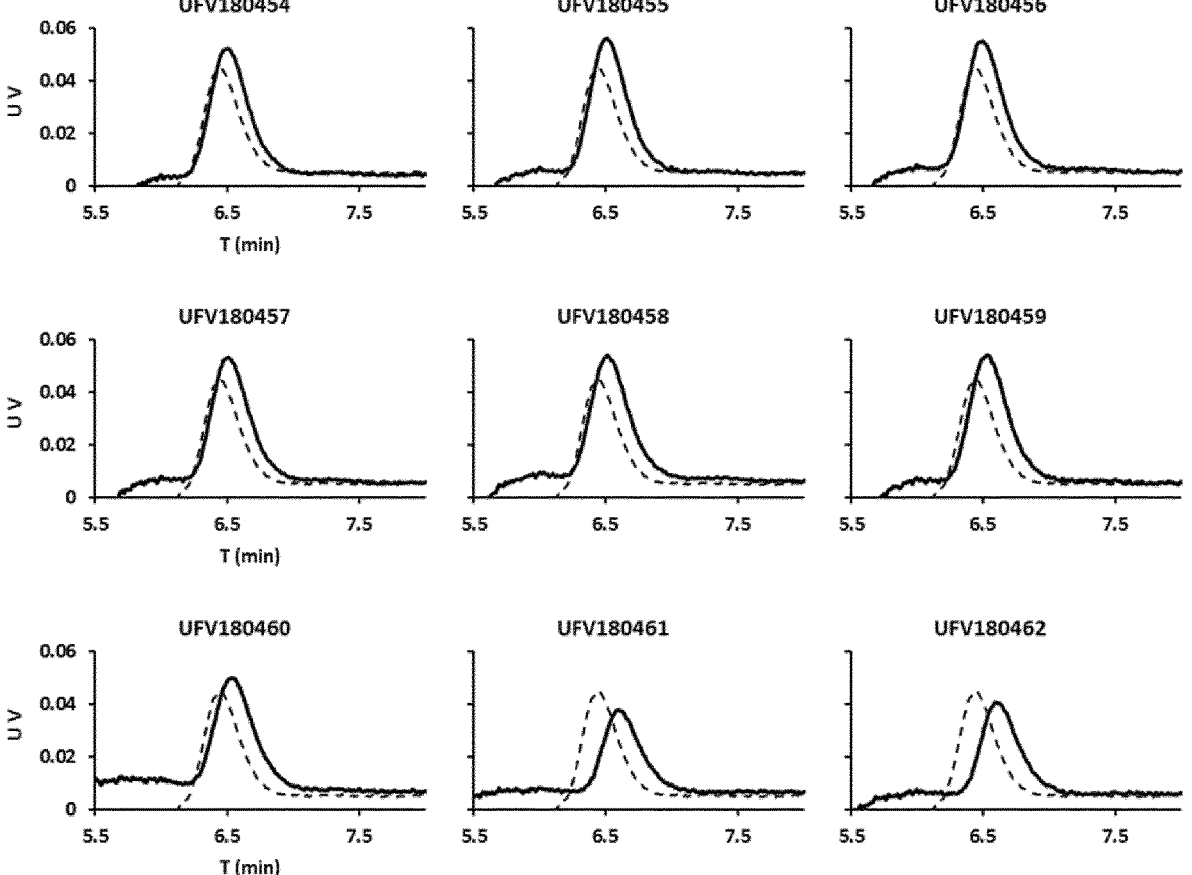
FIG. 6 shows SEC profiles of EXPI-293 culture supernatants expressing soluble trimeric polypeptide variants with alternative C-terminal truncations (in UFV180454 (SEQ ID NO:71) at position 549 stepwise down to position 532 in UFV180462 (SEQ ID NO:79)); polypeptide (black line) and full-length reference UFV180284 (SEQ ID NO:70) (dotted line) that includes a C-tag.

Analysis of the culture supernatants by SEC indicated one major peak (~6.5-minute retention time) for all tested constructs that corresponded to the trimeric form of the polypeptide (FIG. 6). Minimal effect of the alternative C-terminal truncations on the expression level of the trimeric polypeptides was observed; only a minor decrease in trimer peak height was observed for UFV180461 (SEQ ID NO:78) and UFV180462 (SEQ ID NO:79), −20% in peak height compared to reference UFV180284 (SEQ ID NO:70). Furthermore, a gradual increase in retention time in the size exclusion column was observed, which correlated with the decrease in polypeptide trimer size upon the stepwise truncation of the C-terminus. Likely the change in retention time was enhanced by the removal of two putatively N-linked glycosylated asparagine's at positions 533 and/or 546.

In summary, C-terminal truncations between residue 533 and 549 of the polypeptides of the invention were well tolerated and only minor effects on expression levels of the trimeric influenza B HAs were observed.

Example 7: Expression, Purification and In Vitro Characterization of Trimeric Polypeptides of the Invention Designs To characterize the combination of additional N-linked glycosylation motifs, receptor binding site (RBS) substitutions, and deletions in the fusion peptide proximal region, they were introduced in stabilized HA B/Brisbane/60/08 in the absence of a Foldon trimerization domain. In polypeptides without the introduced N-linked glycosylation motif at position 136 a glutamate (E) was introduced; UFV180137 (SEQ ID NO:82), UFV180251 (SEQ ID NO:83), and UFV180284 (SEQ ID NO:84). The RBS substitution (257E) was included in all polypeptides. For comparison purpose, WT HA B/Brisbane/60/08 including C-terminal Foldon trimerization domain (UFV170088: SEQ ID NO:80) was used. All polypeptides were produced in ExpiCHO cells including a C-tag, a four-residue acid peptide (E-P-E-A) fused to the C-terminus of the polypeptides Protein Expression and Purification DNA fragments encoding the polypeptides were synthesized (Genscript) and cloned in the pcDNA2004 expression vector (modified pcDNA3 plasmid with an enhanced CMV promotor). The polypeptides were produced in ExpiCHO suspension cells cultured in ExpiCHO™ expression medium by transient transfection of respective industrial grade DNA (≤0.01 EU/µg endotoxin level and ≥90% supercoil content) using ExpiFectamine™ transfection reagent (Gibco, ThermoFisher Scientific) according to the manufacturer's protocol. ExpiFectamine CHO Enhancer and ExpiCHO Feed (Gibco, ThermoFisher Scientific) were added to the cell cultures 1-day post transfection according to the manufacturer's protocol. Culture supernatants containing the secreted polypeptides were harvested at day 10 and clarified by centrifugation, followed by filtration over a 0.2 µm bottle top filter (Corning). The polypeptides were expressed at medium scale (~70 mL) and larger scale (~350 mL).

The polypeptides were purified by means of a two-step protocol. First, the harvested and clarified culture supernatant (large scale transfection) was loaded on a HiScale 16/20 column (GE Healthcare; Chicago, IL) packed with an affinity resin (Capture Select; ThermoFisher Scientific) that consisted of a C-tag specific single domain antibody, immobilized on Agarose based bead (ThermoFisher Scientific). This resin was highly specific for binding proteins with the C-tag. The amount of applied polypeptide in the harvested culture supernatant was determined by OCTET (anti C-tag) prior to purification. Elution of the C-tagged proteins was performed using a TRIS buffer containing 2M MgCl$_2$. Based on the UV signal (A280) the eluted fractions were pooled and filtered through a Millex-GV 0.22 µm filter membrane (MilliporeSigma; Burlington, MA). Subsequently, the collected elution peak was applied to a Superdex 200 pg 26/60 column (GE Healthcare) equilibrated in running buffer (20 mM Tris, 150 mM NaCl, pH7.8) for polishing purpose, i.e., to remove the minimal amount of multimeric and monomeric protein. Based on the UV signal (A280) the trimer fractions were pooled.

Culture Supernatant and Purified Protein Analysis

The level of expressed polypeptide in the cell culture supernatant was assessed by Bio-Layer Interferometry using the OCTET platform according to the manufacturer's instructions (FortéBio; Fremont, CA). First a standard curve was established, using Streptavidin biosensors (FortéBio), loaded with CaptureSelect™ Biotin anti C-tag conjugate (ThermoFisher Scientific), by assessing the binding shift of a dilution series of a well-defined reference batch of purified homologous polypeptide (stabilized HA B/Brisbane/60/08 including C-terminal C-tag; UFV172551 SEQ ID NO:96). Subsequently, the binding shift of pre-diluted (in kinetics buffer, FortéBio) cell culture supernatants containing the polypeptides was measured and the concentration of the polypeptides was calculated using the established standard curve The trimer content of the polypeptides in the culture supernatant and of purified polypeptide was assessed by Size Exclusion Chromatography Multi Angle Light Scattering (SEC-MALS) analysis using a High Performance Liquid Chromatography (HPLC) Infinity 1260 series setup (Agilent; Santa Clara, CA). Of each purified polypeptide 40 µg was run (1 mL/min.) over a TSK gel G3000SWxl column (Sigma-Aldrich; St. Louis, MO) and the molar mass of the eluted material was measured by a miniDAWN Treos Multi Angle Light Scattering detector and Optilab T-rEx differential refractometer (Wyatt Technology). The data were analyzed by the Astra 6 software package (Wyatt Technology) and molecular weight calculations were derived from the refractive index signal.

The antigenicity of purified polypeptides was assessed by ELISA (EC$_{50}$ values of the antibody binding). To this end, polypeptides were coated at a concentration of nM and incubated with a dilution series of monoclonal antibody (mAb) CR9114 (as described in WO2013/007770), CR8071 (as described in Dreyfus et al., 337(6100):1343-8 (2012)), SD84 (as described in (Laursen et al., Science 362(6414): 598-602 (2018)), and 34B5 (as described in WO2015/148806). A starting concentration of 70 nM was applied for CR9114, CR8071, and 34B5, whereas a starting concentration of 100 nM was used for SD84. Antibody binding was determined by incubation with a secondary antibody, anti-human Fc HRP (Mouse anti-Human IgG, Jackson ImmunoResearch; West Grove, PA) and visualized by addition of POD substrate. Read out was performed using the EnSight™ multimode plate reader (PerkinElmer; Waltham, MA). The EC$_{50}$ values were calculated using the Spotfire suite (Tibco Software Inc.; Palo Alto, CA).

The thermo-stability of the polypeptides was determined in the culture supernatant by Differential Scanning Fluorimetry (DSF) as described in Example 2 by monitoring the fluorescent emission of Sypro Orange Dye (ThermoFisher Scientific) added to a 6 µg polypeptide solution.

Results and Conclusion

Figure 7D:
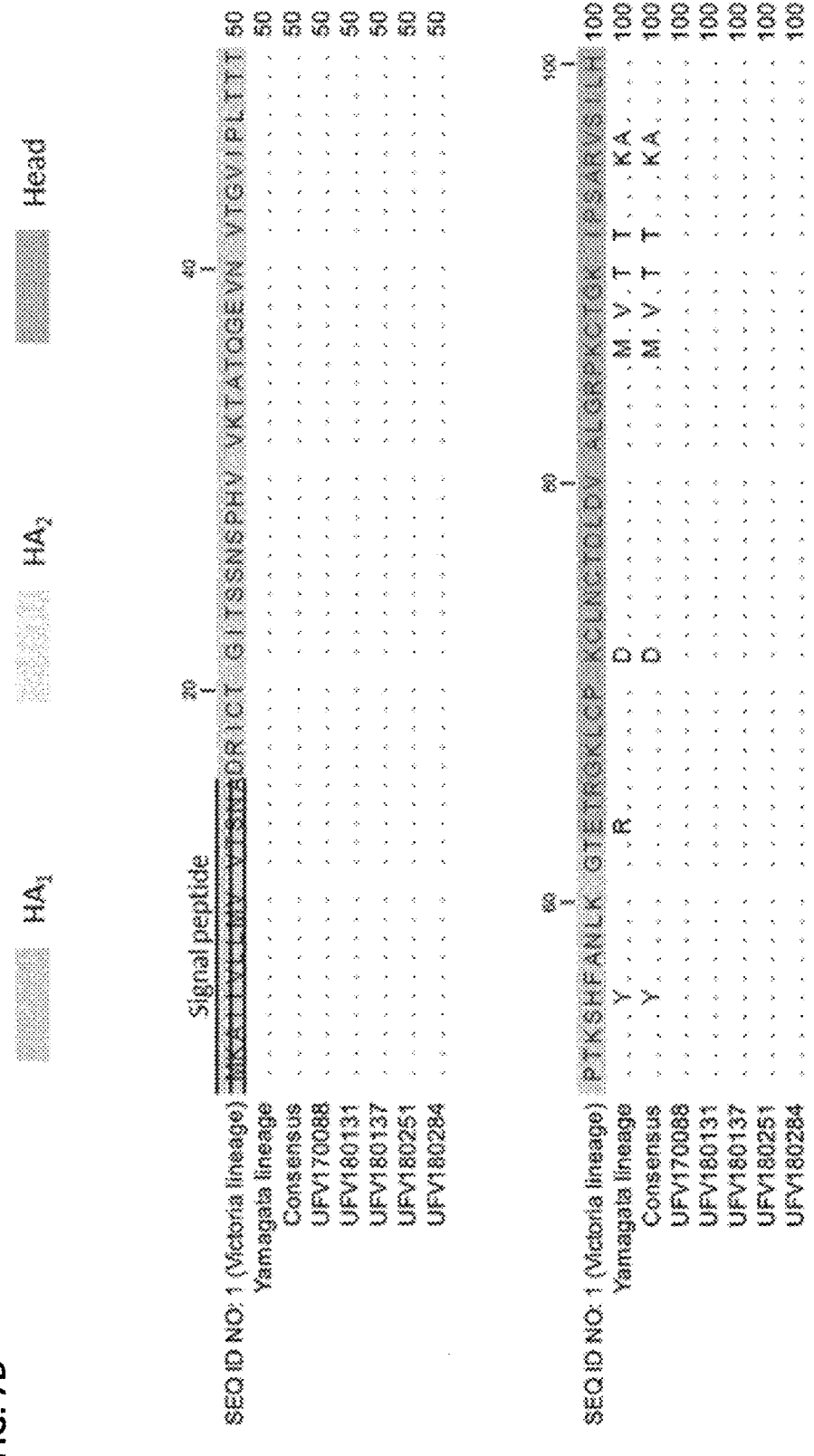
Figure 7E:
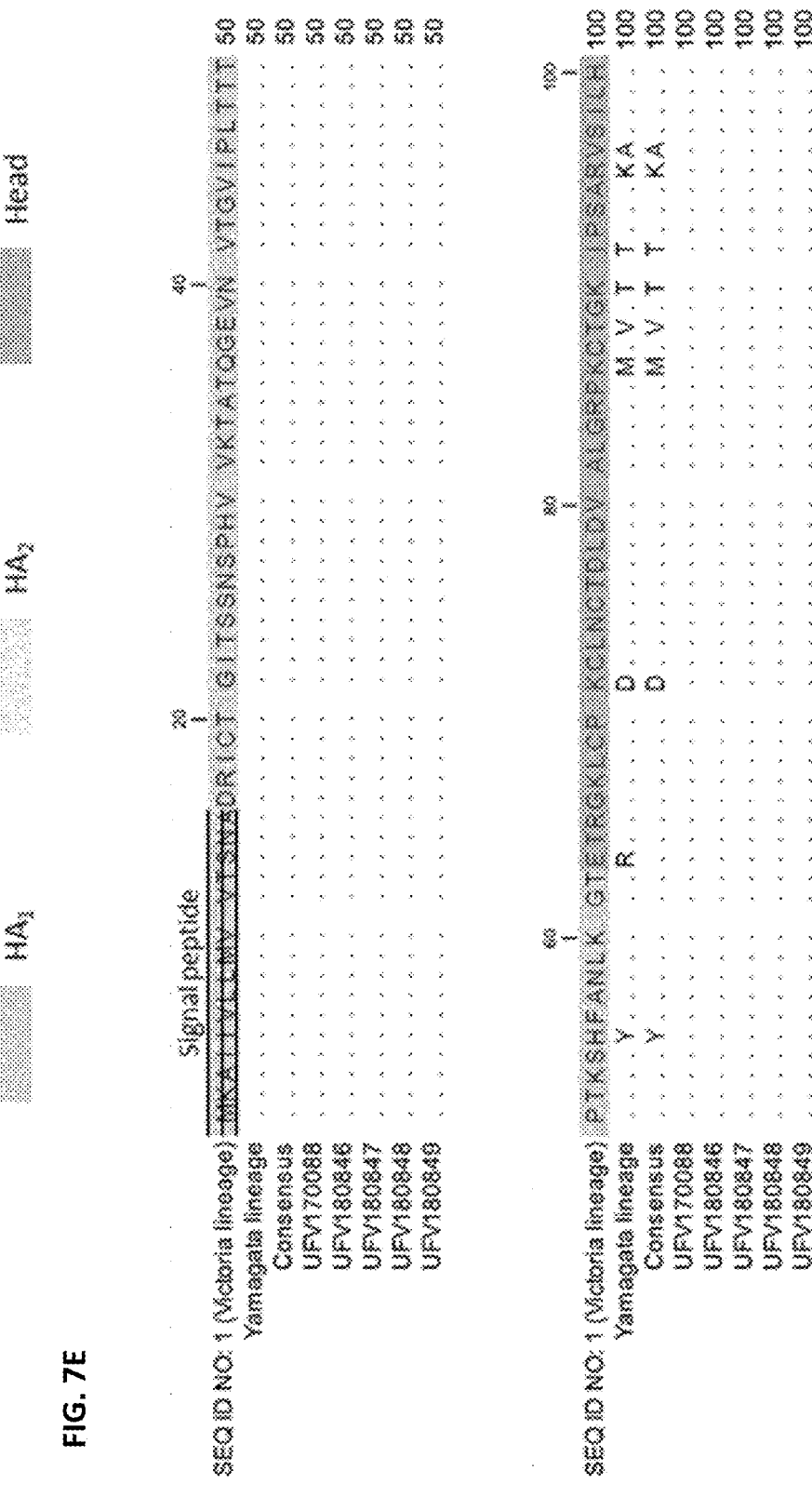

The analysis of crude cell culture supernatant by SEC-MALS (FIG. 7A, left panel) indicated the presence of predominantly soluble trimeric polypeptides (~7 minutes retention time). Similar analysis also indicated that the two-step purification protocol yielded pure trimeric polypeptide (FIG. 7A, right panel). Furthermore, the trimeric polypeptides expressed at a high level as determined by OCTET; up to a 2-fold increase was observed compared to the reference (FIG. 7B). The purified polypeptides were correctly folded as evident by ELISA analysis showing strong CR9114 binding to the stem of the polypeptide (with EC$_{50}$ values in the lower nanomolar range (<2.6 nM)). Similarly, EC$_{50}$ values were observed for binding of neck specific mAb CR8071. In contrast, no binding was observed for the head-domain specific binder SD84. Likely the introduced N-linked glycosylation motifs were glycosylated and prevented SD84 from binding due to steric hindrance by the glycan moieties. The temperature at which 50% of the polypeptide unfolds was determined by DSF. All polypeptides were temperature stable and displayed Tm$_{50}$ values of 68.3° C., 69.2° C., 69.4° C., and 69.3° C. for, respectively, UFV180131 (SEQ ID NO:81), UFV180137 (SEQ ID NO:82), UFV180251 (SEQ ID NO:83), and UFV180284 (SEQ ID NO:84). The Tm$_{50}$ value for the reference, wild type HA including a Foldon trimerization domain, was ~8.6° C. lower, which indicated the combination of substitutions and deletions had a significant effect on the temperature stability of the polypeptide. Using an alternative C-terminal truncation position and knocking out the HA$_0$ cleavage site resulted in a decrease in protein expression level; however, each polypeptide expressed well at a high level that is comparable to the reference (FIG. 7C). Polypeptide folding was not affected and EC$_{50}$ values in the lower nanomolar range were observed (≤4.6 nM) for stem specific mAb CR9114 and neck specific mAb CR8071 binding. Similar to what was observed for SD84, no binding of head-domain specific mAb172498 (WO2015/148806) was observed. Likely, the introduced N-linked glycosylation motifs were glycosylated and prevented binding of mAb172498 due to steric hindrance by the glycan moieties. All polypeptides displayed similar $Tm_{50}$ values compared to the polypeptides with a non-mutated cleavage site and other truncation positions.

In summary, the combination of stabilizing substitutions and fusion peptide proximal region deletion was beneficial and allowed the addition of non-native head domain glycans and receptor binding site substitutions. The polypeptides expressed well, were purified from the cell culture supernatant as properly folded trimeric polypeptides, were temperature stable, and maintained the proper HA folding and trimeric pre-fusion conformation in solution.

Example 8: Expression of Soluble Stabilized Influenza B HA Compared to Wild Type Influenza B HA in Various Subtypes Designs In addition to the HA polypeptides described in Example 2-7, further stabilized Influenza B HAs were expressed and compared to their respective wild type soluble HA ectodomains. Thus, a glutamine (Q) at position 227, isoleucine (I) at position 238, isoleucine (I) at position 384, arginine (R) at position 461, and an isoleucine (I) at position 476 were introduced in the HA amino acid sequences of four additional Influenza B strains: B/Lee/1940, B/Yamagata/16/1988 (Yamagata lineage), B/Florida/04/2006 (Yamagata lineage), and B/Iowa/06/2017 (Victoria lineage). All polypeptide included the fusion peptide proximal region (FPPR) deletion mutation 372-376 except for the B/Iowa/06/2017 derived polypeptide. Expression levels of the polypeptides in Expi293F cell culture supernatant, three days after transfection, were compared to the respective WT polypeptides without the mutations.

Culture Supernatant Analysis

DNA fragments encoding the polypeptides of the invention were synthesized as described in Example 2. The wild type polypeptides including a His-tag and the stabilized polypeptides including a linker-sortase recognition sequence-His tag for screening purposes and purification, were produced in the eukaryotic suspension cell line Expi293F at micro scale (200 µL).

The level of expressed polypeptide in the cell culture supernatant was assessed by Bio-Layer Interferometry using the OCTET platform (FortéBio). In short, a standard curve was established using anti-HIS (HIS2) Biosensors (FortéBio) by measuring the binding shift of a dilution series of a well-defined reference batch of a purified comparable polypeptide. Subsequently, the binding shifts of pre-diluted (in kinetics buffer, FortéBio) cell culture supernatants containing the polypeptides of the invention were measured and the concentration of the polypeptides was calculated using the established standard curve.

The presence of the expressed polypeptides and its quaternary structure (which indicates whether the polypeptide is a monomer, trimer or multimer) in the culture supernatant was assessed by Size Exclusion Chromatography Multi Angle Light Scattering (MALS) in an Ultra High-Performance Liquid Chromatography (UHPLC) setup using a Vanquish system (ThermoFisher Scientific). For the B/Lee/ 40, B/Yamagata/16/1988, and B/Florida/04/2006 derived polypeptides a BEH 200A column (Water, injection volume 40 µL, flow 0.35 mL/min) was used, for the B/Iowa/06/2017 derived polypeptide a Unix-C 300A column (Sepax Technologies, injection volume 15 µL, flow 0.1 mL/min) was used. The elution was monitored by a Helios light scattering detector (Wyatt Technologies). The SEC profiles were analyzed by the Astra 6 software package (Wyatt Technology).

Result and Conclusion

Figures 8A, 8B:
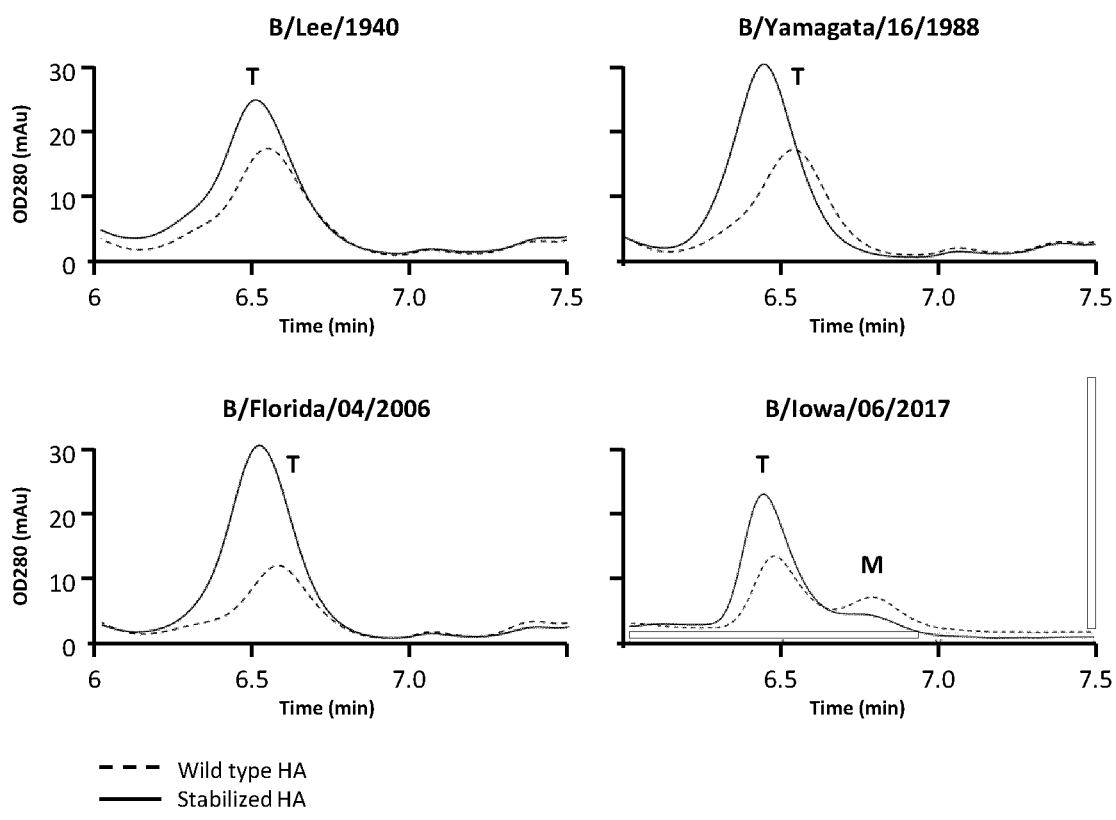

Like observed in Example 2, substitution to glutamine at position 227, and isoleucine's at positions 238, 384 and 476, an arginine at position 461 with or without the deletion of the FPPR (residues 372-376) in the wild type HA of different strains resulted in an increase in expression as determined by Bio-Layer Interferometry (FIG. 8A). The analysis of the crude cell culture supernatant by SEC-MALS (FIG. 8B) showed that upon introduction of the stabilizing mutations, for all soluble stabilized HAs a distinct trimer (T) peak appears at a retention time −6.5 minutes which is higher than the trimer peaks observed for the respective wild type HA ectodomains (FIG. 8.B). Furthermore, none of the stabilized HA displayed a monomer (M) peak as appears at a retention time between 6.5 and 7 minutes for the wild type B/Iowa/ 06/2017 HA.

In summary, the data confirm that introduction of mutations 227Q, 238I, 384I, 461R, and 476I result in an increased expression and formation of stable soluble trimeric HA polypeptides.

REFERENCES

Ambrose et al., Hum. Vaccin. Immunother. 8:81-8 (2012)
Dijkstra et al., Epidemiol. Infect. 137:473-9 (2009)
Dopheide TA, Ward CW, *J Gen Virol.* 367-370 (1981)
Dreyfus et al., Science 337(6100):1343-8 (2012)
Ekiert et al., Science 324:246 (2009).
Ekiert et al., Science 333: 844 (2011).
Ferguson et al. (2003), Nature 422: 428-443 (2003).
Grohskopf et al., MMWR Recomm. Rep. 66:1-20 (2017)
Grohskopf et al., MMWR Recomm. Rep. 67:643-5 (2018)
Krammer et al., Nat. Rev. Disease Primers 4:3 (2018)
Laursen et al., Science 362(6414):598-602 (2018)
Lorieau et al. 2010, Proc. Natl. Acad. Sci. USA, 107: 11341 (2010).
Ni et al., Virology 450-451:71-83 (2014)
Peltola et al., Clin. Infect. Dis. 36:299-305 (2003)
Steven et al., Science 303: 1866 (2004)
Steven et al., Science 312: 404 (2006)
Thompson et al., JAMA 292:1333-40 (2004)
Thompson et al., JAMA 289:179-86 (2003)
Throsby et al. (2008), Plos One 12(3): 1-15 (2008)
Wilson et al (1981) Nature 289: 366 (1981)
US Centers for Disease Control and Prevention, "Seasonal influenza activity surveillance reports 2001-2018" www.cdc.gov/flu/weekly/pastreports.htm (accessed on Jul. 2, 2018)
European Centre for Disease Prevention and Control/WHO Regional Office for Europe, "Annual epidemiological reports on seasonal influenza 2001-2018," ecdc.europa.eu/en/seasonal-influenza/surveillance-and-disease-data/aer (accessed on Jul. 2, 2018)
World Health Organization, "Recommended composition of influenza virus vaccines for use in the 2017-2018 northern hemisphere influenza season," www.who.int/influenza/vaccines/virus/recommendations/2018 19 north/en (accessed on Jul. 2, 2018)
WO2008/028946
WO2010/130636
WO2013/007770
WO2015/148806

SEQUENCES

SEQ ID NO 1: Full length B/Brisbane/60/08
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITAASLNDDGLDNHTILLY
YSTAASSLAVTLMIAIFVVYMVSRDNVSCSICL SEQ ID NO 2: UFV180846
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSNHT
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFEGMIAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAEPEA SEQ ID NO 3: UFV170090
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH SEQ ID NO 4: UFV171700
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELMVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH SEQ ID NO 5: UFV171701
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELLVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH SEQ ID NO 6: UFV171702
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELWVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH SEQ ID NO 7: UFV171703
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELYVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH SEQ ID NO 8: UFV171741
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN

| SEQUENCES |
| --- |

```
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELRVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 9: UFV170519
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 10: UFV170520
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQNFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 11: UFV170521
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQFFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 12: UFV170522
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQIFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 13: UFV170523
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQYFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 14: UFV170515
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTNYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 15: UFV170516
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
```

-continued

| SEQUENCES |
| --- |

```
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTQYVSQIGGFPNQTEDGGLPQSGRIVVDYMVQKSGKTGTI
TYQRGILLPQKVWCASGRSKVIKGSLPLIGEADCLHEKYPYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 16: UFV170517
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 17: UFV170518
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTFYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 18: UFV170524
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTNYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 19: UFV170525
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 20: UFV170541
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWWGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 21: UFV170542
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWFGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 22: UFV170543
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
```

SEQUENCES

VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWNGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 23: UFV170544
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWQGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 24: UFV170545
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 25: UFV170546
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEWLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 26: UFV170547
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 27: UFV170548
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEYLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 28: UFV170549
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEILLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 29: UFV170550
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN

-continued

| SEQUENCES |
| --- |

```
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYPYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDENLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH
```

SEQ ID NO 30: UFV170551
```
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEQLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH
```

SEQ ID NO 31: UFV170552
```
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWWGYTSHGAHGVAVAADLKSTQEAINKITKNL
NSLSELEVKNLQRLSGAMDELHNEILELDEKVDDLRADTISSQIELAVLLSNEGIINSEDEWLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH
```

SEQ ID NO 32: UFV170553
```
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYPYTGEHAKAIGNCPIWVKTPLK
LANGTKYRPPAKLLKERGFFGAIAGFLEGGWEGMIAGWWGYTSHGAHGVAVAADLKSTQEAINKITKNL
NSLSELEVKNLQRLSGAMDELHNEILELDEKVDDLRADTISSQIELAVLLSNEGIINSEDEFLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH
```

SEQ ID NO 33: UFV170554
```
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWFGYTSHGAHGVAVAADLKSTQEAINKITKNL
NSLSELEVKNLQRLSGAMDELHNEILELDEKVDDLRADTISSQIELAVLLSNEGIINSEDELLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH
```

SEQ ID NO 34: UFV170555
```
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWWGYTSHGAHGVAVAADLKSTQEAINKITKNL
NSLSELEVKNLQRLSGAMDELHNEILELDEKVDDLRADTISSQIELAVLLSNEGIINSEDEYLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH
```

SEQ ID NO 35: UFV170556
```
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELAVLLSNEGIINSEDEILLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH
```

SEQ ID NO 36: UFV170557
```
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
```

-continued

| SEQUENCES |
| --- |

VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWNGYTSHGAHGVAVAADLKSTQEAINKITKNL
NSLSELEVKNLQRLSGAMDELHNEILELDEKVDDLRADTISSQIELAVLLSNEGIINSEDENLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 37: UFV170558
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWQGYTSHGAHGVAVAADLKSTQEAINKITKNL
NSLSELEVKNLQRLSGAMDELHNEILELDEKVDDLRADTISSQIELAVLLSNEGIINSEDEQLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 38: UFV170559
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWNGYTSHGAHGVAVAADLKSTQEAINKITKNL
NSLSELEVKNLQRLSGAMDELHNEILELDEKVDDLRADTISSQIELAVLLSNEGIINSEDEQLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 39: UFV171348
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELAVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 40: UFV171387
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELAVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 41: UFV171990
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 42: UFV171993
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSNHT
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 43: UFV171472
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTNN

| SEQUENCES |
| --- |

TINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHHKCNQTCLDRIAAGTFDAGEFSLPTFDSLNITASGSLVPRGSGSGYIPE
APRDGQAYVRKDGEWVLLSTFLGGSLPETGGGSDYKDDDDKGGGGSGGGGSGGGGSHHHHHH

SEQ ID NO 44: UFV171992
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINATNAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 45: UFV171991
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 46: UFV172064
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKFYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 47: UFV172065
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKWYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 48: UFV172066
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKYYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 49: UFV172067
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKRYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 50: UFV172068
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN

| SEQUENCES |
| --- |

```
VINAENAPGGPYKIGTSGSCPNITNGNGFFATMAWAVPKNDKNKTATNPLTIEVPYICTEGEDQITVWG
FHSDNETQMAKEYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 51: UFV172069
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQEGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 52: UFV172070
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQDGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 53: UFV172071
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQVGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 54: UFV172072
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQFGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 55: UFV172073
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 56: UFV172074
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPDSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 57: UFV172075
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
```

SEQUENCES

VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPVSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 58: UFV172076
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPFSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 59: UFV172077
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAFPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 60: UFV172078
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAWPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 61: UFV172079
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAYPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIAAA
DYKDDDDKPGGGGSGGGGSGGGGSGGGGSGGGGSHHHHHH

SEQ ID NO 62: UFV172678
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFEGMIAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAASLNDDGLDNHTIAAADYKDD
DDKPGGGGSGGGGSGGGGSGGGGSGGGGSHHHHHH

SEQ ID NO 63: UFV172680
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLGMIAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAASLNDDGLDNHTIAAADYKDD
DDKPGGGGSGGGGSGGGGSGGGGSGGGGSHHHHHH

SEQ ID NO 64: UFV172681
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN

-continued

---

SEQUENCES

---

VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEIAGWIGYTSHGAHGVAVAADLKSTQEAINKITKNLNSLSEL
EVKNLQRLSGAMDELHNEILELDEKVDDLRADTISSQIELRVLLSNEGIINSEDEILLALERKLKKMLG
PSAVEIGNGCFETKHKCNQTCLDRIAAGTFDAGEFSLPTFDSLNITAASLNDDGLDNHTIAAADYKDDD
DKPGGGGSGGGGSGGGGSGGGGSGGGGSHHHHHH

SEQ ID NO 65: UFV172683
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFMIAGWIGYTSHGAHGVAVAADLKSTQEAINKITKNLNSLSELE
VKNLQRLSGAMDELHNEILELDEKVDDLRADTISSQIELRVLLSNEGIINSEDEILLALERKLKKMLGP
SAVEIGNGCFETKHKCNQTCLDRIAAGTFDAGEFSLPTFDSLNITAASLNDDGLDNHTIAAADYKDDDD
KPGGGGSGGGGSGGGGSGGGGSGGGGSHHHHHH

SEQ ID NO 66: UFV172686
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGMIAGWIGYTSHGAHGVAVAADLKSTQEAINKITKNLNSLS
ELEVKNLQRLSGAMDELHNEILELDEKVDDLRADTISSQIELRVLLSNEGIINSEDEILLALERKLKKM
LGPSAVEIGNGCFETKHKCNQTCLDRIAAGTFDAGEFSLPTFDSLNITAASLNDDGLDNHTIAAADYKD
DDDKPGGGGSGGGGSGGGGSGGGGSGGGGSHHHHHH

SEQ ID NO 67: UFV172687
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGMIAGWIGYTSHGAHGVAVAADLKSTQEAINKITKNLNSL
SELEVKNLQRLSGAMDELHNEILELDEKVDDLRADTISSQIELRVLLSNEGIINSEDEILLALERKLKK
MLGPSAVEIGNGCFETKHKCNQTCLDRIAAGTFDAGEFSLPTFDSLNITAASLNDDGLDNHTIAAADYK
DDDDKPGGGGSGGGGSGGGGSGGGGSGGGGSHHHHHH

SEQ ID NO 68: UFV172691
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAASLNDDGLDNHTIAAADYKDD
DDKPGGGGSGGGGSGGGGSGGGGSGGGGSHHHHHH

SEQ ID NO 69: UFV172690
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAASLNDDGLDNHTIAAADYKDD
DDKPGGGGSGGGGSGGGGSGGGGSGGGGSHHHHHH

SEQ ID NO 70: UFV180284
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIEPE
A

SEQ ID NO 71: UFV180454
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN

| SEQUENCES |
| --- |

```
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTI

SEQ ID NO 72: UFV180455
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNH

SEQ ID NO 73: UFV180456
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLD

SEQ ID NO 74: UFV180457
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDG

SEQ ID NO 75: UFV180458
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLND

SEQ ID NO 76: UFV180459
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASL

SEQ ID NO 77: UFV180460
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITA

SEQ ID NO 78: UFV180461
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNI
```

| SEQUENCES |
| --- |

SEQ ID NO 79: UFV180462
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSL

SEQ ID NO 80: UFV170088
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINAENAPGGPYKIGTSGSCPNITNGNGFFATMAWAVPKNDKNKTATNPLTIEVPYICTEGEDQITVWG
FHSDNETQMAKLYGDSKPQKFTSSANGVTTHYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWHGYTSHGAHGVAVAADLKSTQEAINKITKNL
NSLSELEVKNLQRLSGAMDELHNEILELDEKVDDLRADTISSQIELAVLLSNEGIINSEDEHLLALERK
LKKMLGPSAVEIGNGCFETKHKCNQTCLDRIAAGTFDAGEFSLPTFDSLNITASGSLVPRGSGSGYIPE
APRDGQAYVRKDGEWVLLSTFLGGSEPEA

SEQ ID NO 81: UFV180131
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSNHT
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFEGMIAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAASLNDDGLDNHTIEPEA

SEQ ID NO 82: UFV180137
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFEGMIAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAASLNDDGLDNHTIEPEA

SEQ ID NO 83: UFV180251
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAASLNDDGLDNHTIEPEA

SEQ ID NO 84: UFV180846
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSNHT
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFEGMIAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAEPEA

SEQ ID NO 85: HIS-Tag
HHHHHH

SEQ ID NO 86: HIS-Tag
HHHHHHH

SEQ ID NO 87: Trimerization Domain
GYIPEAPRDGQAYVRKDGEWVLLSTFL

SEQ ID NO 88: FLAG Tag
DYKDDDDK

SEQ ID NO 89: Factor X Proteolytic Cleavage Site
IEGR

-continued

SEQUENCES

SEQ ID NO 90: Thrombin Proteolytic Cleavage Site
LVPRGS

SEQ ID NO 91: UFV180847
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFEGMIAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAEPEA

SEQ ID NO 92: UFV180848
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGAGWIGYTSHGAHGVAVAADLKSTQEAINKITKNLNSLSE
LEVKNLQRLSGAMDELHNEILELDEKVDDLRADTISSQIELRVLLSNEGIINSEDEILLALERKLKKML
GPSAVEIGNGCFETKHKCNQTCLDRIAAGTFDAGEFSLPTFDSLNITAEPEA

SEQ ID NO: 93 UFV180849
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSEHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPESGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKEQGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAEPEA

SEQ ID NO 94: Yamagata lineage (B/Florida/04/06)
MKAIIVLLMVVTSNADRICTGITSSNSPHVVKTATQGEVNVTGVIPLTTTPTKSYFANLKGTRTRGKLC
PDCLNCTDLDVALGRPMCVGTTPSAKASILHEVKPVTSGCFPIMHDRTKIRQLPNLLRGYENIRLSTQN
VIDAEKAPGGPYRLGTSGSCPNATSKSGFFATMAWAVPKDNNKNATNPLTVEVPYICTEGEDQITVWGF
HSDDKTQMKNLYGDSNPQKFTSSANGVTTHYVSQIGSFPDQTEDGGLPQSGRIVVDYMMQKPGKTGTIV
YQRGVLLPQKVWCASGRSKVIKGSLPLIGEADCLHEKYGGLNKSKPYYTGEHAKAIGNCPIWVKTPLKL
ANGTKYRPPAKLLKERGFFGAIAGFLEGGWEGMIAGWHGYTSHGAHGVAVAADLKSTQEAINKITKNLN
SLSELEVKNLQRLSGAMDELHNEILELDEKVDDLRADTISSQIELAVLLSNEGIINSEDEHLLALERKL
KKMLGPSAVEIGNGCFETKHKCNQTCLDRIAAGTFNAGEFSLPTFDSLNITAASLNDDGLDNHTILLYY
STAASSLAVTLMLAIFIVYMVSRDNVSCSICL SEQ ID NO 95: Consensus
MKAIIVLLMVVTSNADRICTGITSSNSPHVVKTATQGEVNVTGVIPLTTTPTKSYFANLKGTETRGKLC
PDCLNCTDLDVALGRPMCVGTTPSAKASILHEVRPVTSGCFPIMHDRTKIRQLPNLLRGYEHIRLSTQN
VIDAEKAPGGPYRLGTSGSCPNATSKNGFFATMAWAVPKDNNKNATNPLTVEVPYICTEGEDQITVWGF
HSDNKTQMKKLYGDSNPQKFTSSANGVTTHYVSQIGGFPDQTEDGGLPQSGRIVVDYMVQKPGKTGTIV
YQRGVLLPQKVWCASGRSKVIKGSLPLIGEADCLHEKYGGLNKSKPYYTGEHAKAIGNCPIWVKTPLKL
ANGTKYRPPAKLLKERGFFGAIAGFLEGGWEGMIAGWHGYTSHGAHGVAVAADLKSTQEAINKITKNLN
SLSELEVKNLQRLSGAMDELHNEILELDEKVDDLRADTISSQIELAVLLSNEGIINSEDEHLLALERKL
KKMLGPSAVDIGNGCFETKHKCNQTCLDRIAAGTFNAGEFSLPTFDSLNITAASLNDDGLDNHTI SEQ ID NO 96: UFV172551
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHIRLSTHN
VINATNAPGGPYNITTSGSCPNITNGNGFFATMAWAVPKNDKNKTATNPLTIEVPYICTEGEDQITVWG
FHSDNETQMAKLYGDSKPQQFTSSANGVTTIYVSQIGGFPNQTEDGGLPQSGRIVVDYMVQKSGKTGTI
TYQRGILLPQKVWCASGRSKVIKGSLPLIGEADCLHEKYGGLNKSKPYYTGEHAKAIGNCPIWVKTPLK
LANGTKYRPPAKLLKERGFFGAIAGFLEGGWEGMIAGWIGYTSHGAHGVAVAADLKSTQEAINKITKNL
NSLSELEVKNLQRLSGAMDELHNEILELDEKVDDLRADTISSQIELRVLLSNEGIINSEDEILLALERK
LKKMLGPSAVEIGNGCFETKHKCNQTCLDRIAAGTFDAGEFSLPTFDSLNITAASLNDDGLDNHTIGGS
EPEA SEQ ID NO 97: UFV180846-secreted
DRICTGITSSNSPHVVKTATQGEVNVTGVIPLTTTPTKSHFANLKGTETRGKLCPKCLNCTDLDVALGR
PKCTGKIPSARVSILHEVRPVTSGCFPIMHDRTKIRQLPNLLRGYEHIRLSNHTVINATNAPGGPYNIT
TSGSCPNITNGNGFFATMAWAVPKNDKNKTATNPLTIEVPYICTEGEDQITVWGFHSDNETQMAKLYGD
SKPQQFTSSANGVTTIYVSQIGGFPNQTEDGGLPESGRIVVDYMVQKSGKTGTITYQRGILLPQKVWCA
SGRSKVIKGSLPLIGEADCLHEKYGGLNKSKPYYTGEHAKAIGNCPIWVKTPLKLANGTKYRPPAKLLK
EQGFFGAIAGFEGMIAGWIGYTSHGAHGVAVAADLKSTQEAINKITKNLNSLSELEVKNLQRLSGAMDE
LHNEILELDEKVDDLRADTISSQIELRVLLSNEGIINSEDEILLALERKLKKMLGPSAVEIGNGCFETK
HKCNQTCLDRIAAGTFDAGEFSLPTFDSLNITA -continued

SEQUENCES

SEQ ID NO 98: UFV180847-secreted
DRICTGITSSNSPHVVKTATQGEVNVTGVIPLTTTPTKSHFANLKGTETRGKLCPKCLNCTDLDVALGR
PKCTGKIPSARVSILHEVRPVTSGCFPIMHDRTKIRQLPNLLRGYEHIRLSEHNVINATNAPGGPYNIT
TSGSCPNITNGNGFFATMAWAVPKNDKNKTATNPLTIEVPYICTEGEDQITVWGFHSDNETQMAKLYGD
SKPQQFTSSANGVTTIYVSQIGGFPNQTEDGGLPESGRIVVDYMVQKSGKTGTITYQRGILLPQKVWCA
SGRSKVIKGSLPLIGEADCLHEKYGGLNKSKPYYTGEHAKAIGNCPIWVKTPLKLANGTKYRPPAKLLK
EQGFFGAIAGFEGMIAGWIGYTSHGAHGVAVAADLKSTQEAINKITKNLNSLSELEVKNLQRLSGAMDE
LHNEILELDEKVDDLRADTISSQIELRVLLSNEGIINSEDEILLALERKLKKMLGPSAVEIGNGCFETK
HKCNQTCLDRIAAGTFDAGEFSLPTFDSLNITA SEQ ID NO 99: UFV180848-secreted
DRICTGITSSNSPHVVKTATQGEVNVTGVIPLTTTPTKSHFANLKGTETRGKLCPKCLNCTDLDVALGR
PKCTGKIPSARVSILHEVRPVTSGCFPIMHDRTKIRQLPNLLRGYEHIRLSEHNVINATNAPGGPYNIT
TSGSCPNITNGNGFFATMAWAVPKNDKNKTATNPLTIEVPYICTEGEDQITVWGFHSDNETQMAKLYGD
SKPQQFTSSANGVTTIYVSQIGGFPNQTEDGGLPESGRIVVDYMVQKSGKTGTITYQRGILLPQKVWCA
SGRSKVIKGSLPLIGEADCLHEKYGGLNKSKPYYTGEHAKAIGNCPIWVKTPLKLANGTKYRPPAKLLK
EQGFFGAIAGFLEGGAGWIGYTSHGAHGVAVAADLKSTQEAINKITKNLNSLSELEVKNLQRLSGAMDE
LHNEILELDEKVDDLRADTISSQIELRVLLSNEGIINSEDEILLALERKLKKMLGPSAVEIGNGCFETK
HKCNQTCLDRIAAGTFDAGEFSLPTFDSLNITA SEQ ID NO 100: UFV180949-secreted
DRICTGITSSNSPHVVKTATQGEVNVTGVIPLTTTPTKSHFANLKGTETRGKLCPKCLNCTDLDVALGR
PKCTGKIPSARVSILHEVRPVTSGCFPIMHDRTKIRQLPNLLRGYEHIRLSEHNVINATNAPGGPYNIT
TSGSCPNITNGNGFFATMAWAVPKNDKNKTATNPLTIEVPYICTEGEDQITVWGFHSDNETQMAKLYGD
SKPQQFTSSANGVTTIYVSQIGGFPNQTEDGGLPESGRIVVDYMVQKSGKTGTITYQRGILLPQKVWCA
SGRSKVIKGSLPLIGEADCLHEKYGGLNKSKPYYTGEHAKAIGNCPIWVKTPLKLANGTKYRPPAKLLK
EQGFFGAIAGFLEGGWEGMIAGWIGYTSHGAHGVAVAADLKSTQEAINKITKNLNSLSELEVKNLQRLS
GAMDELHNEILELDEKVDDLRADTISSQIELRVLLSNEGIINSEDEILLALERKLKKMLGPSAVEIGNG
CFETKHKCNQTCLDRIAAGTFDAGEFSLPTFDSLNITA SEQ ID NO 101: UFV180567
MKAIIVLLMVVTSNADRICTGITSSNSPHVVKTATQGEVNVTGVIPLTTTPTRSHFANLKGTQTRGKLC
PNCFNCTDLDVALGRPKCMGNIPSAKVSILHEVKPVTSGCFPIMHDRTKIRQLPNLLRGYENIRLSTSN
VINAETAPGGPYKVGTSGSCPNVANRNGFFNTMAWVIPKDNNKTAINPVTVEVPYICSEGEDQITVWGF
HSDDKTQMERLYGDSNPQKFTSSANGVTTHYVSQIGGFPNQTEDEGLKQSGRIVVDYMVQKPGKTGTIV
YQRGILLPQKVWCASGRSKVIKGSLPLIGEADCLHEKYGGLNKSKPYYTGEHAKAIGNCPIWVKTPLKL
ANGTKYRPPAKLLKERGFFGAIAGFLEGGWEGMIAGWHGYTSHGAHGVAVAADLKSTQEAINKITKNLN
SLSELEVKNLQRLSGAMNGLHDEILELDEKVDDLRADTISSQIELAVLLSNEGIINSEDEHLLALERKL
KKMLGPSAVEIGNGCFETKHKCNQTCLDRIAAGTFNAGDFSLPTFDSLNITAHHHHHH SEQ ID NO 102: UFV180566
MKAIIVLLMVVTSNADRICTGITSSNSPHVVKTATQGEVNVTGVIPLTTTPTRSHFANLKGTQTRGKLC
PNCFNCTDLDVALGRPKCMGNIPSAKVSILHEVKPVTSGCFPIMHDRTKIRQLPNLLRGYENIRLSTSN
VINAETAPGGPYKVGTSGSCPNVANRNGFFNTMAWVIPKDNNKTAINPVTVEVPYICSEGEDQITVWGF
HSDDKTQMERLYGDSNPQQFTSSANGVTTIYVSQIGGFPNQTEDEGLKQSGRIVVDYMVQKPGKTGTIV
YQRGILLPQKVWCASGRSKVIKGSLPLIGEADCLHEKYGGLNKSKPYYTGEHAKAIGNCPIWVKTPLKL
ANGTKYRPPAKLLKERGFFGAIAGFEGMIAGWIGYTSHGAHGVAVAADLKSTQEAINKITKNLNSLSEL
EVKNLQRLSGAMNGLHDEILELDEKVDDLRADTISSQIELRVLLSNEGIINSEDEILLALERKLKKMLG
PSAVEIGNGCFETKHKCNQTCLDRIAAGTFNAGDFSLPTFDSLNITASGSLVPSGSLPETGGGSHHHHH
H SEQ ID NO 103: UFV180565
MKAIIVLLMVVTSNADRICTGITSSNSPHVVKTATQGEVNVTGVIPLTTTPTKSHFANLKGTKTRGKLC
PNCLNCTDLDVALGRPMCMGTIPSAKASILHEVRPVTSGCFPIMHDRTKIRQLPNLLRGYENIRLSTHN
VINAERAPGGPYRLGTSGSCPNVTSRNGFFATMAWAVPRDNKTATNPLTVEVPYICTKGEDQITVWGFH
SDDKTQMKNLYGDSNPQKFTSSANGVTTHYVSQIGDFPNQTEDGGLPQSGRIVVDYMVQKPGKTGTIVY
QRGVLLPQKVWCASGRSKVIKGSLPLIGEADCLHEKYGGLNKSKPYYTGEHAKAIGNCPIWVKTPLKLA
NGTKYRPPAKLLKERGFFGAIAGFLEGGWEGMIAGWHGYTSHGAHGVAVAADLKSTQEAINKITKNLNS
LSELEVKNLQRLSGAMDELHNEILELDEKVDDLRADTISSQIELAVLLSNEGIINSEDEHLLALERKLK
KMLGPSAVDIGNGCFETKHKCNQTCLDRIAAGTFNAGEFSLPTFDSLNITAHHHHHH SEQ ID NO 104: UFV180400
MKAIIVLLMVVTSNADRICTGITSSNSPHVVKTATQGEVNVTGVIPLTTTPTKSHFANLKGTKTRGKLC
PNCLNCTDLDVALGRPMCMGTIPSAKASILHEVRPVTSGCFPIMHDRTKIRQLPNLLRGYENIRLSTHN
VINAERAPGGPYRLGTSGSCPNVTSRNGFFATMAWAVPRDNKTATNPLTVEVPYICTKGEDQITVWGFH
SDDKTQMKNLYGDSNPQQFTSSANGVTTIYVSQIGDFPNQTEDGGLPQSGRIVVDYMVQKPGKTGTIVY
QRGVLLPQKVWCASGRSKVIKGSLPLIGEADCLHEKYGGLNKSKPYYTGEHAKAIGNCPIWVKTPLKLA
NGTKYRPPAKLLKERGFFGAIAGFEGMIAGWIGYTSHGAHGVAVAADLKSTQEAINKITKNLNSLSELE
VKNLQRLSGAMDELHNEILELDEKVDDLRADTISSQIELRVLLSNEGIINSEDEILLALERKLKKMLGP
SAVDIGNGCFETKHKCNQTCLDRIAAGTFNAGEFSLPTFDSLNITASGSLVPSGSLPETGGGSHHHHHH SEQ ID NO 105: UFV180571
MKAIIVLLMVVTSNADRICTGITSSNSPHVVKTATQGEVNVTGVIPLTTTPTKSYFANLKGTRTRGKLC
PDCLNCTDLDVALGRPMCVGTTPSAKASILHEVKPVTSGCFPIMHDRTKIRQLPNLLRGYENIRLSTQN
VIDAEKAPGGPYRLGTSGSCPNATSKSGFFATMAWAVPKDNNKATNPLTVEVPYICTEGEDQITVWGF
HSDDKTQMKNLYGDSNPQKFTSSANGVTTHYVSQIGSFPDQTEDGGLPQSGRIVVDYMMQKPGKTGTIV -continued

---
SEQUENCES
---

```
YQRGVLLPQKVWCASGRSKVIKGSLPLIGEADCLHEKYGGLNKSKPYYTGEHAKAIGNCPIWVKTPLKL
ANGTKYRPPAKLLKERGFFGAIAGFLEGGWEGMIAGWHGYTSHGAHGVAVAADLKSTQEAINKITKNLN
SLSELEVKNLQRLSGAMDELHNEILELDEKVDDLRADTISSQIELAVLLSNEGIINSEDEHLLALERKL
KKMLGPSAVEIGNGCFETKHKCNQTCLDRIAAGTFNAGEFSLPTFDSLNITAHHHHHH

SEQ ID NO 106: UFV180570
MKAIIVLLMVVTSNADRICTGITSSNSPHVVKTATQGEVNVTGVIPLTTTPTKSYFANLKGTRTRGKLC
PDCLNCTDLDVALGRPMCVGTTPSAKASILHEVKPVTSGCFPIMHDRTKIRQLPNLLRGYENIRLSTQN
VIDAEKAPGGPYRLGTSGSCPNATSKSGFFATMAWAVPKDNNKNATNPLTVEVPYICTEGEDQITVWGF
HSDDKTQMKNLYGDSNPQQFTSSANGVTTIYVSQIGSFPDQTEDGGLPQSGRIVVDYMMQKPGKTGTIV
YQRGVLLPQKVWCASGRSKVIKGSLPLIGEADCLHEKYGGLNKSKPYYTGEHAKAIGNCPIWVKTPLKL
ANGTKYRPPAKLLKERGFFGAIAGFEGMIAGWIGYTSHGAHGVAVAADLKSTQEAINKITKNLNSLSEL
EVKNLQRLSGAMDELHNEILELDEKVDDLRADTISSQIELRVLLSNEGIINSEDEILLALERKLKKMLG
PSAVEIGNGCFETKHKCNQTCLDRIAAGTFNAGEFSLPTFDSLNITASGSLVPSGSLPETGGGSHHHHH
H

SEQ ID NO 107: UFV190909
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHVRLSTHN
VINAEGAPGGPYKIGTSGSCPNITNGNGFFATMAWAVPDKNKTATNPLTIEVPYVCTEGEDQITVWGFH
SDNETQMAKLYGDSKPQKFTSSANGVTTHYVSQIGGFPNQTEDGGLPQSGRIVVDYMVQKSGKTGTITY
QRGILLPQKVWCASGRSKVIKGSLPLIGEADCLHEKYGGLNKSKPYYTGEHAKAIGNCPIWVKTPLKLA
NGTKYRPPAKLLKERGFFGAIAGFLEGGWEGMIAGWHGYTSHGAHGVAVAADLKSTQEAINKITKNLNS
LSELEVKNLQRLSGAMDELHNEILELDEKVDDLRADTISSQIELAVLLSNEGIINSEDEHLLALERKLK
KMLGPSAVEIGNGCFETKHKCNQTCLDKIAAGTFDAGEFSLPTFDSLNITAHHHHHH

SEQ ID NO 108: UFV190521
MKAIIVLLMVVTSNADRICTGITSSNSPHVVKTATQGEVNVTGVIPLTTTPTKSHFANLKGTETRGKLC
PKCLNCTDLDVALGRPKCTGKIPSARVSILHEVRPVTSGCFPIMHDRTKIRQLPNLLRGYEHVRLSTHN
VINAEGAPGGPYKIGTSGSCPNITNGNGFFATMAWAVPDKNKTATNPLTIEVPYVCTEGEDQITVWGFH
SDNETQMAKLYGDSKPQQFTSSANGVTTIYVSQIGGFPNQTEDGGLPQSGRIVVDYMVQKSGKTGTITY
QRGILLPQKVWCASGRSKVIKGSLPLIGEADCLHEKYGGLNKSKPYYTGEHAKAIGNCPIWVKTPLKLA
NGTKYRPPAKLLKERGFFGAIAGFLEGGWEGMIAGWIGYTSHGAHGVAVAADLKSTQEAINKITKNLNS
LSELEVKNLQRLSGAMDELHNEILELDEKVDDLRADTISSQIELRVLLSNEGIINSEDEILLALERKLK
KMLGPSAVEIGNGCFETKHKCNQTCLDKIAAGTFDAGEFSLPTFDSLNITASGSLPETGGGSHHHHHH
```

---
SEQUENCE LISTING
---

```
<160> NUMBER OF SEQ ID NOS: 108

<210> SEQ ID NO 1
<211> LENGTH: 585
<212> TYPE: PRT
<213> ORGANISM: Artificial Sequence
<220> FEATURE:
<223> OTHER INFORMATION: B/Brisbane/60/08

<400> SEQUENCE: 1

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125
```

```
Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
```

-continued

```
545             550             555             560

Ala Val Thr Leu Met Ile Ala Ile Phe Val Val Tyr Met Val Ser Arg
            565                 570             575

Asp Asn Val Ser Cys Ser Ile Cys Leu
        580                 585

<210> SEQ ID NO 2
<211> LENGTH: 535
<212> TYPE: PRT
<213> ORGANISM: Artificial Sequence
<220> FEATURE:
<223> OTHER INFORMATION: UFV180846

<400> SEQUENCE: 2

Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
        35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
        115             120             125

Tyr Glu His Ile Arg Leu Ser Asn His Thr Val Ile Asn Ala Thr Asn
        130             135             140

Ala Pro Gly Gly Pro Tyr Asn Ile Thr Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
        210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
            245             250             255

Glu Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
        275             280             285

Trp Cys Ala Ser Gly Arg Ser Lys Val Ile Lys Gly Ser Leu Pro Leu
    290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
```

-continued

```
                  325               330               335
Pro Ile Trp Val Lys Thr Pro Leu Lys Leu Ala Asn Gly Thr Lys Tyr
          340               345               350
Arg Pro Pro Ala Lys Leu Leu Lys Glu Gln Gly Phe Phe Gly Ala Ile
          355               360               365
Ala Gly Phe Glu Gly Met Ile Ala Gly Trp Ile Gly Tyr Thr Ser His
          370               375               380
Gly Ala His Gly Val Ala Val Ala Ala Asp Leu Lys Ser Thr Gln Glu
385               390               395               400
Ala Ile Asn Lys Ile Thr Lys Asn Leu Asn Ser Leu Ser Glu Leu Glu
              405               410               415
Val Lys Asn Leu Gln Arg Leu Ser Gly Ala Met Asp Glu Leu His Asn
              420               425               430
Glu Ile Leu Glu Leu Asp Glu Lys Val Asp Asp Leu Arg Ala Asp Thr
              435               440               445
Ile Ser Ser Gln Ile Glu Leu Arg Val Leu Leu Ser Asn Glu Gly Ile
          450               455               460
Ile Asn Ser Glu Asp Glu Ile Leu Leu Ala Leu Glu Arg Lys Leu Lys
465               470               475               480
Lys Met Leu Gly Pro Ser Ala Val Glu Ile Gly Asn Gly Cys Phe Glu
              485               490               495
Thr Lys His Lys Cys Asn Gln Thr Cys Leu Asp Arg Ile Ala Ala Gly
          500               505               510
Thr Phe Asp Ala Gly Glu Phe Ser Leu Pro Thr Phe Asp Ser Leu Asn
          515               520               525
Ile Thr Ala Glu Pro Glu Ala
          530               535
```

```
<210> SEQ ID NO 3
<211> LENGTH: 614
<212> TYPE: PRT
<213> ORGANISM: Artificial Sequence
<220> FEATURE:
<223> OTHER INFORMATION: UFV170090

<400> SEQUENCE: 3

Met Lys Ala Ile Ile Val Leu Leu Met Val Val Thr Ser Asn Ala Asp
1               5                10                15
Arg Ile Cys Thr Gly Ile Thr Ser Ser Asn Ser Pro His Val Val Lys
              20                25                30
Thr Ala Thr Gln Gly Glu Val Asn Val Thr Gly Val Ile Pro Leu Thr
          35                40                45
Thr Thr Pro Thr Lys Ser His Phe Ala Asn Leu Lys Gly Thr Glu Thr
          50                55                60
Arg Gly Lys Leu Cys Pro Lys Cys Leu Asn Cys Thr Asp Leu Asp Val
65                70                75                80
Ala Leu Gly Arg Pro Lys Cys Thr Gly Lys Ile Pro Ser Ala Arg Val
              85                90                95
Ser Ile Leu His Glu Val Arg Pro Val Thr Ser Gly Cys Phe Pro Ile
              100               105               110
Met His Asp Arg Thr Lys Ile Arg Gln Leu Pro Asn Leu Leu Arg Gly
          115               120               125
Tyr Glu His Ile Arg Leu Ser Thr His Asn Val Ile Asn Ala Glu Asn
          130               135               140
Ala Pro Gly Gly Pro Tyr Lys Ile Gly Thr Ser Gly Ser Cys Pro Asn
```

-continued

```
145             150             155             160

Ile Thr Asn Gly Asn Gly Phe Phe Ala Thr Met Ala Trp Ala Val Pro
                165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
            210             215             220

Pro Gln Lys Phe Thr Ser Ser Ala Asn Gly Val Thr Thr His Tyr Val
225             230             235             240

Ser Gln Ile Gly Gly Phe Pro Asn Gln Thr Glu Asp Gly Gly Leu Pro
                245             250             255

Gln Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
            275             280             285

Trp Cys Ala Ser Gly Arg Ser Lys Val Ile Lys Gly Ser Leu Pro Leu
            290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
                325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
            355             360             365

Ala Gly Phe Leu Glu Gly Gly Trp Glu Gly Met Ile Ala Gly Trp His
370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
                405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
            435             440             445

Leu Arg Ala Asp Thr Ile Ser Ser Gln Ile Glu Leu Ala Val Leu Leu
            450             455             460

Ser Asn Glu Gly Ile Ile Asn Ser Glu Asp Glu His Leu Leu Ala Leu
465             470             475             480

Glu Arg Lys Leu Lys Lys Met Leu Gly Pro Ser Ala Val Glu Ile Gly
                485             490             495

Asn Gly Cys Phe Glu Thr Lys His Lys Cys Asn Gln Thr Cys Leu Asp
            500             505             510

Arg Ile Ala Ala Gly Thr Phe Asp Ala Gly Glu Phe Ser Leu Pro Thr
            515             520             525

Phe Asp Ser Leu Asn Ile Thr Ala Ser Gly Ser Leu Val Pro Arg Gly
            530             535             540

Ser Gly Ser Gly Tyr Ile Pro Glu Ala Pro Arg Asp Gly Gln Ala Tyr
545             550             555             560

Val Arg Lys Asp Gly Glu Trp Val Leu Leu Ser Thr Phe Leu Gly Gly
                565             570             575
```

```
Ser Leu Pro Glu Thr Gly Gly Gly Ser Asp Tyr Lys Asp Asp Asp Asp
            580                     585                 590

Lys Gly Gly Gly Gly Ser Gly Gly Gly Gly Ser Gly Gly Gly Gly Ser
        595                     600                     605

His His His His His His
    610
```

```
<210> SEQ ID NO 4
<211> LENGTH: 614
<212> TYPE: PRT
<213> ORGANISM: Artificial Sequence
<220> FEATURE:
<223> OTHER INFORMATION: UFV171700

<400> SEQUENCE: 4
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
            85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
            245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320
```

```
Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Met Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
            565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
            595                 600                 605

His His His His His His
    610

<210> SEQ ID NO 5
<211> LENGTH: 614
<212> TYPE: PRT
<213> ORGANISM: Artificial Sequence
<220> FEATURE:
<223> OTHER INFORMATION: UFV171701

<400> SEQUENCE: 5

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60
```

```
Arg Gly Lys Leu Cys Pro Lys Cys Leu Asn Cys Thr Asp Leu Asp Val
65              70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu His Ile Arg Leu Ser Thr His Asn Val Ile Asn Ala Glu Asn
            130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Leu Val Leu Leu
            450                 455                 460

Ser Asn Glu Gly Ile Ile Asn Ser Glu Asp Glu His Leu Leu Ala Leu
465                 470                 475                 480
```

-continued

```
Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Gly Ser Gly Gly Gly Gly Ser
                595                 600                 605

His His His His His His
    610

<210> SEQ ID NO 6
<211> LENGTH: 614
<212> TYPE: PRT
<213> ORGANISM: Artificial Sequence
<220> FEATURE:
<223> OTHER INFORMATION: UFV171702

<400> SEQUENCE: 6

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220
```

-continued

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Trp Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
        595                 600                 605

His His His His His His
    610

<210> SEQ ID NO 7
<211> LENGTH: 614
<212> TYPE: PRT

-continued

```
<213> ORGANISM: Artificial Sequence
<220> FEATURE:
<223> OTHER INFORMATION: UFV171703

<400> SEQUENCE: 7

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
            130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
```

-continued

```
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Tyr Val Leu Leu
        450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ser Gly Ser Leu Val Pro Arg Gly
        530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
                595                 600                 605

His His His His His His
        610
```

```
<210> SEQ ID NO 8
<211> LENGTH: 614
<212> TYPE: PRT
<213> ORGANISM: Artificial Sequence
<220> FEATURE:
<223> OTHER INFORMATION: UFV171741

<400> SEQUENCE: 8

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
```

```
            130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Arg Val Leu Leu
        450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ser Gly Ser Leu Val Pro Arg Gly
        530                 535                 540

Ser Gly Ser Gly Tyr Ile Pro Glu Ala Pro Arg Asp Gly Gln Ala Tyr
545                 550                 555                 560
```

-continued

```
Val Arg Lys Asp Gly Glu Trp Val Leu Leu Ser Thr Phe Leu Gly Gly
            565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
            595                 600                 605

His His His His His His
            610

<210> SEQ ID NO 9
<211> LENGTH: 614
<212> TYPE: PRT
<213> ORGANISM: Artificial Sequence
<220> FEATURE:
<223> OTHER INFORMATION: UFV170519

<400> SEQUENCE: 9

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
            50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
            85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
            130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Gln Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
            245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300
```

-continued

```
Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
            565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
        595                 600                 605

His His His His His His
    610
```

```
<210> SEQ ID NO 10
<211> LENGTH: 614
<212> TYPE: PRT
<213> ORGANISM: Artificial Sequence
<220> FEATURE:
<223> OTHER INFORMATION: UFV170520

<400> SEQUENCE: 10
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45
```

-continued

```
Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
                85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
        115             120             125

Tyr Glu His Ile Arg Leu Ser Thr His Asn Val Ile Asn Ala Glu Asn
    130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
    210             215             220

Pro Gln Asn Phe Thr Ser Ser Ala Asn Gly Val Thr Thr His Tyr Val
225             230             235             240

Ser Gln Ile Gly Gly Phe Pro Asn Gln Thr Glu Asp Gly Gly Leu Pro
            245             250             255

Gln Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
    275             280             285

Trp Cys Ala Ser Gly Arg Ser Lys Val Ile Lys Gly Ser Leu Pro Leu
    290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
            325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
        355             360             365

Ala Gly Phe Leu Glu Gly Gly Trp Glu Gly Met Ile Ala Gly Trp His
    370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
        420             425             430

Asp Glu Leu His Asn Glu Ile Leu Glu Leu Asp Glu Lys Val Asp Asp
        435             440             445

Leu Arg Ala Asp Thr Ile Ser Ser Gln Ile Glu Leu Ala Val Leu Leu
    450             455             460
```

```
Ser Asn Glu Gly Ile Ile Asn Ser Glu Asp Glu His Leu Leu Ala Leu
465             470             475             480

Glu Arg Lys Leu Lys Lys Met Leu Gly Pro Ser Ala Val Glu Ile Gly
            485             490             495

Asn Gly Cys Phe Glu Thr Lys His Lys Cys Asn Gln Thr Cys Leu Asp
            500             505             510

Arg Ile Ala Ala Gly Thr Phe Asp Ala Gly Glu Phe Ser Leu Pro Thr
            515             520             525

Phe Asp Ser Leu Asn Ile Thr Ala Ser Gly Ser Leu Val Pro Arg Gly
            530             535             540

Ser Gly Ser Gly Tyr Ile Pro Glu Ala Pro Arg Asp Gly Gln Ala Tyr
545             550             555             560

Val Arg Lys Asp Gly Glu Trp Val Leu Leu Ser Thr Phe Leu Gly Gly
            565             570             575

Ser Leu Pro Glu Thr Gly Gly Gly Ser Asp Tyr Lys Asp Asp Asp Asp
            580             585             590

Lys Gly Gly Gly Gly Ser Gly Gly Gly Ser Gly Gly Gly Ser
            595             600             605

His His His His His His
    610
```

```
<210> SEQ ID NO 11
<211> LENGTH: 614
<212> TYPE: PRT
<213> ORGANISM: Artificial Sequence
<220> FEATURE:
<223> OTHER INFORMATION: UFV170521

<400> SEQUENCE: 11

Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
    130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205
```

```
His Ser Asp Asn Glu Thr Gln Met Ala Lys Leu Tyr Gly Asp Ser Lys
    210                 215                 220

Pro Gln Phe Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
                595                 600                 605

His His His His His His
    610
```

<210> SEQ ID NO 12
<211> LENGTH: 614
<212> TYPE: PRT
<213> ORGANISM: Artificial Sequence
<220> FEATURE:
<223> OTHER INFORMATION: UFV170522

<400> SEQUENCE: 12

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Ile Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His

```
            370              375              380
Gly Tyr Thr Ser His Gly Ala His Gly Val Ala Val Ala Ala Asp Leu
385              390              395              400

Lys Ser Thr Gln Glu Ala Ile Asn Lys Ile Thr Lys Asn Leu Asn Ser
            405              410              415

Leu Ser Glu Leu Glu Val Lys Asn Leu Gln Arg Leu Ser Gly Ala Met
            420              425              430

Asp Glu Leu His Asn Glu Ile Leu Glu Leu Asp Glu Lys Val Asp Asp
            435              440              445

Leu Arg Ala Asp Thr Ile Ser Ser Gln Ile Glu Leu Ala Val Leu Leu
            450              455              460

Ser Asn Glu Gly Ile Ile Asn Ser Glu Asp Glu His Leu Leu Ala Leu
465              470              475              480

Glu Arg Lys Leu Lys Lys Met Leu Gly Pro Ser Ala Val Glu Ile Gly
            485              490              495

Asn Gly Cys Phe Glu Thr Lys His Lys Cys Asn Gln Thr Cys Leu Asp
            500              505              510

Arg Ile Ala Ala Gly Thr Phe Asp Ala Gly Glu Phe Ser Leu Pro Thr
            515              520              525

Phe Asp Ser Leu Asn Ile Thr Ala Ser Gly Ser Leu Val Pro Arg Gly
            530              535              540

Ser Gly Ser Gly Tyr Ile Pro Glu Ala Pro Arg Asp Gly Gln Ala Tyr
545              550              555              560

Val Arg Lys Asp Gly Glu Trp Val Leu Leu Ser Thr Phe Leu Gly Gly
            565              570              575

Ser Leu Pro Glu Thr Gly Gly Gly Ser Asp Tyr Lys Asp Asp Asp Asp
            580              585              590

Lys Gly Gly Gly Gly Ser Gly Gly Gly Ser Gly Gly Gly Gly Ser
            595              600              605

His His His His His His
    610
```

```
<210> SEQ ID NO 13
<211> LENGTH: 614
<212> TYPE: PRT
<213> ORGANISM: Artificial Sequence
<220> FEATURE:
<223> OTHER INFORMATION: UFV170523

<400> SEQUENCE: 13

Met Lys Ala Ile Ile Val Leu Leu Met Val Val Thr Ser Asn Ala Asp
1               5               10               15

Arg Ile Cys Thr Gly Ile Thr Ser Ser Asn Ser Pro His Val Val Lys
            20               25               30

Thr Ala Thr Gln Gly Glu Val Asn Val Thr Gly Val Ile Pro Leu Thr
            35               40               45

Thr Thr Pro Thr Lys Ser His Phe Ala Asn Leu Lys Gly Thr Glu Thr
            50               55               60

Arg Gly Lys Leu Cys Pro Lys Cys Leu Asn Cys Thr Asp Leu Asp Val
65               70               75               80

Ala Leu Gly Arg Pro Lys Cys Thr Gly Lys Ile Pro Ser Ala Arg Val
            85               90               95

Ser Ile Leu His Glu Val Arg Pro Val Thr Ser Gly Cys Phe Pro Ile
            100              105              110

Met His Asp Arg Thr Lys Ile Arg Gln Leu Pro Asn Leu Leu Arg Gly
```

-continued

```
                115             120             125
Tyr Glu His Ile Arg Leu Ser Thr His Asn Val Ile Asn Ala Glu Asn
    130             135             140
Ala Pro Gly Gly Pro Tyr Lys Ile Gly Thr Ser Gly Ser Cys Pro Asn
145             150             155             160
Ile Thr Asn Gly Asn Gly Phe Phe Ala Thr Met Ala Trp Ala Val Pro
            165             170             175
Lys Asn Asp Lys Asn Lys Thr Ala Thr Asn Pro Leu Thr Ile Glu Val
            180             185             190
Pro Tyr Ile Cys Thr Glu Gly Glu Asp Gln Ile Thr Val Trp Gly Phe
            195             200             205
His Ser Asp Asn Glu Thr Gln Met Ala Lys Leu Tyr Gly Asp Ser Lys
            210             215             220
Pro Gln Tyr Phe Thr Ser Ser Ala Asn Gly Val Thr Thr His Tyr Val
225             230             235             240
Ser Gln Ile Gly Gly Phe Pro Asn Gln Thr Glu Asp Gly Gly Leu Pro
            245             250             255
Gln Ser Gly Arg Ile Val Val Asp Tyr Met Val Gln Lys Ser Gly Lys
            260             265             270
Thr Gly Thr Ile Thr Tyr Gln Arg Gly Ile Leu Leu Pro Gln Lys Val
            275             280             285
Trp Cys Ala Ser Gly Arg Ser Lys Val Ile Lys Gly Ser Leu Pro Leu
    290             295             300
Ile Gly Glu Ala Asp Cys Leu His Glu Lys Tyr Gly Gly Leu Asn Lys
305             310             315             320
Ser Lys Pro Tyr Tyr Thr Gly Glu His Ala Lys Ala Ile Gly Asn Cys
            325             330             335
Pro Ile Trp Val Lys Thr Pro Leu Lys Leu Ala Asn Gly Thr Lys Tyr
            340             345             350
Arg Pro Pro Ala Lys Leu Leu Lys Glu Arg Gly Phe Phe Gly Ala Ile
            355             360             365
Ala Gly Phe Leu Glu Gly Gly Trp Glu Gly Met Ile Ala Gly Trp His
    370             375             380
Gly Tyr Thr Ser His Gly Ala His Gly Val Ala Val Ala Ala Asp Leu
385             390             395             400
Lys Ser Thr Gln Glu Ala Ile Asn Lys Ile Thr Lys Asn Leu Asn Ser
            405             410             415
Leu Ser Glu Leu Glu Val Lys Asn Leu Gln Arg Leu Ser Gly Ala Met
            420             425             430
Asp Glu Leu His Asn Glu Ile Leu Glu Leu Asp Glu Lys Val Asp Asp
            435             440             445
Leu Arg Ala Asp Thr Ile Ser Ser Gln Ile Glu Leu Ala Val Leu Leu
    450             455             460
Ser Asn Glu Gly Ile Ile Asn Ser Glu Asp Glu His Leu Leu Ala Leu
465             470             475             480
Glu Arg Lys Leu Lys Lys Met Leu Gly Pro Ser Ala Val Glu Ile Gly
            485             490             495
Asn Gly Cys Phe Glu Thr Lys His Lys Cys Asn Gln Thr Cys Leu Asp
            500             505             510
Arg Ile Ala Ala Gly Thr Phe Asp Ala Gly Glu Phe Ser Leu Pro Thr
            515             520             525
Phe Asp Ser Leu Asn Ile Thr Ala Ser Gly Ser Leu Val Pro Arg Gly
    530             535             540
```

```
Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
        595                 600                 605

His His His His His His
    610
```

```
<210> SEQ ID NO 14
<211> LENGTH: 614
<212> TYPE: PRT
<213> ORGANISM: Artificial Sequence
<220> FEATURE:
<223> OTHER INFORMATION: UFV170515

<400> SEQUENCE: 14
```

```
Met Lys Ala Ile Ile Val Leu Leu Met Val Val Thr Ser Asn Ala Asp
1                 5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr Asn Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
        275                 280                 285
```

-continued

```
Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
            565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
        595                 600                 605

His His His His His His
    610
```

```
<210> SEQ ID NO 15
<211> LENGTH: 614
<212> TYPE: PRT
<213> ORGANISM: Artificial Sequence
<220> FEATURE:
<223> OTHER INFORMATION: UFV170516
```

```
<400> SEQUENCE: 15
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
        20                  25                  30
```

-continued

```
Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
            85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr Gln Tyr Val
225                 230                 235                 240

Ser Gln Ile Gly Gly Phe Pro Asn Gln Thr Glu Asp Gly Gly Leu Pro
            245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
    275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445
```

-continued

```
Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
        595                 600                 605

His His His His His His
    610
```

```
<210> SEQ ID NO 16
<211> LENGTH: 614
<212> TYPE: PRT
<213> ORGANISM: Artificial Sequence
<220> FEATURE:
<223> OTHER INFORMATION: UFV1705217

<400> SEQUENCE: 16

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190
```

```
Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Ser Asp Tyr Lys Asp Asp Asp Asp
                580                 585                 590

Lys Gly Gly Gly Gly Ser Gly Gly Gly Ser Gly Gly Gly Gly Ser
        595                 600                 605

His His His His His His
```

-continued

610

<210> SEQ ID NO 17
<211> LENGTH: 614
<212> TYPE: PRT
<213> ORGANISM: Artificial Sequence
<220> FEATURE:
<223> OTHER INFORMATION: UFV170518

<400> SEQUENCE: 17

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr Phe Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile

```
            355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
            595                 600                 605

His His His His His His
    610
```

```
<210> SEQ ID NO 18
<211> LENGTH: 614
<212> TYPE: PRT
<213> ORGANISM: Artificial Sequence
<220> FEATURE:
<223> OTHER INFORMATION: UFV170524

<400> SEQUENCE: 18

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
```

```
                100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Asn Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525
```

-continued

```
Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
        595                 600                 605

His His His His His His
    610

<210> SEQ ID NO 19
<211> LENGTH: 614
<212> TYPE: PRT
<213> ORGANISM: Artificial Sequence
<220> FEATURE:
<223> OTHER INFORMATION: UFV170525

<400> SEQUENCE: 19

Met Lys Ala Ile Ile Val Leu Leu Met Val Val Thr Ser Asn Ala Asp
1                   5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270
```

-continued

```
Thr Gly Thr Ile Thr Tyr Gln Arg Gly Ile Leu Leu Pro Gln Lys Val
    275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
                595                 600                 605

His His His His His His
    610
```

```
<210> SEQ ID NO 20
<211> LENGTH: 614
<212> TYPE: PRT
<213> ORGANISM: Artificial Sequence
<220> FEATURE:
<223> OTHER INFORMATION: UFV170541

<400> SEQUENCE: 20
```

```
Met Lys Ala Ile Ile Val Leu Leu Met Val Val Thr Ser Asn Ala Asp
1               5                   10                  15
```

-continued

```
Arg Ile Cys Thr Gly Ile Thr Ser Ser Asn Ser Pro His Val Val Lys
        20                  25              30

Thr Ala Thr Gln Gly Glu Val Asn Val Thr Gly Val Ile Pro Leu Thr
        35                  40              45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Trp
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430
```

```
Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
        450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ser Gly Ser Leu Val Pro Arg Gly
        530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
        595                 600                 605

His His His His His His
        610

<210> SEQ ID NO 21
<211> LENGTH: 614
<212> TYPE: PRT
<213> ORGANISM: Artificial Sequence
<220> FEATURE:
<223> OTHER INFORMATION: UFV170542

<400> SEQUENCE: 21

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175
```

```
Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Phe
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
            450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
            530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
```

-continued

```
               595                 600                 605
His His His His His His
    610

<210> SEQ ID NO 22
<211> LENGTH: 614
<212> TYPE: PRT
<213> ORGANISM: Artificial Sequence
<220> FEATURE:
<223> OTHER INFORMATION: UFV170543

<400> SEQUENCE: 22

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
```

```
              340              345              350

Arg Pro Pro Ala Lys Leu Leu Lys Glu Arg Gly Phe Phe Gly Ala Ile
         355              360              365

Ala Gly Phe Leu Glu Gly Gly Trp Glu Gly Met Ile Ala Gly Trp Asn
    370              375              380

Gly Tyr Thr Ser His Gly Ala His Gly Val Ala Val Ala Ala Asp Leu
385              390              395              400

Lys Ser Thr Gln Glu Ala Ile Asn Lys Ile Thr Lys Asn Leu Asn Ser
             405              410              415

Leu Ser Glu Leu Glu Val Lys Asn Leu Gln Arg Leu Ser Gly Ala Met
             420              425              430

Asp Glu Leu His Asn Glu Ile Leu Glu Leu Asp Glu Lys Val Asp Asp
         435              440              445

Leu Arg Ala Asp Thr Ile Ser Ser Gln Ile Glu Leu Ala Val Leu Leu
    450              455              460

Ser Asn Glu Gly Ile Ile Asn Ser Glu Asp Glu His Leu Leu Ala Leu
465              470              475              480

Glu Arg Lys Leu Lys Lys Met Leu Gly Pro Ser Ala Val Glu Ile Gly
             485              490              495

Asn Gly Cys Phe Glu Thr Lys His Lys Cys Asn Gln Thr Cys Leu Asp
         500              505              510

Arg Ile Ala Ala Gly Thr Phe Asp Ala Gly Glu Phe Ser Leu Pro Thr
         515              520              525

Phe Asp Ser Leu Asn Ile Thr Ala Ser Gly Ser Leu Val Pro Arg Gly
    530              535              540

Ser Gly Ser Gly Tyr Ile Pro Glu Ala Pro Arg Asp Gly Gln Ala Tyr
545              550              555              560

Val Arg Lys Asp Gly Glu Trp Val Leu Leu Ser Thr Phe Leu Gly Gly
             565              570              575

Ser Leu Pro Glu Thr Gly Gly Gly Ser Asp Tyr Lys Asp Asp Asp Asp
             580              585              590

Lys Gly Gly Gly Gly Ser Gly Gly Gly Gly Ser Gly Gly Gly Gly Ser
         595              600              605

His His His His His His
    610
```

<210> SEQ ID NO 23
<211> LENGTH: 614
<212> TYPE: PRT
<213> ORGANISM: Artificial Sequence
<220> FEATURE:
<223> OTHER INFORMATION: UFV170544

<400> SEQUENCE: 23

```
Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
             20              25              30

Thr Ala Thr Gln Gly Glu Val Asn Val Thr Gly Val Ile Pro Leu Thr
         35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
```

```
                    85               90               95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
            130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
            210             215             220

Pro Gln Lys Phe Thr Ser Ser Ala Asn Gly Val Thr Thr His Tyr Val
225             230             235             240

Ser Gln Ile Gly Gly Phe Pro Asn Gln Thr Glu Asp Gly Gly Leu Pro
            245             250             255

Gln Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
            275             280             285

Trp Cys Ala Ser Gly Arg Ser Lys Val Ile Lys Gly Ser Leu Pro Leu
            290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
            325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
            355             360             365

Ala Gly Phe Leu Glu Gly Gly Trp Glu Gly Met Ile Ala Gly Trp Gln
            370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
            435             440             445

Leu Arg Ala Asp Thr Ile Ser Ser Gln Ile Glu Leu Ala Val Leu Leu
            450             455             460

Ser Asn Glu Gly Ile Ile Asn Ser Glu Asp Glu His Leu Leu Ala Leu
465             470             475             480

Glu Arg Lys Leu Lys Lys Met Leu Gly Pro Ser Ala Val Glu Ile Gly
            485             490             495

Asn Gly Cys Phe Glu Thr Lys His Lys Cys Asn Gln Thr Cys Leu Asp
            500             505             510
```

-continued

```
Arg Ile Ala Ala Gly Thr Phe Asp Ala Gly Glu Phe Ser Leu Pro Thr
    515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
                595                 600                 605

His His His His His His
    610
```

<210> SEQ ID NO 24
<211> LENGTH: 614
<212> TYPE: PRT
<213> ORGANISM: Artificial Sequence
<220> FEATURE:
<223> OTHER INFORMATION: UFV170545

<400> SEQUENCE: 24

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255
```

-continued

```
Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
            450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
            530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
            595                 600                 605

His His His His His His
    610
```

```
<210> SEQ ID NO 25
<211> LENGTH: 614
<212> TYPE: PRT
<213> ORGANISM: Artificial Sequence
<220> FEATURE:
<223> OTHER INFORMATION: UFV170546

<400> SEQUENCE: 25
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
    275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415
```

```
Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
            450                 455                 460

Ser Asn Glu Gly Ile Ile Asn Ser Glu Asp Glu Trp Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
            530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
            565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
            595                 600                 605

His His His His His His
    610

<210> SEQ ID NO 26
<211> LENGTH: 614
<212> TYPE: PRT
<213> ORGANISM: Artificial Sequence
<220> FEATURE:
<223> OTHER INFORMATION: UFV170547

<400> SEQUENCE: 26

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
            50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
            85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
            130                 135                 140

Ala Pro Gly Gly Pro Tyr Lys Ile Gly Thr Ser Gly Ser Cys Pro Asn
145                 150                 155                 160
```

```
Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
            450                 455                 460

Ser Asn Glu Gly Ile Ile Asn Ser Glu Asp Glu Phe Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
            530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
```

```
                580                 585                 590
Lys Gly Gly Gly Gly Ser Gly Gly Gly Gly Ser Gly Gly Gly Gly Ser
        595                 600                 605

His His His His His His
        610

<210> SEQ ID NO 27
<211> LENGTH: 614
<212> TYPE: PRT
<213> ORGANISM: Artificial Sequence
<220> FEATURE:
<223> OTHER INFORMATION: UFV170548

<400> SEQUENCE: 27

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
```

```
                      325                 330                 335
Pro Ile Trp Val Lys Thr Pro Leu Lys Leu Ala Asn Gly Thr Lys Tyr
              340                 345                 350
Arg Pro Pro Ala Lys Leu Leu Lys Glu Arg Gly Phe Phe Gly Ala Ile
              355                 360                 365
Ala Gly Phe Leu Glu Gly Gly Trp Glu Gly Met Ile Ala Gly Trp His
          370                 375                 380
Gly Tyr Thr Ser His Gly Ala His Gly Val Ala Val Ala Ala Asp Leu
385                 390                 395                 400
Lys Ser Thr Gln Glu Ala Ile Asn Lys Ile Thr Lys Asn Leu Asn Ser
              405                 410                 415
Leu Ser Glu Leu Glu Val Lys Asn Leu Gln Arg Leu Ser Gly Ala Met
              420                 425                 430
Asp Glu Leu His Asn Glu Ile Leu Glu Leu Asp Glu Lys Val Asp Asp
          435                 440                 445
Leu Arg Ala Asp Thr Ile Ser Ser Gln Ile Glu Leu Ala Val Leu Leu
          450                 455                 460
Ser Asn Glu Gly Ile Ile Asn Ser Glu Asp Glu Tyr Leu Leu Ala Leu
465                 470                 475                 480
Glu Arg Lys Leu Lys Lys Met Leu Gly Pro Ser Ala Val Glu Ile Gly
              485                 490                 495
Asn Gly Cys Phe Glu Thr Lys His Lys Cys Asn Gln Thr Cys Leu Asp
              500                 505                 510
Arg Ile Ala Ala Gly Thr Phe Asp Ala Gly Glu Phe Ser Leu Pro Thr
              515                 520                 525
Phe Asp Ser Leu Asn Ile Thr Ala Ser Gly Ser Leu Val Pro Arg Gly
          530                 535                 540
Ser Gly Ser Gly Tyr Ile Pro Glu Ala Pro Arg Asp Gly Gln Ala Tyr
545                 550                 555                 560
Val Arg Lys Asp Gly Glu Trp Val Leu Leu Ser Thr Phe Leu Gly Gly
              565                 570                 575
Ser Leu Pro Glu Thr Gly Gly Gly Ser Asp Tyr Lys Asp Asp Asp Asp
              580                 585                 590
Lys Gly Gly Gly Gly Ser Gly Gly Gly Ser Gly Gly Gly Gly Ser
              595                 600                 605
His His His His His His
      610
```

<210> SEQ ID NO 28
<211> LENGTH: 614
<212> TYPE: PRT
<213> ORGANISM: Artificial Sequence
<220> FEATURE:
<223> OTHER INFORMATION: UFV170549

<400> SEQUENCE: 28

```
Met Lys Ala Ile Ile Val Leu Leu Met Val Val Thr Ser Asn Ala Asp
1               5                   10                  15
Arg Ile Cys Thr Gly Ile Thr Ser Ser Asn Ser Pro His Val Val Lys
              20                  25                  30
Thr Ala Thr Gln Gly Glu Val Asn Val Thr Gly Val Ile Pro Leu Thr
          35                  40                  45
Thr Thr Pro Thr Lys Ser His Phe Ala Asn Leu Lys Gly Thr Glu Thr
      50                  55                  60
Arg Gly Lys Leu Cys Pro Lys Cys Leu Asn Cys Thr Asp Leu Asp Val
```

-continued

```
65                   70               75                80

Ala Leu Gly Arg Pro Lys Cys Thr Gly Lys Ile Pro Ser Ala Arg Val
             85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
        130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
        210             215             220

Pro Gln Lys Phe Thr Ser Ser Ala Asn Gly Val Thr Thr His Tyr Val
225             230             235             240

Ser Gln Ile Gly Gly Phe Pro Asn Gln Thr Glu Asp Gly Gly Leu Pro
            245             250             255

Gln Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
            275             280             285

Trp Cys Ala Ser Gly Arg Ser Lys Val Ile Lys Gly Ser Leu Pro Leu
        290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
            325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
            355             360             365

Ala Gly Phe Leu Glu Gly Gly Trp Glu Gly Met Ile Ala Gly Trp His
        370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
        435             440             445

Leu Arg Ala Asp Thr Ile Ser Ser Gln Ile Glu Leu Ala Val Leu Leu
        450             455             460

Ser Asn Glu Gly Ile Ile Asn Ser Glu Asp Glu Ile Leu Leu Ala Leu
465             470             475             480

Glu Arg Lys Leu Lys Lys Met Leu Gly Pro Ser Ala Val Glu Ile Gly
            485             490             495
```

```
Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
            530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
            595                 600                 605

His His His His His His
            610
```

```
<210> SEQ ID NO 29
<211> LENGTH: 614
<212> TYPE: PRT
<213> ORGANISM: Artificial Sequence
<220> FEATURE:
<223> OTHER INFORMATION: UFV170550

<400> SEQUENCE: 29
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240
```

-continued

```
Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
            450                 455                 460

Ser Asn Glu Gly Ile Ile Asn Ser Glu Asp Glu Asn Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
            530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
            595                 600                 605

His His His His His His
    610
```

```
<210> SEQ ID NO 30
<211> LENGTH: 614
<212> TYPE: PRT
<213> ORGANISM: Artificial Sequence
<220> FEATURE:
```

-continued

<223> OTHER INFORMATION: UFV170551

<400> SEQUENCE: 30

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400
```

```
Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu Gln Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
                595                 600                 605

His His His His His His
    610
```

<210> SEQ ID NO 31
<211> LENGTH: 614
<212> TYPE: PRT
<213> ORGANISM: Artificial Sequence
<220> FEATURE:
<223> OTHER INFORMATION: UFV170552

<400> SEQUENCE: 31

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu His Ile Arg Leu Ser Thr His Asn Val Ile Asn Ala Glu Asn
    130                 135                 140
```

-continued

```
Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Trp
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
        450                 455                 460

Ser Asn Glu Gly Ile Ile Asn Ser Glu Asp Glu Trp Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
        530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
```

-continued

```
                565                 570                 575
Ser Leu Pro Glu Thr Gly Gly Gly Ser Asp Tyr Lys Asp Asp Asp Asp
            580                 585                 590

Lys Gly Gly Gly Gly Ser Gly Gly Gly Gly Ser Gly Gly Gly Gly Ser
            595                 600                 605

His His His His His His
        610
```

```
<210> SEQ ID NO 32
<211> LENGTH: 614
<212> TYPE: PRT
<213> ORGANISM: Artificial Sequence
<220> FEATURE:
<223> OTHER INFORMATION: UFV170553

<400> SEQUENCE: 32

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
```

-continued

```
305                310                315                320
Ser Lys Pro Tyr Tyr Thr Gly Glu His Ala Lys Ala Ile Gly Asn Cys
              325                330                335

Pro Ile Trp Val Lys Thr Pro Leu Lys Leu Ala Asn Gly Thr Lys Tyr
              340                345                350

Arg Pro Pro Ala Lys Leu Leu Lys Glu Arg Gly Phe Phe Gly Ala Ile
          355                360                365

Ala Gly Phe Leu Glu Gly Gly Trp Glu Gly Met Ile Ala Gly Trp Trp
    370                375                380

Gly Tyr Thr Ser His Gly Ala His Gly Val Ala Val Ala Ala Asp Leu
385                390                395                400

Lys Ser Thr Gln Glu Ala Ile Asn Lys Ile Thr Lys Asn Leu Asn Ser
              405                410                415

Leu Ser Glu Leu Glu Val Lys Asn Leu Gln Arg Leu Ser Gly Ala Met
              420                425                430

Asp Glu Leu His Asn Glu Ile Leu Glu Leu Asp Glu Lys Val Asp Asp
          435                440                445

Leu Arg Ala Asp Thr Ile Ser Ser Gln Ile Glu Leu Ala Val Leu Leu
    450                455                460

Ser Asn Glu Gly Ile Ile Asn Ser Glu Asp Glu Phe Leu Leu Ala Leu
465                470                475                480

Glu Arg Lys Leu Lys Lys Met Leu Gly Pro Ser Ala Val Glu Ile Gly
              485                490                495

Asn Gly Cys Phe Glu Thr Lys His Lys Cys Asn Gln Thr Cys Leu Asp
          500                505                510

Arg Ile Ala Ala Gly Thr Phe Asp Ala Gly Glu Phe Ser Leu Pro Thr
          515                520                525

Phe Asp Ser Leu Asn Ile Thr Ala Ser Gly Ser Leu Val Pro Arg Gly
    530                535                540

Ser Gly Ser Gly Tyr Ile Pro Glu Ala Pro Arg Asp Gly Gln Ala Tyr
545                550                555                560

Val Arg Lys Asp Gly Glu Trp Val Leu Leu Ser Thr Phe Leu Gly Gly
              565                570                575

Ser Leu Pro Glu Thr Gly Gly Gly Ser Asp Tyr Lys Asp Asp Asp Asp
              580                585                590

Lys Gly Gly Gly Gly Ser Gly Gly Gly Ser Gly Gly Gly Gly Ser
          595                600                605

His His His His His His
    610
```

```
<210> SEQ ID NO 33
<211> LENGTH: 614
<212> TYPE: PRT
<213> ORGANISM: Artificial Sequence
<220> FEATURE:
<223> OTHER INFORMATION: UFV170554

<400> SEQUENCE: 33

Met Lys Ala Ile Ile Val Leu Leu Met Val Val Thr Ser Asn Ala Asp
1               5                10                15

Arg Ile Cys Thr Gly Ile Thr Ser Ser Asn Ser Pro His Val Val Lys
              20                25                30

Thr Ala Thr Gln Gly Glu Val Asn Val Thr Gly Val Ile Pro Leu Thr
          35                40                45

Thr Thr Pro Thr Lys Ser His Phe Ala Asn Leu Lys Gly Thr Glu Thr
```

-continued

```
          50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
                85              90              95

Ser Ile Leu His Glu Val Arg Pro Val Thr Ser Gly Cys Phe Pro Ile
                100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
        130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
                165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
        195             200             205

His Ser Asp Asn Glu Thr Gln Met Ala Lys Leu Tyr Gly Asp Ser Lys
        210             215             220

Pro Gln Lys Phe Thr Ser Ser Ala Asn Gly Val Thr Thr His Tyr Val
225             230             235             240

Ser Gln Ile Gly Gly Phe Pro Asn Gln Thr Glu Asp Gly Gly Leu Pro
                245             250             255

Gln Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
            275             280             285

Trp Cys Ala Ser Gly Arg Ser Lys Val Ile Lys Gly Ser Leu Pro Leu
        290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
                325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
            355             360             365

Ala Gly Phe Leu Glu Gly Gly Trp Glu Gly Met Ile Ala Gly Trp Phe
        370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
        435             440             445

Leu Arg Ala Asp Thr Ile Ser Ser Gln Ile Glu Leu Ala Val Leu Leu
    450             455             460

Ser Asn Glu Gly Ile Ile Asn Ser Glu Asp Glu Trp Leu Leu Ala Leu
465             470             475             480
```

```
Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ser Gly Ser Leu Val Pro Arg Gly
            530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
            595                 600                 605

His His His His His His
    610

<210> SEQ ID NO 34
<211> LENGTH: 614
<212> TYPE: PRT
<213> ORGANISM: Artificial Sequence
<220> FEATURE:
<223> OTHER INFORMATION: UFV170555

<400> SEQUENCE: 34

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220
```

-continued

```
Pro Gln Lys Phe Thr Ser Ser Ala Asn Gly Val Thr Thr His Tyr Val
225             230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Trp
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu Tyr Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
            565                 570                 575

Ser Leu Pro Glu Thr Gly Gly Ser Asp Tyr Lys Asp Asp Asp Asp
            580                 585                 590

Lys Gly Gly Gly Gly Ser Gly Gly Gly Ser Gly Gly Gly Gly Ser
            595                 600                 605

His His His His His His
    610
```

<210> SEQ ID NO 35
<211> LENGTH: 614

```
<212> TYPE: PRT
<213> ORGANISM: Artificial Sequence
<220> FEATURE:
<223> OTHER INFORMATION: UFV170556

<400> SEQUENCE: 35

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp Ile
        370                 375                 380
```

```
Gly Tyr Thr Ser His Gly Ala His Gly Val Ala Val Ala Ala Asp Leu
385             390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
        450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
        530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Ser Gly Gly Gly Gly Ser
            595                 600                 605

His His His His His His
        610
```

```
<210> SEQ ID NO 36
<211> LENGTH: 614
<212> TYPE: PRT
<213> ORGANISM: Artificial Sequence
<220> FEATURE:
<223> OTHER INFORMATION: UFV170557

<400> SEQUENCE: 36
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125
```

```
Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
    275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
    355                 360                 365

Ala Gly Phe Leu Glu Gly Gly Trp Glu Gly Met Ile Ala Gly Trp Asn
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
    435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu Asn Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ser Gly Ser Leu Val Pro Arg Gly
    530                 535                 540

Ser Gly Ser Gly Tyr Ile Pro Glu Ala Pro Arg Asp Gly Gln Ala Tyr
```

```
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
                580                 585                 590

Lys Gly Gly Gly Gly Ser Gly Gly Gly Gly Ser Gly Gly Gly Gly Ser
                595                 600                 605

His His His His His His
                610
```

```
<210> SEQ ID NO 37
<211> LENGTH: 614
<212> TYPE: PRT
<213> ORGANISM: Artificial Sequence
<220> FEATURE:
<223> OTHER INFORMATION: UFV170558

<400> SEQUENCE: 37

Met Lys Ala Ile Ile Val Leu Leu Met Val Val Thr Ser Asn Ala Asp
1                   5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Lys Ser His Phe Ala Asn Leu Lys Gly Thr Glu Thr
                50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu His Ile Arg Leu Ser Thr His Asn Val Ile Asn Ala Glu Asn
                130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asn Glu Thr Gln Met Ala Lys Leu Tyr Gly Asp Ser Lys
                210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
```

-continued

```
       290                 295                 300

Ile Gly Glu Ala Asp Cys Leu His Glu Lys Tyr Gly Gly Leu Asn Lys
305                     310                 315                 320

Ser Lys Pro Tyr Tyr Thr Gly Glu His Ala Lys Ala Ile Gly Asn Cys
                    325                 330                 335

Pro Ile Trp Val Lys Thr Pro Leu Lys Leu Ala Asn Gly Thr Lys Tyr
                    340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Gln
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
        450                 455                 460

Ser Asn Glu Gly Ile Ile Asn Ser Glu Asp Glu Gln Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
        530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
                565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Gly Ser Gly Gly Gly Gly Ser
            595                 600                 605

His His His His His His
    610
```

```
<210> SEQ ID NO 38
<211> LENGTH: 614
<212> TYPE: PRT
<213> ORGANISM: Artificial Sequence
<220> FEATURE:
<223> OTHER INFORMATION: UFV170559

<400> SEQUENCE: 38

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
```

-continued

```
             35                    40                    45

Thr Thr Pro Thr Lys Ser His Phe Ala Asn Leu Lys Gly Thr Glu Thr
    50                    55                    60

Arg Gly Lys Leu Cys Pro Lys Cys Leu Asn Cys Thr Asp Leu Asp Val
65                    70                    75                    80

Ala Leu Gly Arg Pro Lys Cys Thr Gly Lys Ile Pro Ser Ala Arg Val
                85                    90                    95

Ser Ile Leu His Glu Val Arg Pro Val Thr Ser Gly Cys Phe Pro Ile
            100                   105                   110

Met His Asp Arg Thr Lys Ile Arg Gln Leu Pro Asn Leu Leu Arg Gly
            115                   120                   125

Tyr Glu His Ile Arg Leu Ser Thr His Asn Val Ile Asn Ala Glu Asn
    130                   135                   140

Ala Pro Gly Gly Pro Tyr Lys Ile Gly Thr Ser Gly Ser Cys Pro Asn
145                   150                   155                   160

Ile Thr Asn Gly Asn Gly Phe Phe Ala Thr Met Ala Trp Ala Val Pro
                165                   170                   175

Lys Asn Asp Lys Asn Lys Thr Ala Thr Asn Pro Leu Thr Ile Glu Val
            180                   185                   190

Pro Tyr Ile Cys Thr Glu Gly Glu Asp Gln Ile Thr Val Trp Gly Phe
            195                   200                   205

His Ser Asp Asn Glu Thr Gln Met Ala Lys Leu Tyr Gly Asp Ser Lys
    210                   215                   220

Pro Gln Lys Phe Thr Ser Ser Ala Asn Gly Val Thr Thr His Tyr Val
225                   230                   235                   240

Ser Gln Ile Gly Gly Phe Pro Asn Gln Thr Glu Asp Gly Gly Leu Pro
                245                   250                   255

Gln Ser Gly Arg Ile Val Val Asp Tyr Met Val Gln Lys Ser Gly Lys
            260                   265                   270

Thr Gly Thr Ile Thr Tyr Gln Arg Gly Ile Leu Leu Pro Gln Lys Val
            275                   280                   285

Trp Cys Ala Ser Gly Arg Ser Lys Val Ile Lys Gly Ser Leu Pro Leu
    290                   295                   300

Ile Gly Glu Ala Asp Cys Leu His Glu Lys Tyr Gly Gly Leu Asn Lys
305                   310                   315                   320

Ser Lys Pro Tyr Tyr Thr Gly Glu His Ala Lys Ala Ile Gly Asn Cys
                325                   330                   335

Pro Ile Trp Val Lys Thr Pro Leu Lys Leu Ala Asn Gly Thr Lys Tyr
            340                   345                   350

Arg Pro Pro Ala Lys Leu Leu Lys Glu Arg Gly Phe Phe Gly Ala Ile
            355                   360                   365

Ala Gly Phe Leu Glu Gly Gly Trp Glu Gly Met Ile Ala Gly Trp Asn
    370                   375                   380

Gly Tyr Thr Ser His Gly Ala His Gly Val Ala Val Ala Ala Asp Leu
385                   390                   395                   400

Lys Ser Thr Gln Glu Ala Ile Asn Lys Ile Thr Lys Asn Leu Asn Ser
                405                   410                   415

Leu Ser Glu Leu Glu Val Lys Asn Leu Gln Arg Leu Ser Gly Ala Met
            420                   425                   430

Asp Glu Leu His Asn Glu Ile Leu Glu Leu Asp Glu Lys Val Asp Asp
            435                   440                   445

Leu Arg Ala Asp Thr Ile Ser Ser Gln Ile Glu Leu Ala Val Leu Leu
    450                   455                   460
```

-continued

```
Ser Asn Glu Gly Ile Ile Asn Ser Glu Asp Glu Gln Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ser Gly Ser Leu Val Pro Arg Gly
        530                 535                 540

Ser Gly Ser Gly Tyr Ile Pro Glu Ala Pro Arg Asp Gly Gln Ala Tyr
545                 550                 555                 560

Val Arg Lys Asp Gly Glu Trp Val Leu Leu Ser Thr Phe Leu Gly Gly
            565                 570                 575

Ser Leu Pro Glu Thr Gly Gly Gly Ser Asp Tyr Lys Asp Asp Asp Asp
            580                 585                 590

Lys Gly Gly Gly Gly Ser Gly Gly Gly Ser Gly Gly Gly Gly Ser
            595                 600                 605

His His His His His His
    610
```

```
<210> SEQ ID NO 39
<211> LENGTH: 592
<212> TYPE: PRT
<213> ORGANISM: Artificial Sequence
<220> FEATURE:
<223> OTHER INFORMATION: UFV171348

<400> SEQUENCE: 39

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205
```

-continued

```
His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
    530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Gly Ser Gly Gly Gly Gly Ser
                565                 570                 575

Gly Gly Gly Gly Ser Gly Gly Gly Gly Ser His His His His His His
                580                 585                 590
```

<210> SEQ ID NO 40
<211> LENGTH: 592
<212> TYPE: PRT
<213> ORGANISM: Artificial Sequence
<220> FEATURE:

-continued

<223> OTHER INFORMATION: UFV171387

<400> SEQUENCE: 40

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

```
Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
            435             440             445

Leu Arg Ala Asp Thr Ile Ser Ser Gln Ile Glu Leu Ala Val Leu Leu
    450             455             460

Ser Asn Glu Gly Ile Ile Asn Ser Glu Asp Glu Ile Leu Leu Ala Leu
465             470             475             480

Glu Arg Lys Leu Lys Lys Met Leu Gly Pro Ser Ala Val Glu Ile Gly
            485             490             495

Asn Gly Cys Phe Glu Thr Lys His Lys Cys Asn Gln Thr Cys Leu Asp
            500             505             510

Arg Ile Ala Ala Gly Thr Phe Asp Ala Gly Glu Phe Ser Leu Pro Thr
            515             520             525

Phe Asp Ser Leu Asn Ile Thr Ala Ala Ser Leu Asn Asp Asp Gly Leu
    530             535             540

Asp Asn His Thr Ile Ala Ala Ala Asp Tyr Lys Asp Asp Asp Asp Lys
545             550             555             560

Pro Gly Gly Gly Gly Ser Gly Gly Gly Ser Gly Gly Gly Gly Gly Ser
            565             570             575

Gly Gly Gly Gly Ser Gly Gly Gly Ser His His His His His
            580             585             590
```

```
<210> SEQ ID NO 41
<211> LENGTH: 592
<212> TYPE: PRT
<213> ORGANISM: Artificial Sequence
<220> FEATURE:
<223> OTHER INFORMATION: UFV171990

<400> SEQUENCE: 41
```

```
Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
    130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175
```

-continued

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
        450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
        530                 535                 540

Asp Asn His Thr Ile Ala Ala Ala Asp Tyr Lys Asp Asp Asp Lys
545                 550                 555                 560

Pro Gly Gly Gly Gly Ser Gly Gly Gly Ser Gly Gly Gly Gly Ser
                565                 570                 575

Gly Gly Gly Gly Ser Gly Gly Gly Gly Ser His His His His His
            580                 585                 590

```
<210> SEQ ID NO 42
<211> LENGTH: 592
<212> TYPE: PRT
<213> ORGANISM: Artificial Sequence
<220> FEATURE:
<223> OTHER INFORMATION: UFV171993

<400> SEQUENCE: 42

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Asn His Thr Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp Ile
```

-continued

```
              370                  375                  380

Gly Tyr Thr Ser His Gly Ala His Gly Val Ala Val Ala Ala Asp Leu
385                  390                  395                  400

Lys Ser Thr Gln Glu Ala Ile Asn Lys Ile Thr Lys Asn Leu Asn Ser
                  405                  410                  415

Leu Ser Glu Leu Glu Val Lys Asn Leu Gln Arg Leu Ser Gly Ala Met
                  420                  425                  430

Asp Glu Leu His Asn Glu Ile Leu Glu Leu Asp Glu Lys Val Asp Asp
                  435                  440                  445

Leu Arg Ala Asp Thr Ile Ser Ser Gln Ile Glu Leu Arg Val Leu Leu
                  450                  455                  460

Ser Asn Glu Gly Ile Ile Asn Ser Glu Asp Glu Ile Leu Leu Ala Leu
465                  470                  475                  480

Glu Arg Lys Leu Lys Lys Met Leu Gly Pro Ser Ala Val Glu Ile Gly
                  485                  490                  495

Asn Gly Cys Phe Glu Thr Lys His Lys Cys Asn Gln Thr Cys Leu Asp
                  500                  505                  510

Arg Ile Ala Ala Gly Thr Phe Asp Ala Gly Glu Phe Ser Leu Pro Thr
                  515                  520                  525

Phe Asp Ser Leu Asn Ile Thr Ala Ala Ser Leu Asn Asp Asp Gly Leu
                  530                  535                  540

Asp Asn His Thr Ile Ala Ala Ala Asp Tyr Lys Asp Asp Asp Asp Lys
545                  550                  555                  560

Pro Gly Gly Gly Gly Ser Gly Gly Gly Ser Gly Gly Gly Gly Ser
                  565                  570                  575

Gly Gly Gly Gly Ser Gly Gly Gly Gly Ser His His His His His
                  580                  585                  590
```

<210> SEQ ID NO 43
<211> LENGTH: 614
<212> TYPE: PRT
<213> ORGANISM: Artificial Sequence
<220> FEATURE:
<223> OTHER INFORMATION: UFV171472

<400> SEQUENCE: 43

```
Met Lys Ala Ile Ile Val Leu Leu Met Val Val Thr Ser Asn Ala Asp
1                   5                   10                  15

Arg Ile Cys Thr Gly Ile Thr Ser Ser Asn Ser Pro His Val Val Lys
                  20                  25                  30

Thr Ala Thr Gln Gly Glu Val Asn Val Thr Gly Val Ile Pro Leu Thr
                  35                  40                  45

Thr Thr Pro Thr Lys Ser His Phe Ala Asn Leu Lys Gly Thr Glu Thr
                  50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                  85                  90                  95

Ser Ile Leu His Glu Val Arg Pro Val Thr Ser Gly Cys Phe Pro Ile
                  100                 105                 110

Met His Asp Arg Thr Lys Ile Arg Gln Leu Pro Asn Leu Leu Arg Gly
                  115                 120                 125

Tyr Glu His Ile Arg Leu Ser Thr Asn Asn Thr Ile Asn Ala Glu Asn
                  130                 135                 140

Ala Pro Gly Gly Pro Tyr Lys Ile Gly Thr Ser Gly Ser Cys Pro Asn
```

-continued

```
145                  150                  155                  160

Ile Thr Asn Gly Asn Gly Phe Phe Ala Thr Met Ala Trp Ala Val Pro
                165                  170                  175

Lys Asn Asp Lys Asn Lys Thr Ala Thr Asn Pro Leu Thr Ile Glu Val
                180                  185                  190

Pro Tyr Ile Cys Thr Glu Gly Glu Asp Gln Ile Thr Val Trp Gly Phe
                195                  200                  205

His Ser Asp Asn Glu Thr Gln Met Ala Lys Leu Tyr Gly Asp Ser Lys
                210                  215                  220

Pro Gln Lys Phe Thr Ser Ser Ala Asn Gly Val Thr Thr His Tyr Val
225                  230                  235                  240

Ser Gln Ile Gly Gly Phe Pro Asn Gln Thr Glu Asp Gly Gly Leu Pro
                245                  250                  255

Gln Ser Gly Arg Ile Val Val Asp Tyr Met Val Gln Lys Ser Gly Lys
                260                  265                  270

Thr Gly Thr Ile Thr Tyr Gln Arg Gly Ile Leu Leu Pro Gln Lys Val
                275                  280                  285

Trp Cys Ala Ser Gly Arg Ser Lys Val Ile Lys Gly Ser Leu Pro Leu
                290                  295                  300

Ile Gly Glu Ala Asp Cys Leu His Glu Lys Tyr Gly Gly Leu Asn Lys
305                  310                  315                  320

Ser Lys Pro Tyr Tyr Thr Gly Glu His Ala Lys Ala Ile Gly Asn Cys
                325                  330                  335

Pro Ile Trp Val Lys Thr Pro Leu Lys Leu Ala Asn Gly Thr Lys Tyr
                340                  345                  350

Arg Pro Pro Ala Lys Leu Leu Lys Glu Arg Gly Phe Phe Gly Ala Ile
                355                  360                  365

Ala Gly Phe Leu Glu Gly Gly Trp Glu Gly Met Ile Ala Gly Trp His
370                  375                  380

Gly Tyr Thr Ser His Gly Ala His Gly Val Ala Val Ala Ala Asp Leu
385                  390                  395                  400

Lys Ser Thr Gln Glu Ala Ile Asn Lys Ile Thr Lys Asn Leu Asn Ser
                405                  410                  415

Leu Ser Glu Leu Glu Val Lys Asn Leu Gln Arg Leu Ser Gly Ala Met
                420                  425                  430

Asp Glu Leu His Asn Glu Ile Leu Glu Leu Asp Glu Lys Val Asp Asp
                435                  440                  445

Leu Arg Ala Asp Thr Ile Ser Ser Gln Ile Glu Leu Ala Val Leu Leu
                450                  455                  460

Ser Asn Glu Gly Ile Ile Asn Ser Glu Asp Glu His Leu Leu Ala Leu
465                  470                  475                  480

Glu Arg Lys Leu Lys Lys Met Leu Gly Pro Ser Ala Val Glu Ile Gly
                485                  490                  495

Asn Gly Cys Phe Glu Thr Lys His Lys Cys Asn Gln Thr Cys Leu Asp
                500                  505                  510

Arg Ile Ala Ala Gly Thr Phe Asp Ala Gly Glu Phe Ser Leu Pro Thr
                515                  520                  525

Phe Asp Ser Leu Asn Ile Thr Ala Ser Gly Ser Leu Val Pro Arg Gly
                530                  535                  540

Ser Gly Ser Gly Tyr Ile Pro Glu Ala Pro Arg Asp Gly Gln Ala Tyr
545                  550                  555                  560

Val Arg Lys Asp Gly Glu Trp Val Leu Leu Ser Thr Phe Leu Gly Gly
                565                  570                  575
```

-continued

```
Ser Leu Pro Glu Thr Gly Gly Gly Ser Asp Tyr Lys Asp Asp Asp
            580                 585                 590

Lys Gly Gly Gly Ser Gly Gly Gly Gly Ser Gly Gly Gly Gly Ser
        595                 600                 605

His His His His His His
    610

<210> SEQ ID NO 44
<211> LENGTH: 592
<212> TYPE: PRT
<213> ORGANISM: Artificial Sequence
<220> FEATURE:
<223> OTHER INFORMATION: UFV171992

<400> SEQUENCE: 44

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
            85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Thr Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
            245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320
```

```
Ser Lys Pro Tyr Tyr Thr Gly Glu His Ala Lys Ala Ile Gly Asn Cys
            325                 330             335

Pro Ile Trp Val Lys Thr Pro Leu Lys Leu Ala Asn Gly Thr Lys Tyr
            340                 345             350

Arg Pro Pro Ala Lys Leu Leu Lys Glu Arg Gly Phe Phe Gly Ala Ile
        355                 360             365

Ala Gly Phe Leu Glu Gly Gly Trp Glu Gly Met Ile Ala Gly Trp Ile
    370                 375             380

Gly Tyr Thr Ser His Gly Ala His Gly Val Ala Val Ala Ala Asp Leu
385                 390             395             400

Lys Ser Thr Gln Glu Ala Ile Asn Lys Ile Thr Lys Asn Leu Asn Ser
            405                 410             415

Leu Ser Glu Leu Glu Val Lys Asn Leu Gln Arg Leu Ser Gly Ala Met
            420                 425             430

Asp Glu Leu His Asn Glu Ile Leu Glu Leu Asp Glu Lys Val Asp Asp
        435                 440             445

Leu Arg Ala Asp Thr Ile Ser Ser Gln Ile Glu Leu Arg Val Leu Leu
    450                 455             460

Ser Asn Glu Gly Ile Ile Asn Ser Glu Asp Glu Ile Leu Leu Ala Leu
465                 470             475             480

Glu Arg Lys Leu Lys Lys Met Leu Gly Pro Ser Ala Val Glu Ile Gly
            485                 490             495

Asn Gly Cys Phe Glu Thr Lys His Lys Cys Asn Gln Thr Cys Leu Asp
            500                 505             510

Arg Ile Ala Ala Gly Thr Phe Asp Ala Gly Glu Phe Ser Leu Pro Thr
        515                 520             525

Phe Asp Ser Leu Asn Ile Thr Ala Ala Ser Leu Asn Asp Asp Gly Leu
    530                 535             540

Asp Asn His Thr Ile Ala Ala Ala Asp Tyr Lys Asp Asp Asp Asp Lys
545                 550             555             560

Pro Gly Gly Gly Gly Ser Gly Gly Gly Ser Gly Gly Gly Gly Ser
            565                 570             575

Gly Gly Gly Gly Ser Gly Gly Gly Gly Ser His His His His His
            580                 585             590
```

<210> SEQ ID NO 45
<211> LENGTH: 592
<212> TYPE: PRT
<213> ORGANISM: Artificial Sequence
<220> FEATURE:
<223> OTHER INFORMATION: UFV171991

<400> SEQUENCE: 45

```
Met Lys Ala Ile Ile Val Leu Leu Met Val Val Thr Ser Asn Ala Asp
1               5                   10              15

Arg Ile Cys Thr Gly Ile Thr Ser Ser Asn Ser Pro His Val Val Lys
            20                  25              30

Thr Ala Thr Gln Gly Glu Val Asn Val Thr Gly Val Ile Pro Leu Thr
        35                  40              45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75              80

Ala Leu Gly Arg Pro Lys Cys Thr Gly Lys Ile Pro Ser Ala Arg Val
                85                  90              95
```

```
Ser Ile Leu His Glu Val Arg Pro Val Thr Ser Gly Cys Phe Pro Ile
            100                 105             110

Met His Asp Arg Thr Lys Ile Arg Gln Leu Pro Asn Leu Leu Arg Gly
            115                 120             125

Tyr Glu His Ile Arg Leu Ser Thr His Asn Val Ile Asn Ala Glu Asn
            130                 135             140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
            450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510
```

-continued

---

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
        530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Gly Ser Gly Gly Gly Gly Ser
                565                 570                 575

Gly Gly Gly Gly Ser Gly Gly Gly Gly Ser His His His His His His
                580                 585                 590

<210> SEQ ID NO 46
<211> LENGTH: 592
<212> TYPE: PRT
<213> ORGANISM: Artificial Sequence
<220> FEATURE:
<223> OTHER INFORMATION: UFV172064

<400> SEQUENCE: 46

Met Lys Ala Ile Ile Val Leu Leu Met Val Val Thr Ser Asn Ala Asp
1                   5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Phe Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

```
Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
    530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Ser Gly Gly Gly Gly Ser
            565                 570                 575

Gly Gly Gly Gly Ser Gly Gly Gly Ser His His His His His
            580                 585                 590
```

<210> SEQ ID NO 47
<211> LENGTH: 592
<212> TYPE: PRT
<213> ORGANISM: Artificial Sequence
<220> FEATURE:
<223> OTHER INFORMATION: UFV172065

<400> SEQUENCE: 47

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60
```

```
Arg Gly Lys Leu Cys Pro Lys Cys Leu Asn Cys Thr Asp Leu Asp Val
65              70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Trp Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
        420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
```

```
                    485             490             495
Asn Gly Cys Phe Glu Thr Lys His Lys Cys Asn Gln Thr Cys Leu Asp
                500             505             510

Arg Ile Ala Ala Gly Thr Phe Asp Ala Gly Glu Phe Ser Leu Pro Thr
                515             520             525

Phe Asp Ser Leu Asn Ile Thr Ala Ala Ser Leu Asn Asp Asp Gly Leu
                530             535             540

Asp Asn His Thr Ile Ala Ala Ala Asp Tyr Lys Asp Asp Asp Asp Lys
545             550             555             560

Pro Gly Gly Gly Gly Ser Gly Gly Gly Gly Ser Gly Gly Gly Gly Ser
                565             570             575

Gly Gly Gly Gly Ser Gly Gly Gly Gly Ser His His His His His His
                580             585             590

<210> SEQ ID NO 48
<211> LENGTH: 592
<212> TYPE: PRT
<213> ORGANISM: Artificial Sequence
<220> FEATURE:
<223> OTHER INFORMATION: UFV172066

<400> SEQUENCE: 48

Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
                20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
        50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
                85              90              95

Ser Ile Leu His Glu Val Arg Pro Val Thr Ser Gly Cys Phe Pro Ile
                100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
        130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
        195             200             205

His Ser Asp Asn Glu Thr Gln Met Ala Lys Tyr Tyr Gly Asp Ser Lys
    210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
                245             250             255

Gln Ser Gly Arg Ile Val Val Asp Tyr Met Val Gln Lys Ser Gly Lys
```

-continued

```
                260                 265                 270

Thr Gly Thr Ile Thr Tyr Gln Arg Gly Ile Leu Leu Pro Gln Lys Val
                    275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
        305                 310                 315                 320

Ser Lys Pro Tyr Tyr Thr Gly Glu His Ala Lys Ala Ile Gly Asn Cys
                    325                 330                 335

Pro Ile Trp Val Lys Thr Pro Leu Lys Leu Ala Asn Gly Thr Lys Tyr
                    340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp Ile
                370                 375                 380

Gly Tyr Thr Ser His Gly Ala His Gly Val Ala Val Ala Ala Asp Leu
        385                 390                 395                 400

Lys Ser Thr Gln Glu Ala Ile Asn Lys Ile Thr Lys Asn Leu Asn Ser
                    405                 410                 415

Leu Ser Glu Leu Glu Val Lys Asn Leu Gln Arg Leu Ser Gly Ala Met
                    420                 425                 430

Asp Glu Leu His Asn Glu Ile Leu Glu Leu Asp Glu Lys Val Asp Asp
                    435                 440                 445

Leu Arg Ala Asp Thr Ile Ser Ser Gln Ile Glu Leu Arg Val Leu Leu
                450                 455                 460

Ser Asn Glu Gly Ile Ile Asn Ser Glu Asp Glu Ile Leu Leu Ala Leu
        465                 470                 475                 480

Glu Arg Lys Leu Lys Lys Met Leu Gly Pro Ser Ala Val Glu Ile Gly
                    485                 490                 495

Asn Gly Cys Phe Glu Thr Lys His Lys Cys Asn Gln Thr Cys Leu Asp
                    500                 505                 510

Arg Ile Ala Ala Gly Thr Phe Asp Ala Gly Glu Phe Ser Leu Pro Thr
                    515                 520                 525

Phe Asp Ser Leu Asn Ile Thr Ala Ala Ser Leu Asn Asp Asp Gly Leu
                530                 535                 540

Asp Asn His Thr Ile Ala Ala Ala Asp Tyr Lys Asp Asp Asp Lys
        545                 550                 555                 560

Pro Gly Gly Gly Gly Ser Gly Gly Gly Gly Ser Gly Gly Gly Gly Ser
                    565                 570                 575

Gly Gly Gly Gly Ser Gly Gly Gly Gly Ser His His His His His
                    580                 585                 590
```

```
<210> SEQ ID NO 49
<211> LENGTH: 592
<212> TYPE: PRT
<213> ORGANISM: Artificial Sequence
<220> FEATURE:
<223> OTHER INFORMATION: UFV172067

<400> SEQUENCE: 49

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
```

```
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Arg Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
    450                 455                 460
```

```
Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
            530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Ser Gly Gly Gly Gly Ser
                565                 570                 575

Gly Gly Gly Gly Ser Gly Gly Gly Gly Ser His His His His His
            580                 585                 590
```

```
<210> SEQ ID NO 50
<211> LENGTH: 592
<212> TYPE: PRT
<213> ORGANISM: Artificial Sequence
<220> FEATURE:
<223> OTHER INFORMATION: UFV172068

<400> SEQUENCE: 50
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Glu Tyr Gly Asp Ser Lys
        210                 215                 220

Pro Gln Gln Phe Thr Ser Ser Ala Asn Gly Val Thr Thr Ile Tyr Val
225                 230                 235                 240
```

-continued

```
Ser Gln Ile Gly Gly Phe Pro Asn Gln Thr Glu Asp Gly Gly Leu Pro
            245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
            450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
            530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Gly Ser Gly Gly Gly Gly Ser
                565                 570                 575

Gly Gly Gly Gly Ser Gly Gly Gly Gly Ser His His His His His His
            580                 585                 590
```

<210> SEQ ID NO 51
<211> LENGTH: 592
<212> TYPE: PRT
<213> ORGANISM: Artificial Sequence
<220> FEATURE:
<223> OTHER INFORMATION: UFV172069

<400> SEQUENCE: 51

```
Met Lys Ala Ile Ile Val Leu Leu Met Val Val Thr Ser Asn Ala Asp
1               5                   10                  15
```

-continued

```
Arg Ile Cys Thr Gly Ile Thr Ser Ser Asn Ser Pro His Val Val Lys
        20              25              30

Thr Ala Thr Gln Gly Glu Val Asn Val Thr Gly Val Ile Pro Leu Thr
        35              40              45

Thr Thr Pro Thr Lys Ser His Phe Ala Asn Leu Lys Gly Thr Glu Thr
        50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
                85              90              95

Ser Ile Leu His Glu Val Arg Pro Val Thr Ser Gly Cys Phe Pro Ile
                100             105             110

Met His Asp Arg Thr Lys Ile Arg Gln Leu Pro Asn Leu Leu Arg Gly
                115             120             125

Tyr Glu His Ile Arg Leu Ser Thr His Asn Val Ile Asn Ala Glu Asn
        130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
                165             170             175

Lys Asn Asp Lys Asn Lys Thr Ala Thr Asn Pro Leu Thr Ile Glu Val
                180             185             190

Pro Tyr Ile Cys Thr Glu Gly Glu Asp Gln Ile Thr Val Trp Gly Phe
                195             200             205

His Ser Asp Asn Glu Thr Gln Met Ala Lys Leu Tyr Gly Asp Ser Lys
        210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
                245             250             255

Gln Glu Gly Arg Ile Val Val Asp Tyr Met Val Gln Lys Ser Gly Lys
                260             265             270

Thr Gly Thr Ile Thr Tyr Gln Arg Gly Ile Leu Leu Pro Gln Lys Val
                275             280             285

Trp Cys Ala Ser Gly Arg Ser Lys Val Ile Lys Gly Ser Leu Pro Leu
        290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
                325             330             335

Pro Ile Trp Val Lys Thr Pro Leu Lys Leu Ala Asn Gly Thr Lys Tyr
                340             345             350

Arg Pro Pro Ala Lys Leu Leu Lys Glu Arg Gly Phe Phe Gly Ala Ile
                355             360             365

Ala Gly Phe Leu Glu Gly Gly Trp Glu Gly Met Ile Ala Gly Trp Ile
        370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
                405             410             415

Leu Ser Glu Leu Glu Val Lys Asn Leu Gln Arg Leu Ser Gly Ala Met
        420             425             430
```

```
Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
    530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Gly Ser Gly Gly Gly Gly Ser
                565                 570                 575

Gly Gly Gly Gly Ser Gly Gly Gly Gly Ser His His His His His His
                580                 585                 590
```

```
<210> SEQ ID NO 52
<211> LENGTH: 592
<212> TYPE: PRT
<213> ORGANISM: Artificial Sequence
<220> FEATURE:
<223> OTHER INFORMATION: UFV172070

<400> SEQUENCE: 52

Met Lys Ala Ile Ile Val Leu Leu Met Val Val Thr Ser Asn Ala Asp
1                   5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205
```

```
His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Asp Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
    530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Ser Gly Gly Gly Gly Ser
                565                 570                 575

Gly Gly Gly Gly Ser Gly Gly Gly Gly Ser His His His His His
                580                 585                 590
```

<210> SEQ ID NO 53
<211> LENGTH: 592
<212> TYPE: PRT
<213> ORGANISM: Artificial Sequence
<220> FEATURE:
<223> OTHER INFORMATION: UFV172071

```
<400> SEQUENCE: 53

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Val Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
```

-continued

```
                  405               410               415
Leu Ser Glu Leu Glu Val Lys Asn Leu Gln Arg Leu Ser Gly Ala Met
          420               425               430

Asp Glu Leu His Asn Glu Ile Leu Glu Leu Asp Glu Lys Val Asp Asp
          435               440               445

Leu Arg Ala Asp Thr Ile Ser Ser Gln Ile Glu Leu Arg Val Leu Leu
          450               455               460

Ser Asn Glu Gly Ile Ile Asn Ser Glu Asp Glu Ile Leu Leu Ala Leu
465               470               475               480

Glu Arg Lys Leu Lys Lys Met Leu Gly Pro Ser Ala Val Glu Ile Gly
              485               490               495

Asn Gly Cys Phe Glu Thr Lys His Lys Cys Asn Gln Thr Cys Leu Asp
              500               505               510

Arg Ile Ala Ala Gly Thr Phe Asp Ala Gly Glu Phe Ser Leu Pro Thr
          515               520               525

Phe Asp Ser Leu Asn Ile Thr Ala Ala Ser Leu Asn Asp Asp Gly Leu
          530               535               540

Asp Asn His Thr Ile Ala Ala Ala Asp Tyr Lys Asp Asp Asp Lys
545               550               555               560

Pro Gly Gly Gly Gly Ser Gly Gly Gly Ser Gly Gly Gly Gly Ser
              565               570               575

Gly Gly Gly Gly Ser Gly Gly Gly Gly Ser His His His His His
              580               585               590
```

<210> SEQ ID NO 54
<211> LENGTH: 592
<212> TYPE: PRT
<213> ORGANISM: Artificial Sequence
<220> FEATURE:
<223> OTHER INFORMATION: UFV172072

<400> SEQUENCE: 54

```
Met Lys Ala Ile Ile Val Leu Leu Met Val Val Thr Ser Asn Ala Asp
1               5               10                15

Arg Ile Cys Thr Gly Ile Thr Ser Ser Asn Ser Pro His Val Val Lys
              20               25               30

Thr Ala Thr Gln Gly Glu Val Asn Val Thr Gly Val Ile Pro Leu Thr
          35               40               45

Thr Thr Pro Thr Lys Ser His Phe Ala Asn Leu Lys Gly Thr Glu Thr
      50               55               60

Arg Gly Lys Leu Cys Pro Lys Cys Leu Asn Cys Thr Asp Leu Asp Val
65               70               75               80

Ala Leu Gly Arg Pro Lys Cys Thr Gly Lys Ile Pro Ser Ala Arg Val
              85               90               95

Ser Ile Leu His Glu Val Arg Pro Val Thr Ser Gly Cys Phe Pro Ile
              100               105               110

Met His Asp Arg Thr Lys Ile Arg Gln Leu Pro Asn Leu Leu Arg Gly
          115               120               125

Tyr Glu His Ile Arg Leu Ser Thr His Asn Val Ile Asn Ala Glu Asn
          130               135               140

Ala Pro Gly Gly Pro Tyr Lys Ile Gly Thr Ser Gly Ser Cys Pro Asn
145               150               155               160

Ile Thr Asn Gly Asn Gly Phe Phe Ala Thr Met Ala Trp Ala Val Pro
              165               170               175

Lys Asn Asp Lys Asn Lys Thr Ala Thr Asn Pro Leu Thr Ile Glu Val
```

-continued

```
                 180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
        210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
            245             250             255

Gln Phe Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
            275             280             285

Trp Cys Ala Ser Gly Arg Ser Lys Val Ile Lys Gly Ser Leu Pro Leu
        290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
            325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
            355             360             365

Ala Gly Phe Leu Glu Gly Gly Trp Glu Gly Met Ile Ala Gly Trp Ile
        370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
            435             440             445

Leu Arg Ala Asp Thr Ile Ser Ser Gln Ile Glu Leu Arg Val Leu Leu
        450             455             460

Ser Asn Glu Gly Ile Ile Asn Ser Glu Asp Glu Ile Leu Leu Ala Leu
465             470             475             480

Glu Arg Lys Leu Lys Lys Met Leu Gly Pro Ser Ala Val Glu Ile Gly
            485             490             495

Asn Gly Cys Phe Glu Thr Lys His Lys Cys Asn Gln Thr Cys Leu Asp
            500             505             510

Arg Ile Ala Ala Gly Thr Phe Asp Ala Gly Glu Phe Ser Leu Pro Thr
            515             520             525

Phe Asp Ser Leu Asn Ile Thr Ala Ala Ser Leu Asn Asp Asp Gly Leu
        530             535             540

Asp Asn His Thr Ile Ala Ala Ala Asp Tyr Lys Asp Asp Asp Asp Lys
545             550             555             560

Pro Gly Gly Gly Gly Ser Gly Gly Gly Ser Gly Gly Gly Gly Ser
            565             570             575

Gly Gly Gly Gly Ser Gly Gly Gly Gly Ser His His His His His
            580             585             590
```

<210> SEQ ID NO 55

<211> LENGTH: 592
<212> TYPE: PRT
<213> ORGANISM: Artificial Sequence
<220> FEATURE:
<223> OTHER INFORMATION: UFV172073

<400> SEQUENCE: 55

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp Ile
    370                 375                 380
```

```
Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
            435             440             445

Leu Arg Ala Asp Thr Ile Ser Ser Gln Ile Glu Leu Arg Val Leu Leu
            450             455             460

Ser Asn Glu Gly Ile Ile Asn Ser Glu Asp Glu Ile Leu Leu Ala Leu
465             470             475             480

Glu Arg Lys Leu Lys Lys Met Leu Gly Pro Ser Ala Val Glu Ile Gly
            485             490             495

Asn Gly Cys Phe Glu Thr Lys His Lys Cys Asn Gln Thr Cys Leu Asp
            500             505             510

Arg Ile Ala Ala Gly Thr Phe Asp Ala Gly Glu Phe Ser Leu Pro Thr
            515             520             525

Phe Asp Ser Leu Asn Ile Thr Ala Ala Ser Leu Asn Asp Asp Gly Leu
            530             535             540

Asp Asn His Thr Ile Ala Ala Ala Asp Tyr Lys Asp Asp Asp Asp Lys
545             550             555             560

Pro Gly Gly Gly Gly Ser Gly Gly Gly Ser Gly Gly Gly Gly Ser
            565             570             575

Gly Gly Gly Gly Ser Gly Gly Gly Gly Ser His His His His His
            580             585             590
```

<210> SEQ ID NO 56
<211> LENGTH: 592
<212> TYPE: PRT
<213> ORGANISM: Artificial Sequence
<220> FEATURE:
<223> OTHER INFORMATION: UFV172074

<400> SEQUENCE: 56

```
Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
            50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
            130             135             140

Ala Pro Gly Gly Pro Tyr Lys Ile Gly Thr Ser Gly Ser Cys Pro Asn
145             150             155             160
```

-continued

```
Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
            245                 250                 255

Asp Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
            450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
            530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Gly Ser Gly Gly Gly Gly Ser
            565                 570                 575
```

```
Gly Gly Gly Gly Ser Gly Gly Gly Ser His His His His His
        580                 585                 590
```

<210> SEQ ID NO 57
<211> LENGTH: 592
<212> TYPE: PRT
<213> ORGANISM: Artificial Sequence
<220> FEATURE:
<223> OTHER INFORMATION: UFV172075

<400> SEQUENCE: 57

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
        180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Val Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350
```

```
Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp Ile
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
        420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
        450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
        530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Ser Gly Gly Gly Gly Ser
                565                 570                 575

Gly Gly Gly Gly Ser Gly Gly Gly Ser His His His His His
            580                 585                 590
```

<210> SEQ ID NO 58
<211> LENGTH: 592
<212> TYPE: PRT
<213> ORGANISM: Artificial Sequence
<220> FEATURE:
<223> OTHER INFORMATION: UFV172076

<400> SEQUENCE: 58

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125
```

```
Tyr Glu His Ile Arg Leu Ser Thr His Asn Val Ile Asn Ala Glu Asn
    130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
                165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
    210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
                245             250             255

Phe Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
            275             280             285

Trp Cys Ala Ser Gly Arg Ser Lys Val Ile Lys Gly Ser Leu Pro Leu
    290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
            325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
    355             360             365

Ala Gly Phe Leu Glu Gly Gly Trp Glu Gly Met Ile Ala Gly Trp Ile
    370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
    435             440             445

Leu Arg Ala Asp Thr Ile Ser Ser Gln Ile Glu Leu Arg Val Leu Leu
    450             455             460

Ser Asn Glu Gly Ile Ile Asn Ser Glu Asp Glu Ile Leu Leu Ala Leu
465             470             475             480

Glu Arg Lys Leu Lys Lys Met Leu Gly Pro Ser Ala Val Glu Ile Gly
            485             490             495

Asn Gly Cys Phe Glu Thr Lys His Lys Cys Asn Gln Thr Cys Leu Asp
            500             505             510

Arg Ile Ala Ala Gly Thr Phe Asp Ala Gly Glu Phe Ser Leu Pro Thr
            515             520             525

Phe Asp Ser Leu Asn Ile Thr Ala Ala Ser Leu Asn Asp Asp Gly Leu
    530             535             540

Asp Asn His Thr Ile Ala Ala Ala Asp Tyr Lys Asp Asp Asp Asp Lys
```

```
545                 550                 555                 560

Pro Gly Gly Gly Gly Ser Gly Gly Gly Gly Ser Gly Gly Gly Gly Ser
                565                 570                 575

Gly Gly Gly Gly Ser Gly Gly Gly Gly Ser His His His His His His
                580                 585                 590

<210> SEQ ID NO 59
<211> LENGTH: 592
<212> TYPE: PRT
<213> ORGANISM: Artificial Sequence
<220> FEATURE:
<223> OTHER INFORMATION: UFV172077

<400> SEQUENCE: 59

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Phe Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
```

```
                325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
            355             360             365

Ala Gly Phe Leu Glu Gly Gly Trp Glu Gly Met Ile Ala Gly Trp Ile
            370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
            435             440             445

Leu Arg Ala Asp Thr Ile Ser Ser Gln Ile Glu Leu Arg Val Leu Leu
            450             455             460

Ser Asn Glu Gly Ile Ile Asn Ser Glu Asp Glu Ile Leu Leu Ala Leu
465             470             475             480

Glu Arg Lys Leu Lys Lys Met Leu Gly Pro Ser Ala Val Glu Ile Gly
            485             490             495

Asn Gly Cys Phe Glu Thr Lys His Lys Cys Asn Gln Thr Cys Leu Asp
            500             505             510

Arg Ile Ala Ala Gly Thr Phe Asp Ala Gly Glu Phe Ser Leu Pro Thr
            515             520             525

Phe Asp Ser Leu Asn Ile Thr Ala Ala Ser Leu Asn Asp Asp Gly Leu
            530             535             540

Asp Asn His Thr Ile Ala Ala Ala Asp Tyr Lys Asp Asp Asp Asp Lys
545             550             555             560

Pro Gly Gly Gly Gly Ser Gly Gly Gly Gly Ser Gly Gly Gly Gly Ser
            565             570             575

Gly Gly Gly Gly Ser Gly Gly Gly Gly Ser His His His His His His
            580             585             590
```

<210> SEQ ID NO 60
<211> LENGTH: 592
<212> TYPE: PRT
<213> ORGANISM: Artificial Sequence
<220> FEATURE:
<223> OTHER INFORMATION: UFV172078

<400> SEQUENCE: 60

```
Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
            50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
```

```
                100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Trp Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525
```

256

-continued

```
Phe Asp Ser Leu Asn Ile Thr Ala Ala Ser Leu Asn Asp Asp Gly Leu
    530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Gly Ser Gly Gly Gly Gly Ser
                565                 570                 575

Gly Gly Gly Gly Ser Gly Gly Gly Gly Ser His His His His His
                580                 585                 590

<210> SEQ ID NO 61
<211> LENGTH: 592
<212> TYPE: PRT
<213> ORGANISM: Artificial Sequence
<220> FEATURE:
<223> OTHER INFORMATION: UFV172079

<400> SEQUENCE: 61

Met Lys Ala Ile Ile Val Leu Leu Met Val Val Thr Ser Asn Ala Asp
1               5                  10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Tyr Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300
```

```
Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Ala Ala Ala Asp Tyr Lys Asp Asp Asp Asp Lys
545                 550                 555                 560

Pro Gly Gly Gly Gly Ser Gly Gly Gly Gly Ser Gly Gly Gly Gly Ser
                565                 570                 575

Gly Gly Gly Gly Ser Gly Gly Gly Gly Ser His His His His His
            580                 585                 590
```

```
<210> SEQ ID NO 62
<211> LENGTH: 587
<212> TYPE: PRT
<213> ORGANISM: Artificial Sequence
<220> FEATURE:
<223> OTHER INFORMATION: UFV172678

<400> SEQUENCE: 62

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80
```

```
Ala Leu Gly Arg Pro Lys Cys Thr Gly Lys Ile Pro Ser Ala Arg Val
             85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Glu Gly Met Ile Ala Gly Trp Ile Gly Tyr Thr Ser His
        370                 375                 380

Gly Ala His Gly Val Ala Val Ala Ala Asp Leu Lys Ser Thr Gln Glu
385                 390                 395                 400

Ala Ile Asn Lys Ile Thr Lys Asn Leu Asn Ser Leu Ser Glu Leu Glu
                405                 410                 415

Val Lys Asn Leu Gln Arg Leu Ser Gly Ala Met Asp Glu Leu His Asn
            420                 425                 430

Glu Ile Leu Glu Leu Asp Glu Lys Val Asp Asp Leu Arg Ala Asp Thr
            435                 440                 445

Ile Ser Ser Gln Ile Glu Leu Arg Val Leu Leu Ser Asn Glu Gly Ile
        450                 455                 460

Ile Asn Ser Glu Asp Glu Ile Leu Leu Ala Leu Glu Arg Lys Leu Lys
465                 470                 475                 480

Lys Met Leu Gly Pro Ser Ala Val Glu Ile Gly Asn Gly Cys Phe Glu
                485                 490                 495
```

-continued

```
Thr Lys His Lys Cys Asn Gln Thr Cys Leu Asp Arg Ile Ala Ala Gly
            500             505             510

Thr Phe Asp Ala Gly Glu Phe Ser Leu Pro Thr Phe Asp Ser Leu Asn
            515             520             525

Ile Thr Ala Ala Ser Leu Asn Asp Asp Gly Leu Asp Asn His Thr Ile
            530             535             540

Ala Ala Ala Asp Tyr Lys Asp Asp Asp Lys Pro Gly Gly Gly Gly
545             550             555             560

Ser Gly Gly Gly Gly Ser Gly Gly Gly Gly Ser Gly Gly Gly Gly Ser
            565             570             575

Gly Gly Gly Gly Ser His His His His His His
            580             585

<210> SEQ ID NO 63
<211> LENGTH: 587
<212> TYPE: PRT
<213> ORGANISM: Artificial Sequence
<220> FEATURE:
<223> OTHER INFORMATION: UFV172680

<400> SEQUENCE: 63

Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
            50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
            130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
            210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
            245             250             255

Gln Ser Gly Arg Ile Val Val Asp Tyr Met Val Gln Lys Ser Gly Lys
            260             265             270
```

```
Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
        355                 360                 365

Ala Gly Phe Leu Gly Met Ile Ala Gly Trp Ile Gly Tyr Thr Ser His
        370                 375                 380

Gly Ala His Gly Val Ala Val Ala Ala Asp Leu Lys Ser Thr Gln Glu
385                 390                 395                 400

Ala Ile Asn Lys Ile Thr Lys Asn Leu Asn Ser Leu Ser Glu Leu Glu
                405                 410                 415

Val Lys Asn Leu Gln Arg Leu Ser Gly Ala Met Asp Glu Leu His Asn
                420                 425                 430

Glu Ile Leu Glu Leu Asp Glu Lys Val Asp Asp Leu Arg Ala Asp Thr
        435                 440                 445

Ile Ser Ser Gln Ile Glu Leu Arg Val Leu Leu Ser Asn Glu Gly Ile
        450                 455                 460

Ile Asn Ser Glu Asp Glu Ile Leu Leu Ala Leu Glu Arg Lys Leu Lys
465                 470                 475                 480

Lys Met Leu Gly Pro Ser Ala Val Glu Ile Gly Asn Gly Cys Phe Glu
                485                 490                 495

Thr Lys His Lys Cys Asn Gln Thr Cys Leu Asp Arg Ile Ala Ala Gly
                500                 505                 510

Thr Phe Asp Ala Gly Glu Phe Ser Leu Pro Thr Phe Asp Ser Leu Asn
        515                 520                 525

Ile Thr Ala Ala Ser Leu Asn Asp Asp Gly Leu Asp Asn His Thr Ile
        530                 535                 540

Ala Ala Ala Asp Tyr Lys Asp Asp Asp Lys Pro Gly Gly Gly Gly
545                 550                 555                 560

Ser Gly Gly Gly Gly Ser Gly Gly Gly Ser Gly Gly Gly Gly Ser
                565                 570                 575

Gly Gly Gly Gly Ser His His His His His His
                580                 585
```

```
<210> SEQ ID NO 64
<211> LENGTH: 586
<212> TYPE: PRT
<213> ORGANISM: Artificial Sequence
<220> FEATURE:
<223> OTHER INFORMATION: UFV172681

<400> SEQUENCE: 64

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
        35                  40                  45
```

-continued

```
Thr Thr Pro Thr Lys Ser His Phe Ala Asn Leu Lys Gly Thr Glu Thr
    50              55                  60

Arg Gly Lys Leu Cys Pro Lys Cys Leu Asn Cys Thr Asp Leu Asp Val
65              70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Ile Ala Gly Trp Ile Gly Tyr Thr Ser His Gly
    370                 375                 380

Ala His Gly Val Ala Val Ala Ala Asp Leu Lys Ser Thr Gln Glu Ala
385                 390                 395                 400

Ile Asn Lys Ile Thr Lys Asn Leu Asn Ser Leu Ser Glu Leu Glu Val
                405                 410                 415

Lys Asn Leu Gln Arg Leu Ser Gly Ala Met Asp Glu Leu His Asn Glu
            420                 425                 430

Ile Leu Glu Leu Asp Glu Lys Val Asp Asp Leu Arg Ala Asp Thr Ile
            435                 440                 445

Ser Ser Gln Ile Glu Leu Arg Val Leu Leu Ser Asn Glu Gly Ile Ile
    450                 455                 460

Asn Ser Glu Asp Glu Ile Leu Leu Ala Leu Glu Arg Lys Leu Lys Lys
```

```
465                    470                    475                    480

Met Leu Gly Pro Ser Ala Val Glu Ile Gly Asn Gly Cys Phe Glu Thr
             485                    490                    495

Lys His Lys Cys Asn Gln Thr Cys Leu Asp Arg Ile Ala Ala Gly Thr
             500                    505                    510

Phe Asp Ala Gly Glu Phe Ser Leu Pro Thr Phe Asp Ser Leu Asn Ile
             515                    520                    525

Thr Ala Ala Ser Leu Asn Asp Asp Gly Leu Asp Asn His Thr Ile Ala
             530                    535                    540

Ala Ala Asp Tyr Lys Asp Asp Asp Lys Pro Gly Gly Gly Gly Ser
545                    550                    555                    560

Gly Gly Gly Gly Ser Gly Gly Gly Ser Gly Gly Gly Gly Ser Gly
             565                    570                    575

Gly Gly Gly Ser His His His His His His
             580                    585
```

```
<210> SEQ ID NO 65
<211> LENGTH: 585
<212> TYPE: PRT
<213> ORGANISM: Artificial Sequence
<220> FEATURE:
<223> OTHER INFORMATION: UFV172683

<400> SEQUENCE: 65

Met Lys Ala Ile Ile Val Leu Leu Met Val Val Thr Ser Asn Ala Asp
1               5                    10                    15

Arg Ile Cys Thr Gly Ile Thr Ser Ser Asn Ser Pro His Val Val Lys
             20                    25                    30

Thr Ala Thr Gln Gly Glu Val Asn Val Thr Gly Val Ile Pro Leu Thr
             35                    40                    45

Thr Thr Pro Thr Lys Ser His Phe Ala Asn Leu Lys Gly Thr Glu Thr
             50                    55                    60

Arg Gly Lys Leu Cys Pro Lys Cys Leu Asn Cys Thr Asp Leu Asp Val
65                    70                    75                    80

Ala Leu Gly Arg Pro Lys Cys Thr Gly Lys Ile Pro Ser Ala Arg Val
             85                    90                    95

Ser Ile Leu His Glu Val Arg Pro Val Thr Ser Gly Cys Phe Pro Ile
             100                   105                   110

Met His Asp Arg Thr Lys Ile Arg Gln Leu Pro Asn Leu Leu Arg Gly
             115                   120                   125

Tyr Glu His Ile Arg Leu Ser Thr His Asn Val Ile Asn Ala Glu Asn
             130                   135                   140

Ala Pro Gly Gly Pro Tyr Lys Ile Gly Thr Ser Gly Ser Cys Pro Asn
145                   150                   155                   160

Ile Thr Asn Gly Asn Gly Phe Phe Ala Thr Met Ala Trp Ala Val Pro
             165                   170                   175

Lys Asn Asp Lys Asn Lys Thr Ala Thr Asn Pro Leu Thr Ile Glu Val
             180                   185                   190

Pro Tyr Ile Cys Thr Glu Gly Glu Asp Gln Ile Thr Val Trp Gly Phe
             195                   200                   205

His Ser Asp Asn Glu Thr Gln Met Ala Lys Leu Tyr Gly Asp Ser Lys
             210                   215                   220

Pro Gln Gln Phe Thr Ser Ser Ala Asn Gly Val Thr Thr Ile Tyr Val
225                   230                   235                   240

Ser Gln Ile Gly Gly Phe Pro Asn Gln Thr Glu Asp Gly Gly Leu Pro
```

-continued

```
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Met Ile Ala Gly Trp Ile Gly Tyr Thr Ser His Gly Ala
    370                 375                 380

His Gly Val Ala Val Ala Ala Asp Leu Lys Ser Thr Gln Glu Ala Ile
385                 390                 395                 400

Asn Lys Ile Thr Lys Asn Leu Asn Ser Leu Ser Glu Leu Glu Val Lys
                405                 410                 415

Asn Leu Gln Arg Leu Ser Gly Ala Met Asp Glu Leu His Asn Glu Ile
            420                 425                 430

Leu Glu Leu Asp Glu Lys Val Asp Asp Leu Arg Ala Asp Thr Ile Ser
            435                 440                 445

Ser Gln Ile Glu Leu Arg Val Leu Leu Ser Asn Glu Gly Ile Ile Asn
    450                 455                 460

Ser Glu Asp Glu Ile Leu Leu Ala Leu Glu Arg Lys Leu Lys Lys Met
465                 470                 475                 480

Leu Gly Pro Ser Ala Val Glu Ile Gly Asn Gly Cys Phe Glu Thr Lys
            485                 490                 495

His Lys Cys Asn Gln Thr Cys Leu Asp Arg Ile Ala Ala Gly Thr Phe
            500                 505                 510

Asp Ala Gly Glu Phe Ser Leu Pro Thr Phe Asp Ser Leu Asn Ile Thr
        515                 520                 525

Ala Ala Ser Leu Asn Asp Asp Gly Leu Asp Asn His Thr Ile Ala Ala
    530                 535                 540

Ala Asp Tyr Lys Asp Asp Asp Lys Pro Gly Gly Gly Gly Ser Gly
545                 550                 555                 560

Gly Gly Gly Ser Gly Gly Gly Ser Gly Gly Gly Gly Ser Gly Gly
            565                 570                 575

Gly Gly Ser His His His His His
            580                 585
```

```
<210> SEQ ID NO 66
<211> LENGTH: 588
<212> TYPE: PRT
<213> ORGANISM: Artificial Sequence
<220> FEATURE:
<223> OTHER INFORMATION: UFV172686

<400> SEQUENCE: 66

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
```

-continued

```
              20              25              30

Thr Ala Thr Gln Gly Glu Val Asn Val Thr Gly Val Ile Pro Leu Thr
        35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
    130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
    210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
            245             250             255

Gln Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
            275             280             285

Trp Cys Ala Ser Gly Arg Ser Lys Val Ile Lys Gly Ser Leu Pro Leu
    290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
            325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
            355             360             365

Ala Gly Phe Leu Glu Gly Met Ile Ala Gly Trp Ile Gly Tyr Thr Ser
    370             375             380

His Gly Ala His Gly Val Ala Val Ala Ala Asp Leu Lys Ser Thr Gln
385             390             395             400

Glu Ala Ile Asn Lys Ile Thr Lys Asn Leu Asn Ser Leu Ser Glu Leu
            405             410             415

Glu Val Lys Asn Leu Gln Arg Leu Ser Gly Ala Met Asp Glu Leu His
            420             425             430

Asn Glu Ile Leu Glu Leu Asp Glu Lys Val Asp Asp Leu Arg Ala Asp
            435             440             445
```

```
Thr Ile Ser Ser Gln Ile Glu Leu Arg Val Leu Leu Ser Asn Glu Gly
    450             455             460

Ile Ile Asn Ser Glu Asp Glu Ile Leu Leu Ala Leu Glu Arg Lys Leu
465             470             475             480

Lys Lys Met Leu Gly Pro Ser Ala Val Glu Ile Gly Asn Gly Cys Phe
            485             490             495

Glu Thr Lys His Lys Cys Asn Gln Thr Cys Leu Asp Arg Ile Ala Ala
            500             505             510

Gly Thr Phe Asp Ala Gly Glu Phe Ser Leu Pro Thr Phe Asp Ser Leu
            515             520             525

Asn Ile Thr Ala Ala Ser Leu Asn Asp Asp Gly Leu Asp Asn His Thr
    530             535             540

Ile Ala Ala Ala Asp Tyr Lys Asp Asp Asp Lys Pro Gly Gly Gly
545             550             555             560

Gly Ser Gly Gly Gly Gly Ser Gly Gly Gly Ser Gly Gly Gly Gly
            565             570             575

Ser Gly Gly Gly Gly Ser His His His His His His
            580             585
```

```
<210> SEQ ID NO 67
<211> LENGTH: 589
<212> TYPE: PRT
<213> ORGANISM: Artificial Sequence
<220> FEATURE:
<223> OTHER INFORMATION: UFV172687

<400> SEQUENCE: 67
```

```
Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Thr His Asn Val Ile Asn Ala Glu Asn
    130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
    210             215             220
```

-continued

```
Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Glu Gly Met Ile Ala Gly Trp Ile Gly Tyr Thr
            370                 375                 380

Ser His Gly Ala His Gly Val Ala Val Ala Ala Asp Leu Lys Ser Thr
385                 390                 395                 400

Gln Glu Ala Ile Asn Lys Ile Thr Lys Asn Leu Asn Ser Leu Ser Glu
                405                 410                 415

Leu Glu Val Lys Asn Leu Gln Arg Leu Ser Gly Ala Met Asp Glu Leu
            420                 425                 430

His Asn Glu Ile Leu Glu Leu Asp Glu Lys Val Asp Asp Leu Arg Ala
            435                 440                 445

Asp Thr Ile Ser Ser Gln Ile Glu Leu Arg Val Leu Leu Ser Asn Glu
        450                 455                 460

Gly Ile Ile Asn Ser Glu Asp Glu Ile Leu Leu Ala Leu Glu Arg Lys
465                 470                 475                 480

Leu Lys Lys Met Leu Gly Pro Ser Ala Val Glu Ile Gly Asn Gly Cys
                485                 490                 495

Phe Glu Thr Lys His Lys Cys Asn Gln Thr Cys Leu Asp Arg Ile Ala
                500                 505                 510

Ala Gly Thr Phe Asp Ala Gly Glu Phe Ser Leu Pro Thr Phe Asp Ser
            515                 520                 525

Leu Asn Ile Thr Ala Ala Ser Leu Asn Asp Asp Gly Leu Asp Asn His
        530                 535                 540

Thr Ile Ala Ala Ala Asp Tyr Lys Asp Asp Asp Lys Pro Gly Gly
545                 550                 555                 560

Gly Gly Ser Gly Gly Gly Gly Ser Gly Gly Gly Gly Ser Gly Gly Gly
            565                 570                 575

Gly Ser Gly Gly Gly Gly Ser His His His His His
            580                 585
```

<210> SEQ ID NO 68
<211> LENGTH: 587
<212> TYPE: PRT
<213> ORGANISM: Artificial Sequence
<220> FEATURE:
<223> OTHER INFORMATION: UFV172691

<400> SEQUENCE: 68

-continued

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Ala Gly Trp Ile Gly Tyr Thr Ser His
    370                 375                 380

Gly Ala His Gly Val Ala Val Ala Ala Asp Leu Lys Ser Thr Gln Glu
385                 390                 395                 400

Ala Ile Asn Lys Ile Thr Lys Asn Leu Asn Ser Leu Ser Glu Leu Glu
                405                 410                 415
```

```
Val Lys Asn Leu Gln Arg Leu Ser Gly Ala Met Asp Glu Leu His Asn
        420                 425                 430

Glu Ile Leu Glu Leu Asp Glu Lys Val Asp Asp Leu Arg Ala Asp Thr
        435                 440                 445

Ile Ser Ser Gln Ile Glu Leu Arg Val Leu Leu Ser Asn Glu Gly Ile
        450                 455                 460

Ile Asn Ser Glu Asp Glu Ile Leu Leu Ala Leu Glu Arg Lys Leu Lys
465                 470                 475                 480

Lys Met Leu Gly Pro Ser Ala Val Glu Ile Gly Asn Gly Cys Phe Glu
                485                 490                 495

Thr Lys His Lys Cys Asn Gln Thr Cys Leu Asp Arg Ile Ala Ala Gly
        500                 505                 510

Thr Phe Asp Ala Gly Glu Phe Ser Leu Pro Thr Phe Asp Ser Leu Asn
        515                 520                 525

Ile Thr Ala Ala Ser Leu Asn Asp Asp Gly Leu Asp Asn His Thr Ile
        530                 535                 540

Ala Ala Ala Asp Tyr Lys Asp Asp Asp Lys Pro Gly Gly Gly Gly
545                 550                 555                 560

Ser Gly Gly Gly Gly Ser Gly Gly Gly Ser Gly Gly Gly Gly Ser
                565                 570                 575

Gly Gly Gly Gly Ser His His His His His His
                580                 585
```

```
<210> SEQ ID NO 69
<211> LENGTH: 587
<212> TYPE: PRT
<213> ORGANISM: Artificial Sequence
<220> FEATURE:
<223> OTHER INFORMATION: UFV172690

<400> SEQUENCE: 69
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65              70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190
```

```
Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Gly Trp Ile Gly Tyr Thr Ser His
        370                 375                 380

Gly Ala His Gly Val Ala Val Ala Ala Asp Leu Lys Ser Thr Gln Glu
385                 390                 395                 400

Ala Ile Asn Lys Ile Thr Lys Asn Leu Asn Ser Leu Ser Glu Leu Glu
                405                 410                 415

Val Lys Asn Leu Gln Arg Leu Ser Gly Ala Met Asp Glu Leu His Asn
                420                 425                 430

Glu Ile Leu Glu Leu Asp Glu Lys Val Asp Asp Leu Arg Ala Asp Thr
        435                 440                 445

Ile Ser Ser Gln Ile Glu Leu Arg Val Leu Leu Ser Asn Glu Gly Ile
        450                 455                 460

Ile Asn Ser Glu Asp Glu Ile Leu Leu Ala Leu Glu Arg Lys Leu Lys
465                 470                 475                 480

Lys Met Leu Gly Pro Ser Ala Val Glu Ile Gly Asn Gly Cys Phe Glu
                485                 490                 495

Thr Lys His Lys Cys Asn Gln Thr Cys Leu Asp Arg Ile Ala Ala Gly
                500                 505                 510

Thr Phe Asp Ala Gly Glu Phe Ser Leu Pro Thr Phe Asp Ser Leu Asn
        515                 520                 525

Ile Thr Ala Ala Ser Leu Asn Asp Asp Gly Leu Asp Asn His Thr Ile
        530                 535                 540

Ala Ala Ala Asp Tyr Lys Asp Asp Asp Lys Pro Gly Gly Gly Gly
545                 550                 555                 560

Ser Gly Gly Gly Gly Ser Gly Gly Gly Gly Ser Gly Gly Gly Gly Ser
                565                 570                 575

Gly Gly Gly Gly Ser His His His His His
                580                 585
```

<210> SEQ ID NO 70
<211> LENGTH: 553
<212> TYPE: PRT

```
<213> ORGANISM: Artificial Sequence
<220> FEATURE:
<223> OTHER INFORMATION: UFV180284

<400> SEQUENCE: 70

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Glu His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
```

-continued

```
385              390              395              400

Lys Ser Thr Gln Glu Ala Ile Asn Lys Ile Thr Lys Asn Leu Asn Ser
             405              410              415

Leu Ser Glu Leu Glu Val Lys Asn Leu Gln Arg Leu Ser Gly Ala Met
             420              425              430

Asp Glu Leu His Asn Glu Ile Leu Glu Leu Asp Glu Lys Val Asp Asp
             435              440              445

Leu Arg Ala Asp Thr Ile Ser Ser Gln Ile Glu Leu Arg Val Leu Leu
    450              455              460

Ser Asn Glu Gly Ile Ile Asn Ser Glu Asp Glu Ile Leu Leu Ala Leu
465              470              475              480

Glu Arg Lys Leu Lys Lys Met Leu Gly Pro Ser Ala Val Glu Ile Gly
             485              490              495

Asn Gly Cys Phe Glu Thr Lys His Lys Cys Asn Gln Thr Cys Leu Asp
             500              505              510

Arg Ile Ala Ala Gly Thr Phe Asp Ala Gly Glu Phe Ser Leu Pro Thr
             515              520              525

Phe Asp Ser Leu Asn Ile Thr Ala Ala Ser Leu Asn Asp Asp Gly Leu
    530              535              540

Asp Asn His Thr Ile Glu Pro Glu Ala
545              550
```

<210> SEQ ID NO 71
<211> LENGTH: 549
<212> TYPE: PRT
<213> ORGANISM: Artificial Sequence
<220> FEATURE:
<223> OTHER INFORMATION: UFV180454

<400> SEQUENCE: 71

```
Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
             20              25              30

Thr Ala Thr Gln Gly Glu Val Asn Val Thr Gly Val Ile Pro Leu Thr
             35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
             85              90              95

Ser Ile Leu His Glu Val Arg Pro Val Thr Ser Gly Cys Phe Pro Ile
             100             105             110

Met His Asp Arg Thr Lys Ile Arg Gln Leu Pro Asn Leu Leu Arg Gly
             115             120             125

Tyr Glu His Ile Arg Leu Ser Glu His Asn Val Ile Asn Ala Thr Asn
    130             135             140

Ala Pro Gly Gly Pro Tyr Asn Ile Thr Thr Ser Gly Ser Cys Pro Asn
145             150             155             160

Ile Thr Asn Gly Asn Gly Phe Phe Ala Thr Met Ala Trp Ala Val Pro
             165             170             175

Lys Asn Asp Lys Asn Lys Thr Ala Thr Asn Pro Leu Thr Ile Glu Val
             180             185             190

Pro Tyr Ile Cys Thr Glu Gly Glu Asp Gln Ile Thr Val Trp Gly Phe
```

```
                195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
                290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Gln Gly Phe Phe Gly Ala Ile
                355                 360                 365

Ala Gly Phe Leu Glu Gly Gly Trp Glu Gly Met Ile Ala Gly Trp Ile
                370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
    530                 535                 540

Asp Asn His Thr Ile
545

<210> SEQ ID NO 72
<211> LENGTH: 547
<212> TYPE: PRT
<213> ORGANISM: Artificial Sequence
<220> FEATURE:
<223> OTHER INFORMATION: UFV180455

<400> SEQUENCE: 72

Met Lys Ala Ile Ile Val Leu Leu Met Val Val Thr Ser Asn Ala Asp
```

-continued

```
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Glu His Asn Val Ile Asn Ala Thr Asn
            130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Gln Gly Phe Phe Gly Ala Ile
            355                 360                 365

Ala Gly Phe Leu Glu Gly Gly Trp Glu Gly Met Ile Ala Gly Trp Ile
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430
```

-continued

```
Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
    530                 535                 540

Asp Asn His
545
```

```
<210> SEQ ID NO 73
<211> LENGTH: 545
<212> TYPE: PRT
<213> ORGANISM: Artificial Sequence
<220> FEATURE:
<223> OTHER INFORMATION: UFV180456

<400> SEQUENCE: 73

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Glu His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240
```

-continued

```
Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
                290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Gln Gly Phe Phe Gly Ala Ile
                355                 360                 365

Ala Gly Phe Leu Glu Gly Gly Trp Glu Gly Met Ile Ala Gly Trp Ile
                370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Arg Val Leu Leu
                450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
                530                 535                 540

Asp
545

<210> SEQ ID NO 74
<211> LENGTH: 543
<212> TYPE: PRT
<213> ORGANISM: Artificial Sequence
<220> FEATURE:
<223> OTHER INFORMATION: UFV180457

<400> SEQUENCE: 74

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45
```

```
Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Glu His Asn Val Ile Asn Ala Thr Asn
    130             135             140

Ala Pro Gly Gly Pro Tyr Asn Ile Thr Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
    210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
            245             250             255

Glu Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
            275             280             285

Trp Cys Ala Ser Gly Arg Ser Lys Val Ile Lys Gly Ser Leu Pro Leu
    290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
            325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Gln Gly Phe Phe Gly Ala Ile
            355             360             365

Ala Gly Phe Leu Glu Gly Gly Trp Glu Gly Met Ile Ala Gly Trp Ile
    370             375             380

Gly Tyr Thr Ser His Gly Ala His Gly Val Ala Val Ala Ala Asp Leu
385             390             395             400

Lys Ser Thr Gln Glu Ala Ile Asn Lys Ile Thr Lys Asn Leu Asn Ser
            405             410             415

Leu Ser Glu Leu Glu Val Lys Asn Leu Gln Arg Leu Ser Gly Ala Met
            420             425             430

Asp Glu Leu His Asn Glu Ile Leu Glu Leu Asp Glu Lys Val Asp Asp
            435             440             445

Leu Arg Ala Asp Thr Ile Ser Ser Gln Ile Glu Leu Arg Val Leu Leu
    450             455             460
```

-continued

```
Ser Asn Glu Gly Ile Ile Asn Ser Glu Asp Glu Ile Leu Leu Ala Leu
465             470             475             480

Glu Arg Lys Leu Lys Lys Met Leu Gly Pro Ser Ala Val Glu Ile Gly
                485             490             495

Asn Gly Cys Phe Glu Thr Lys His Lys Cys Asn Gln Thr Cys Leu Asp
            500             505             510

Arg Ile Ala Ala Gly Thr Phe Asp Ala Gly Glu Phe Ser Leu Pro Thr
        515             520             525

Phe Asp Ser Leu Asn Ile Thr Ala Ala Ser Leu Asn Asp Asp Gly
    530             535             540
```

<210> SEQ ID NO 75
<211> LENGTH: 541
<212> TYPE: PRT
<213> ORGANISM: Artificial Sequence
<220> FEATURE:
<223> OTHER INFORMATION: UFV180458

<400> SEQUENCE: 75

```
Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
        50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Glu His Asn Val Ile Asn Ala Thr Asn
    130             135             140

Ala Pro Gly Gly Pro Tyr Asn Ile Thr Thr Ser Gly Ser Cys Pro Asn
145             150             155             160

Ile Thr Asn Gly Asn Gly Phe Phe Ala Thr Met Ala Trp Ala Val Pro
            165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
    210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
            245             250             255

Glu Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
    275             280             285
```

```
Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Gln Gly Phe Phe Gly Ala Ile
        355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
        420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp
    530                 535                 540
```

```
<210> SEQ ID NO 76
<211> LENGTH: 539
<212> TYPE: PRT
<213> ORGANISM: Artificial Sequence
<220> FEATURE:
<223> OTHER INFORMATION: UFV180459

<400> SEQUENCE: 76
```

```
Met Lys Ala Ile Ile Val Leu Leu Met Val Val Thr Ser Asn Ala Asp
1                   5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110
```

301

302

```
Met His Asp Arg Thr Lys Ile Arg Gln Leu Pro Asn Leu Leu Arg Gly
        115                 120                 125

Tyr Glu His Ile Arg Leu Ser Glu His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Gln Gly Phe Phe Gly Ala Ile
        355                 360                 365

Ala Gly Phe Leu Glu Gly Gly Trp Glu Gly Met Ile Ala Gly Trp Ile
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
        450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu
```

-continued

```
     530                     535

<210> SEQ ID NO 77
<211> LENGTH: 536
<212> TYPE: PRT
<213> ORGANISM: Artificial Sequence
<220> FEATURE:
<223> OTHER INFORMATION: UFV180460

<400> SEQUENCE: 77

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Glu His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Gln Gly Phe Phe Gly Ala Ile
```

-continued

```
            355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
    515                 520                 525

Phe Asp Ser Leu Asn Ile Thr Ala
    530                 535

<210> SEQ ID NO 78
<211> LENGTH: 534
<212> TYPE: PRT
<213> ORGANISM: Artificial Sequence
<220> FEATURE:
<223> OTHER INFORMATION: UFV180461

<400> SEQUENCE: 78

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
            85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Glu His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
            165                 170                 175

Lys Asn Asp Lys Asn Lys Thr Ala Thr Asn Pro Leu Thr Ile Glu Val
```

```
                 180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Gln Gly Phe Phe Gly Ala Ile
        355                 360                 365

Ala Gly Phe Leu Glu Gly Gly Trp Glu Gly Met Ile Ala Gly Trp Ile
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
        450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
        515                 520                 525

Phe Asp Ser Leu Asn Ile
    530
```

```
<210> SEQ ID NO 79
<211> LENGTH: 532
<212> TYPE: PRT
<213> ORGANISM: Artificial Sequence
<220> FEATURE:
<223> OTHER INFORMATION: UFV180462

<400> SEQUENCE: 79

Met Lys Ala Ile Ile Val Leu Leu Met Val Val Thr Ser Asn Ala Asp
```

-continued

```
1            5              10             15

Arg Ile Cys Thr Gly Ile Thr Ser Ser Asn Ser Pro His Val Val Lys
             20             25             30

Thr Ala Thr Gln Gly Glu Val Asn Val Thr Gly Val Ile Pro Leu Thr
             35             40             45

Thr Thr Pro Thr Lys Ser His Phe Ala Asn Leu Lys Gly Thr Glu Thr
     50             55             60

Arg Gly Lys Leu Cys Pro Lys Cys Leu Asn Cys Thr Asp Leu Asp Val
65             70             75             80

Ala Leu Gly Arg Pro Lys Cys Thr Gly Lys Ile Pro Ser Ala Arg Val
             85             90             95

Ser Ile Leu His Glu Val Arg Pro Val Thr Ser Gly Cys Phe Pro Ile
             100            105            110

Met His Asp Arg Thr Lys Ile Arg Gln Leu Pro Asn Leu Leu Arg Gly
             115            120            125

Tyr Glu His Ile Arg Leu Ser Glu His Asn Val Ile Asn Ala Thr Asn
             130            135            140

Ala Pro Gly Gly Pro Tyr Asn Ile Thr Thr Ser Gly Ser Cys Pro Asn
145            150            155            160

Ile Thr Asn Gly Asn Gly Phe Phe Ala Thr Met Ala Trp Ala Val Pro
             165            170            175

Lys Asn Asp Lys Asn Lys Thr Ala Thr Asn Pro Leu Thr Ile Glu Val
             180            185            190

Pro Tyr Ile Cys Thr Glu Gly Glu Asp Gln Ile Thr Val Trp Gly Phe
             195            200            205

His Ser Asp Asn Glu Thr Gln Met Ala Lys Leu Tyr Gly Asp Ser Lys
     210            215            220

Pro Gln Gln Phe Thr Ser Ser Ala Asn Gly Val Thr Thr Ile Tyr Val
225            230            235            240

Ser Gln Ile Gly Gly Phe Pro Asn Gln Thr Glu Asp Gly Gly Leu Pro
             245            250            255

Glu Ser Gly Arg Ile Val Val Asp Tyr Met Val Gln Lys Ser Gly Lys
             260            265            270

Thr Gly Thr Ile Thr Tyr Gln Arg Gly Ile Leu Leu Pro Gln Lys Val
             275            280            285

Trp Cys Ala Ser Gly Arg Ser Lys Val Ile Lys Gly Ser Leu Pro Leu
     290            295            300

Ile Gly Glu Ala Asp Cys Leu His Glu Lys Tyr Gly Gly Leu Asn Lys
305            310            315            320

Ser Lys Pro Tyr Tyr Thr Gly Glu His Ala Lys Ala Ile Gly Asn Cys
             325            330            335

Pro Ile Trp Val Lys Thr Pro Leu Lys Leu Ala Asn Gly Thr Lys Tyr
             340            345            350

Arg Pro Pro Ala Lys Leu Leu Lys Glu Gln Gly Phe Phe Gly Ala Ile
             355            360            365

Ala Gly Phe Leu Glu Gly Gly Trp Glu Gly Met Ile Ala Gly Trp Ile
             370            375            380

Gly Tyr Thr Ser His Gly Ala His Gly Val Ala Val Ala Ala Asp Leu
385            390            395            400

Lys Ser Thr Gln Glu Ala Ile Asn Lys Ile Thr Lys Asn Leu Asn Ser
             405            410            415

Leu Ser Glu Leu Glu Val Lys Asn Leu Gln Arg Leu Ser Gly Ala Met
             420            425            430
```

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
        450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
        515                 520                 525

Phe Asp Ser Leu
        530

<210> SEQ ID NO 80
<211> LENGTH: 581
<212> TYPE: PRT
<213> ORGANISM: Artificial Sequence
<220> FEATURE:
<223> OTHER INFORMATION: UFV170088

<400> SEQUENCE: 80

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

-continued

```
Gln Ser Gly Arg Ile Val Val Asp Tyr Met Val Gln Lys Ser Gly Lys
            260              265              270

Thr Gly Thr Ile Thr Tyr Gln Arg Gly Ile Leu Leu Pro Gln Lys Val
            275              280              285

Trp Cys Ala Ser Gly Arg Ser Lys Val Ile Lys Gly Ser Leu Pro Leu
            290              295              300

Ile Gly Glu Ala Asp Cys Leu His Glu Lys Tyr Gly Gly Leu Asn Lys
305              310              315              320

Ser Lys Pro Tyr Tyr Thr Gly Glu His Ala Lys Ala Ile Gly Asn Cys
                325              330              335

Pro Ile Trp Val Lys Thr Pro Leu Lys Leu Ala Asn Gly Thr Lys Tyr
            340              345              350

Arg Pro Pro Ala Lys Leu Leu Lys Glu Arg Gly Phe Phe Gly Ala Ile
            355              360              365

Ala Gly Phe Leu Glu Gly Gly Trp Glu Gly Met Ile Ala Gly Trp His
            370              375              380

Gly Tyr Thr Ser His Gly Ala His Gly Val Ala Val Ala Ala Asp Leu
385              390              395              400

Lys Ser Thr Gln Glu Ala Ile Asn Lys Ile Thr Lys Asn Leu Asn Ser
                405              410              415

Leu Ser Glu Leu Glu Val Lys Asn Leu Gln Arg Leu Ser Gly Ala Met
                420              425              430

Asp Glu Leu His Asn Glu Ile Leu Glu Leu Asp Glu Lys Val Asp Asp
            435              440              445

Leu Arg Ala Asp Thr Ile Ser Ser Gln Ile Glu Leu Ala Val Leu Leu
            450              455              460

Ser Asn Glu Gly Ile Ile Asn Ser Glu Asp Glu His Leu Leu Ala Leu
465              470              475              480

Glu Arg Lys Leu Lys Lys Met Leu Gly Pro Ser Ala Val Glu Ile Gly
                485              490              495

Asn Gly Cys Phe Glu Thr Lys His Lys Cys Asn Gln Thr Cys Leu Asp
                500              505              510

Arg Ile Ala Ala Gly Thr Phe Asp Ala Gly Glu Phe Ser Leu Pro Thr
            515              520              525

Phe Asp Ser Leu Asn Ile Thr Ala Ser Gly Ser Leu Val Pro Arg Gly
            530              535              540

Ser Gly Ser Gly Tyr Ile Pro Glu Ala Pro Arg Asp Gly Gln Ala Tyr
545              550              555              560

Val Arg Lys Asp Gly Glu Trp Val Leu Leu Ser Thr Phe Leu Gly Gly
                565              570              575

Ser Glu Pro Glu Ala
            580

<210> SEQ ID NO 81
<211> LENGTH: 548
<212> TYPE: PRT
<213> ORGANISM: Artificial Sequence
<220> FEATURE:
<223> OTHER INFORMATION: UFV180131

<400> SEQUENCE: 81

Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30
```

-continued

```
Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu His Ile Arg Leu Ser Asn His Thr Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
    275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Glu Gly Met Ile Ala Gly Trp Ile Gly Tyr Thr Ser His
    370                 375                 380

Gly Ala His Gly Val Ala Val Ala Ala Asp Leu Lys Ser Thr Gln Glu
385                 390                 395                 400

Ala Ile Asn Lys Ile Thr Lys Asn Leu Asn Ser Leu Ser Glu Leu Glu
                405                 410                 415

Val Lys Asn Leu Gln Arg Leu Ser Gly Ala Met Asp Glu Leu His Asn
            420                 425                 430

Glu Ile Leu Glu Leu Asp Glu Lys Val Asp Asp Leu Arg Ala Asp Thr
            435                 440                 445
```

```
Ile Ser Ser Gln Ile Glu Leu Arg Val Leu Leu Ser Asn Glu Gly Ile
    450             455             460

Ile Asn Ser Glu Asp Glu Ile Leu Leu Ala Leu Glu Arg Lys Leu Lys
465             470             475             480

Lys Met Leu Gly Pro Ser Ala Val Glu Ile Gly Asn Gly Cys Phe Glu
                485             490             495

Thr Lys His Lys Cys Asn Gln Thr Cys Leu Asp Arg Ile Ala Ala Gly
            500             505             510

Thr Phe Asp Ala Gly Glu Phe Ser Leu Pro Thr Phe Asp Ser Leu Asn
            515             520             525

Ile Thr Ala Ala Ser Leu Asn Asp Asp Gly Leu Asp Asn His Thr Ile
    530             535             540

Glu Pro Glu Ala
545

<210> SEQ ID NO 82
<211> LENGTH: 548
<212> TYPE: PRT
<213> ORGANISM: Artificial Sequence
<220> FEATURE:
<223> OTHER INFORMATION: UFV180137

<400> SEQUENCE: 82

Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
                20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
                85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Ile Arg Leu Ser Glu His Asn Val Ile Asn Ala Thr Asn
    130             135             140

Ala Pro Gly Gly Pro Tyr Asn Ile Thr Thr Ser Gly Ser Cys Pro Asn
145             150             155             160

Ile Thr Asn Gly Asn Gly Phe Phe Ala Thr Met Ala Trp Ala Val Pro
                165             170             175

Lys Asn Asp Lys Asn Lys Thr Ala Thr Asn Pro Leu Thr Ile Glu Val
            180             185             190

Pro Tyr Ile Cys Thr Glu Gly Glu Asp Gln Ile Thr Val Trp Gly Phe
            195             200             205

His Ser Asp Asn Glu Thr Gln Met Ala Lys Leu Tyr Gly Asp Ser Lys
    210             215             220

Pro Gln Gln Phe Thr Ser Ser Ala Asn Gly Val Thr Thr Ile Tyr Val
225             230             235             240

Ser Gln Ile Gly Gly Phe Pro Asn Gln Thr Glu Asp Gly Gly Leu Pro
                245             250             255
```

```
Glu Ser Gly Arg Ile Val Val Asp Tyr Met Val Gln Lys Ser Gly Lys
            260             265             270

Thr Gly Thr Ile Thr Tyr Gln Arg Gly Ile Leu Leu Pro Gln Lys Val
        275             280             285

Trp Cys Ala Ser Gly Arg Ser Lys Val Ile Lys Gly Ser Leu Pro Leu
    290             295             300

Ile Gly Glu Ala Asp Cys Leu His Glu Lys Tyr Gly Gly Leu Asn Lys
305             310             315             320

Ser Lys Pro Tyr Tyr Thr Gly Glu His Ala Lys Ala Ile Gly Asn Cys
            325             330             335

Pro Ile Trp Val Lys Thr Pro Leu Lys Leu Ala Asn Gly Thr Lys Tyr
            340             345             350

Arg Pro Pro Ala Lys Leu Leu Lys Glu Arg Gly Phe Phe Gly Ala Ile
        355             360             365

Ala Gly Phe Glu Gly Met Ile Ala Gly Trp Ile Gly Tyr Thr Ser His
    370             375             380

Gly Ala His Gly Val Ala Val Ala Ala Asp Leu Lys Ser Thr Gln Glu
385             390             395             400

Ala Ile Asn Lys Ile Thr Lys Asn Leu Asn Ser Leu Ser Glu Leu Glu
            405             410             415

Val Lys Asn Leu Gln Arg Leu Ser Gly Ala Met Asp Glu Leu His Asn
            420             425             430

Glu Ile Leu Glu Leu Asp Glu Lys Val Asp Asp Leu Arg Ala Asp Thr
        435             440             445

Ile Ser Ser Gln Ile Glu Leu Arg Val Leu Leu Ser Asn Glu Gly Ile
    450             455             460

Ile Asn Ser Glu Asp Glu Ile Leu Leu Ala Leu Glu Arg Lys Leu Lys
465             470             475             480

Lys Met Leu Gly Pro Ser Ala Val Glu Ile Gly Asn Gly Cys Phe Glu
            485             490             495

Thr Lys His Lys Cys Asn Gln Thr Cys Leu Asp Arg Ile Ala Ala Gly
            500             505             510

Thr Phe Asp Ala Gly Glu Phe Ser Leu Pro Thr Phe Asp Ser Leu Asn
        515             520             525

Ile Thr Ala Ala Ser Leu Asn Asp Asp Gly Leu Asp Asn His Thr Ile
    530             535             540

Glu Pro Glu Ala
545

<210> SEQ ID NO 83
<211> LENGTH: 548
<212> TYPE: PRT
<213> ORGANISM: Artificial Sequence
<220> FEATURE:
<223> OTHER INFORMATION: UFV180251

<400> SEQUENCE: 83

Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
        35              40              45

Thr Thr Pro Thr Lys Ser His Phe Ala Asn Leu Lys Gly Thr Glu Thr
    50              55              60
```

-continued

```
Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Glu His Asn Val Ile Asn Ala Thr Asn
        130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Ala Gly Trp Ile Gly Tyr Thr Ser His
        370                 375                 380

Gly Ala His Gly Val Ala Val Ala Ala Asp Leu Lys Ser Thr Gln Glu
385                 390                 395                 400

Ala Ile Asn Lys Ile Thr Lys Asn Leu Asn Ser Leu Ser Glu Leu Glu
            405                 410                 415

Val Lys Asn Leu Gln Arg Leu Ser Gly Ala Met Asp Glu Leu His Asn
            420                 425                 430

Glu Ile Leu Glu Leu Asp Glu Lys Val Asp Asp Leu Arg Ala Asp Thr
        435                 440                 445

Ile Ser Ser Gln Ile Glu Leu Arg Val Leu Leu Ser Asn Glu Gly Ile
        450                 455                 460

Ile Asn Ser Glu Asp Glu Ile Leu Leu Ala Leu Glu Arg Lys Leu Lys
465                 470                 475                 480

Lys Met Leu Gly Pro Ser Ala Val Glu Ile Gly Asn Gly Cys Phe Glu
```

-continued

```
                        485                 490                 495
Thr Lys His Lys Cys Asn Gln Thr Cys Leu Asp Arg Ile Ala Ala Gly
            500                 505                 510

Thr Phe Asp Ala Gly Glu Phe Ser Leu Pro Thr Phe Asp Ser Leu Asn
            515                 520                 525

Ile Thr Ala Ala Ser Leu Asn Asp Asp Gly Leu Asp Asn His Thr Ile
            530                 535                 540

Glu Pro Glu Ala
545

<210> SEQ ID NO 84
<211> LENGTH: 535
<212> TYPE: PRT
<213> ORGANISM: Artificial Sequence
<220> FEATURE:
<223> OTHER INFORMATION: UFV180846

<400> SEQUENCE: 84

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Asn His Thr Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
```

```
      290              295              300

Ile Gly Glu Ala Asp Cys Leu His Glu Lys Tyr Gly Gly Leu Asn Lys
305              310              315              320

Ser Lys Pro Tyr Tyr Thr Gly Glu His Ala Lys Ala Ile Gly Asn Cys
              325              330              335

Pro Ile Trp Val Lys Thr Pro Leu Lys Leu Ala Asn Gly Thr Lys Tyr
              340              345              350

Arg Pro Pro Ala Lys Leu Leu Lys Glu Gln Gly Phe Phe Gly Ala Ile
         355              360              365

Ala Gly Phe Glu Gly Met Ile Ala Gly Trp Ile Gly Tyr Thr Ser His
         370              375              380

Gly Ala His Gly Val Ala Val Ala Ala Asp Leu Lys Ser Thr Gln Glu
385              390              395              400

Ala Ile Asn Lys Ile Thr Lys Asn Leu Asn Ser Leu Ser Glu Leu Glu
              405              410              415

Val Lys Asn Leu Gln Arg Leu Ser Gly Ala Met Asp Glu Leu His Asn
              420              425              430

Glu Ile Leu Glu Leu Asp Glu Lys Val Asp Asp Leu Arg Ala Asp Thr
         435              440              445

Ile Ser Ser Gln Ile Glu Leu Arg Val Leu Leu Ser Asn Glu Gly Ile
         450              455              460

Ile Asn Ser Glu Asp Glu Ile Leu Leu Ala Leu Glu Arg Lys Leu Lys
465              470              475              480

Lys Met Leu Gly Pro Ser Ala Val Glu Ile Gly Asn Gly Cys Phe Glu
              485              490              495

Thr Lys His Lys Cys Asn Gln Thr Cys Leu Asp Arg Ile Ala Ala Gly
              500              505              510

Thr Phe Asp Ala Gly Glu Phe Ser Leu Pro Thr Phe Asp Ser Leu Asn
              515              520              525

Ile Thr Ala Glu Pro Glu Ala
      530              535

<210> SEQ ID NO 85
<211> LENGTH: 6
<212> TYPE: PRT
<213> ORGANISM: Artificial Sequence
<220> FEATURE:
<223> OTHER INFORMATION: His tag

<400> SEQUENCE: 85

His His His His His His
1               5

<210> SEQ ID NO 86
<211> LENGTH: 7
<212> TYPE: PRT
<213> ORGANISM: Artificial Sequence
<220> FEATURE:
<223> OTHER INFORMATION: His tag

<400> SEQUENCE: 86

His His His His His His His
1               5

<210> SEQ ID NO 87
<211> LENGTH: 27
<212> TYPE: PRT
<213> ORGANISM: Artificial Sequence
<220> FEATURE:
```

-continued

```
<223> OTHER INFORMATION: Trimerization domain

<400> SEQUENCE: 87

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 88
<211> LENGTH: 8
<212> TYPE: PRT
<213> ORGANISM: Artificial Sequence
<220> FEATURE:
<223> OTHER INFORMATION: FLAG tag

<400> SEQUENCE: 88

Asp Tyr Lys Asp Asp Asp Asp Lys
1               5

<210> SEQ ID NO 89
<211> LENGTH: 4
<212> TYPE: PRT
<213> ORGANISM: Artificial Sequence
<220> FEATURE:
<223> OTHER INFORMATION: Factor X proteolytic cleavage site

<400> SEQUENCE: 89

Ile Glu Gly Arg
1

<210> SEQ ID NO 90
<211> LENGTH: 6
<212> TYPE: PRT
<213> ORGANISM: Artificial Sequence
<220> FEATURE:
<223> OTHER INFORMATION: Thrombin proteolytic cleavage site

<400> SEQUENCE: 90

Leu Val Pro Arg Gly Ser
1               5

<210> SEQ ID NO 91
<211> LENGTH: 535
<212> TYPE: PRT
<213> ORGANISM: Artificial Sequence
<220> FEATURE:
<223> OTHER INFORMATION: UFV180847

<400> SEQUENCE: 91

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110
```

```
Met His Asp Arg Thr Lys Ile Arg Gln Leu Pro Asn Leu Leu Arg Gly
        115                 120                 125

Tyr Glu His Ile Arg Leu Ser Glu His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
        210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Gln Gly Phe Phe Gly Ala Ile
        355                 360                 365

Ala Gly Phe Glu Gly Met Ile Ala Gly Trp Ile Gly Tyr Thr Ser His
    370                 375                 380

Gly Ala His Gly Val Ala Val Ala Ala Asp Leu Lys Ser Thr Gln Glu
385                 390                 395                 400

Ala Ile Asn Lys Ile Thr Lys Asn Leu Asn Ser Leu Ser Glu Leu Glu
                405                 410                 415

Val Lys Asn Leu Gln Arg Leu Ser Gly Ala Met Asp Glu Leu His Asn
                420                 425                 430

Glu Ile Leu Glu Leu Asp Glu Lys Val Asp Asp Leu Arg Ala Asp Thr
            435                 440                 445

Ile Ser Ser Gln Ile Glu Leu Arg Val Leu Leu Ser Asn Glu Gly Ile
    450                 455                 460

Ile Asn Ser Glu Asp Glu Ile Leu Leu Ala Leu Glu Arg Lys Leu Lys
465                 470                 475                 480

Lys Met Leu Gly Pro Ser Ala Val Glu Ile Gly Asn Gly Cys Phe Glu
                485                 490                 495

Thr Lys His Lys Cys Asn Gln Thr Cys Leu Asp Arg Ile Ala Ala Gly
            500                 505                 510

Thr Phe Asp Ala Gly Glu Phe Ser Leu Pro Thr Phe Asp Ser Leu Asn
            515                 520                 525
```

```
Ile Thr Ala Glu Pro Glu Ala
    530                 535

<210> SEQ ID NO 92
<211> LENGTH: 535
<212> TYPE: PRT
<213> ORGANISM: Artificial Sequence
<220> FEATURE:
<223> OTHER INFORMATION: UFV180848

<400> SEQUENCE: 92

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Glu His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350
```

```
Arg Pro Pro Ala Lys Leu Leu Lys Glu Gln Gly Phe Phe Gly Ala Ile
        355                 360                 365

Ala Gly Phe Leu Glu Gly Gly Ala Gly Trp Ile Gly Tyr Thr Ser His
        370                 375                 380

Gly Ala His Gly Val Ala Val Ala Ala Asp Leu Lys Ser Thr Gln Glu
385                 390                 395                 400

Ala Ile Asn Lys Ile Thr Lys Asn Leu Asn Ser Leu Ser Glu Leu Glu
                405                 410                 415

Val Lys Asn Leu Gln Arg Leu Ser Gly Ala Met Asp Glu Leu His Asn
        420                 425                 430

Glu Ile Leu Glu Leu Asp Glu Lys Val Asp Asp Leu Arg Ala Asp Thr
        435                 440                 445

Ile Ser Ser Gln Ile Glu Leu Arg Val Leu Leu Ser Asn Glu Gly Ile
    450                 455                 460

Ile Asn Ser Glu Asp Glu Ile Leu Leu Ala Leu Glu Arg Lys Leu Lys
465                 470                 475                 480

Lys Met Leu Gly Pro Ser Ala Val Glu Ile Gly Asn Gly Cys Phe Glu
                485                 490                 495

Thr Lys His Lys Cys Asn Gln Thr Cys Leu Asp Arg Ile Ala Ala Gly
        500                 505                 510

Thr Phe Asp Ala Gly Glu Phe Ser Leu Pro Thr Phe Asp Ser Leu Asn
        515                 520                 525

Ile Thr Ala Glu Pro Glu Ala
    530                 535
```

```
<210> SEQ ID NO 93
<211> LENGTH: 540
<212> TYPE: PRT
<213> ORGANISM: Artificial Sequence
<220> FEATURE:
<223> OTHER INFORMATION: UFV180849

<400> SEQUENCE: 93
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
        20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Glu His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175
```

-continued

```
Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Glu Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Gln Gly Phe Phe Gly Ala Ile
            355                 360                 365

Ala Gly Phe Leu Glu Gly Gly Trp Glu Gly Met Ile Ala Gly Trp Ile
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Arg Val Leu Leu
            450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Glu Pro Glu Ala
            530                 535                 540
```

```
<210> SEQ ID NO 94
<211> LENGTH: 584
<212> TYPE: PRT
<213> ORGANISM: Artificial Sequence
<220> FEATURE:
<223> OTHER INFORMATION: Yamagata lineage (B/Florida/04/06)

<400> SEQUENCE: 94
```

-continued

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
            165                 170                 175

Lys Asp Asn Asn Lys Asn Ala Thr Asn Pro Leu Thr Val Glu Val Pro
        180                 185                 190

Tyr Ile Cys Thr Glu Gly Glu Asp Gln Ile Thr Val Trp Gly Phe His
    195                 200                 205

Ser Asp Asp Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
            245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
            325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
            405                 410                 415

Ser Glu Leu Glu Val Lys Asn Leu Gln Arg Leu Ser Gly Ala Met Asp
```

-continued

```
                 420              425              430
Glu Leu His Asn Glu Ile Leu Glu Leu Asp Glu Lys Val Asp Asp Leu
        435              440              445
Arg Ala Asp Thr Ile Ser Ser Gln Ile Glu Leu Ala Val Leu Leu Ser
    450              455              460
Asn Glu Gly Ile Ile Asn Ser Glu Asp Glu His Leu Leu Ala Leu Glu
465              470              475              480
Arg Lys Leu Lys Lys Met Leu Gly Pro Ser Ala Val Glu Ile Gly Asn
            485              490              495
Gly Cys Phe Glu Thr Lys His Lys Cys Asn Gln Thr Cys Leu Asp Arg
            500              505              510
Ile Ala Ala Gly Thr Phe Asn Ala Gly Glu Phe Ser Leu Pro Thr Phe
            515              520              525
Asp Ser Leu Asn Ile Thr Ala Ala Ser Leu Asn Asp Asp Gly Leu Asp
        530              535              540
Asn His Thr Ile Leu Leu Tyr Tyr Ser Thr Ala Ala Ser Ser Leu Ala
545              550              555              560
Val Thr Leu Met Leu Ala Ile Phe Ile Val Tyr Met Val Ser Arg Asp
            565              570              575
Asn Val Ser Cys Ser Ile Cys Leu
            580

<210> SEQ ID NO 95
<211> LENGTH: 548
<212> TYPE: PRT
<213> ORGANISM: Artificial Sequence
<220> FEATURE:
<223> OTHER INFORMATION: Consensus Sequence

<400> SEQUENCE: 95

Met Lys Ala Ile Ile Val Leu Leu Met Val Val Thr Ser Asn Ala Asp
1               5               10              15
Arg Ile Cys Thr Gly Ile Thr Ser Ser Asn Ser Pro His Val Val Lys
            20              25              30
Thr Ala Thr Gln Gly Glu Val Asn Val Thr Gly Val Ile Pro Leu Thr
        35              40              45
Thr Thr Pro Thr Lys Ser Tyr Phe Ala Asn Leu Lys Gly Thr Glu Thr
    50              55              60
Arg Gly Lys Leu Cys Pro Asp Cys Leu Asn Cys Thr Asp Leu Asp Val
65              70              75              80
Ala Leu Gly Arg Pro Met Cys Val Gly Thr Thr Pro Ser Ala Lys Ala
            85              90              95
Ser Ile Leu His Glu Val Arg Pro Val Thr Ser Gly Cys Phe Pro Ile
            100             105             110
Met His Asp Arg Thr Lys Ile Arg Gln Leu Pro Asn Leu Leu Arg Gly
            115             120             125
Tyr Glu His Ile Arg Leu Ser Thr Gln Asn Val Ile Asp Ala Glu Lys
        130             135             140
Ala Pro Gly Gly Pro Tyr Arg Leu Gly Thr Ser Gly Ser Cys Pro Asn
145             150             155             160
Ala Thr Ser Lys Asn Gly Phe Phe Ala Thr Met Ala Trp Ala Val Pro
            165             170             175
Lys Asp Asn Asn Lys Asn Ala Thr Asn Pro Leu Thr Val Glu Val Pro
            180             185             190
Tyr Ile Cys Thr Glu Gly Glu Asp Gln Ile Thr Val Trp Gly Phe His
```

-continued

```
                195                 200                 205

Ser Asp Asn Lys Thr Gln Met Lys Lys Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
                260                 265                 270

Gly Thr Ile Val Tyr Gln Arg Gly Val Leu Leu Pro Gln Lys Val Trp
                275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
                420                 425                 430

Glu Leu His Asn Glu Ile Leu Glu Leu Asp Glu Lys Val Asp Asp Leu
                435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
                500                 505                 510

Ile Ala Ala Gly Thr Phe Asn Ala Gly Glu Phe Ser Leu Pro Thr Phe
                515                 520                 525

Asp Ser Leu Asn Ile Thr Ala Ala Ser Leu Asn Asp Asp Gly Leu Asp
    530                 535                 540

Asn His Thr Ile
545

<210> SEQ ID NO 96
<211> LENGTH: 556
<212> TYPE: PRT
<213> ORGANISM: Artificial Sequence
<220> FEATURE:
<223> OTHER INFORMATION: UFV172551

<400> SEQUENCE: 96

Met Lys Ala Ile Ile Val Leu Leu Met Val Val Thr Ser Asn Ala Asp
```

-continued

```
1                5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Thr Asn
    130                 135                 140

Ala Pro Gly Gly Pro Tyr Asn Ile Thr Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
    210                 215                 220

Pro Gln Gln Phe Thr Ser Ser Ala Asn Gly Val Thr Thr Ile Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp Ile
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430
```

```
Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Arg Val Leu Leu
    450                 455                 460

Ser Asn Glu Gly Ile Ile Asn Ser Glu Asp Glu Ile Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
        530                 535                 540

Asp Asn His Thr Ile Gly Gly Ser Glu Pro Glu Ala
545                 550                 555
```

```
<210> SEQ ID NO 97
<211> LENGTH: 516
<212> TYPE: PRT
<213> ORGANISM: Artificial Sequence
<220> FEATURE:
<223> OTHER INFORMATION: UFV180846 Secreted

<400> SEQUENCE: 97
```

```
Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
        20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
                100                 105                 110

Gly Tyr Glu His Ile Arg Leu Ser Asn His Thr Val Ile Asn Ala Thr
        115                 120                 125

Asn Ala Pro Gly Gly Pro Tyr Asn Ile Thr Thr Ser Gly Ser Cys Pro
        130                 135                 140

Asn Ile Thr Asn Gly Asn Gly Phe Phe Ala Thr Met Ala Trp Ala Val
145                 150                 155                 160

Pro Lys Asn Asp Lys Asn Lys Thr Ala Thr Asn Pro Leu Thr Ile Glu
                165                 170                 175

Val Pro Tyr Ile Cys Thr Glu Gly Glu Asp Gln Ile Thr Val Trp Gly
                180                 185                 190

Phe His Ser Asp Asn Glu Thr Gln Met Ala Lys Leu Tyr Gly Asp Ser
        195                 200                 205

Lys Pro Gln Gln Phe Thr Ser Ser Ala Asn Gly Val Thr Thr Ile Tyr
        210                 215                 220

Val Ser Gln Ile Gly Gly Phe Pro Asn Gln Thr Glu Asp Gly Gly Leu
225                 230                 235                 240
```

-continued

```
Pro Glu Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
                260                 265                 270

Val Trp Cys Ala Ser Gly Arg Ser Lys Val Ile Lys Gly Ser Leu Pro
                275                 280                 285

Leu Ile Gly Glu Ala Asp Cys Leu His Glu Lys Tyr Gly Gly Leu Asn
            290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Gln Gly Phe Phe Gly Ala
                340                 345                 350

Ile Ala Gly Phe Glu Gly Met Ile Ala Gly Trp Ile Gly Tyr Thr Ser
                355                 360                 365

His Gly Ala His Gly Val Ala Val Ala Ala Asp Leu Lys Ser Thr Gln
            370                 375                 380

Glu Ala Ile Asn Lys Ile Thr Lys Asn Leu Asn Ser Leu Ser Glu Leu
385                 390                 395                 400

Glu Val Lys Asn Leu Gln Arg Leu Ser Gly Ala Met Asp Glu Leu His
                405                 410                 415

Asn Glu Ile Leu Glu Leu Asp Glu Lys Val Asp Asp Leu Arg Ala Asp
                420                 425                 430

Thr Ile Ser Ser Gln Ile Glu Leu Arg Val Leu Leu Ser Asn Glu Gly
            435                 440                 445

Ile Ile Asn Ser Glu Asp Glu Ile Leu Leu Ala Leu Glu Arg Lys Leu
            450                 455                 460

Lys Lys Met Leu Gly Pro Ser Ala Val Glu Ile Gly Asn Gly Cys Phe
465                 470                 475                 480

Glu Thr Lys His Lys Cys Asn Gln Thr Cys Leu Asp Arg Ile Ala Ala
                485                 490                 495

Gly Thr Phe Asp Ala Gly Glu Phe Ser Leu Pro Thr Phe Asp Ser Leu
                500                 505                 510

Asn Ile Thr Ala
            515
```

```
<210> SEQ ID NO 98
<211> LENGTH: 516
<212> TYPE: PRT
<213> ORGANISM: Artificial Sequence
<220> FEATURE:
<223> OTHER INFORMATION: UFV180847 Secreted

<400> SEQUENCE: 98

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
                20                  25                  30

Thr Thr Thr Pro Thr Lys Ser His Phe Ala Asn Leu Lys Gly Thr Glu
            35                  40                  45

Thr Arg Gly Lys Leu Cys Pro Lys Cys Leu Asn Cys Thr Asp Leu Asp
            50                  55                  60

Val Ala Leu Gly Arg Pro Lys Cys Thr Gly Lys Ile Pro Ser Ala Arg
65                  70                  75                  80
```

-continued

```
Val Ser Ile Leu His Glu Val Arg Pro Val Thr Ser Gly Cys Phe Pro
              85                  90                  95

Ile Met His Asp Arg Thr Lys Ile Arg Gln Leu Pro Asn Leu Leu Arg
             100                 105                 110

Gly Tyr Glu His Ile Arg Leu Ser Glu His Asn Val Ile Asn Ala Thr
             115                 120                 125

Asn Ala Pro Gly Gly Pro Tyr Asn Ile Thr Thr Ser Gly Ser Cys Pro
         130                 135                 140

Asn Ile Thr Asn Gly Asn Gly Phe Phe Ala Thr Met Ala Trp Ala Val
145                 150                 155                 160

Pro Lys Asn Asp Lys Asn Lys Thr Ala Thr Asn Pro Leu Thr Ile Glu
                 165                 170                 175

Val Pro Tyr Ile Cys Thr Glu Gly Glu Asp Gln Ile Thr Val Trp Gly
             180                 185                 190

Phe His Ser Asp Asn Glu Thr Gln Met Ala Lys Leu Tyr Gly Asp Ser
             195                 200                 205

Lys Pro Gln Gln Phe Thr Ser Ser Ala Asn Gly Val Thr Thr Ile Tyr
         210                 215                 220

Val Ser Gln Ile Gly Gly Phe Pro Asn Gln Thr Glu Asp Gly Gly Leu
225                 230                 235                 240

Pro Glu Ser Gly Arg Ile Val Val Asp Tyr Met Val Gln Lys Ser Gly
             245                 250                 255

Lys Thr Gly Thr Ile Thr Tyr Gln Arg Gly Ile Leu Leu Pro Gln Lys
             260                 265                 270

Val Trp Cys Ala Ser Gly Arg Ser Lys Val Ile Lys Gly Ser Leu Pro
             275                 280                 285

Leu Ile Gly Glu Ala Asp Cys Leu His Glu Lys Tyr Gly Gly Leu Asn
         290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
             325                 330                 335

Tyr Arg Pro Pro Ala Lys Leu Leu Lys Glu Gln Gly Phe Phe Gly Ala
             340                 345                 350

Ile Ala Gly Phe Glu Gly Met Ile Ala Gly Trp Ile Gly Tyr Thr Ser
             355                 360                 365

His Gly Ala His Gly Val Ala Val Ala Ala Asp Leu Lys Ser Thr Gln
         370                 375                 380

Glu Ala Ile Asn Lys Ile Thr Lys Asn Leu Asn Ser Leu Ser Glu Leu
385                 390                 395                 400

Glu Val Lys Asn Leu Gln Arg Leu Ser Gly Ala Met Asp Glu Leu His
             405                 410                 415

Asn Glu Ile Leu Glu Leu Asp Glu Lys Val Asp Asp Leu Arg Ala Asp
             420                 425                 430

Thr Ile Ser Ser Gln Ile Glu Leu Arg Val Leu Leu Ser Asn Glu Gly
         435                 440                 445

Ile Ile Asn Ser Glu Asp Glu Ile Leu Leu Ala Leu Glu Arg Lys Leu
         450                 455                 460

Lys Lys Met Leu Gly Pro Ser Ala Val Glu Ile Gly Asn Gly Cys Phe
465                 470                 475                 480

Glu Thr Lys His Lys Cys Asn Gln Thr Cys Leu Asp Arg Ile Ala Ala
             485                 490                 495
```

-continued

```
Gly Thr Phe Asp Ala Gly Glu Phe Ser Leu Pro Thr Phe Asp Ser Leu
            500                 505                 510

Asn Ile Thr Ala
        515

<210> SEQ ID NO 99
<211> LENGTH: 516
<212> TYPE: PRT
<213> ORGANISM: Artificial Sequence
<220> FEATURE:
<223> OTHER INFORMATION: UFV180848 Secreted

<400> SEQUENCE: 99

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
            35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
                100                 105                 110

Gly Tyr Glu His Ile Arg Leu Ser Glu His Asn Val Ile Asn Ala Thr
            115                 120                 125

Asn Ala Pro Gly Gly Pro Tyr Asn Ile Thr Thr Ser Gly Ser Cys Pro
            130                 135                 140

Asn Ile Thr Asn Gly Asn Gly Phe Phe Ala Thr Met Ala Trp Ala Val
145                 150                 155                 160

Pro Lys Asn Asp Lys Asn Lys Thr Ala Thr Asn Pro Leu Thr Ile Glu
                165                 170                 175

Val Pro Tyr Ile Cys Thr Glu Gly Glu Asp Gln Ile Thr Val Trp Gly
                180                 185                 190

Phe His Ser Asp Asn Glu Thr Gln Met Ala Lys Leu Tyr Gly Asp Ser
            195                 200                 205

Lys Pro Gln Gln Phe Thr Ser Ser Ala Asn Gly Val Thr Thr Ile Tyr
    210                 215                 220

Val Ser Gln Ile Gly Gly Phe Pro Asn Gln Thr Glu Asp Gly Gly Leu
225                 230                 235                 240

Pro Glu Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
            275                 280                 285

Leu Ile Gly Glu Ala Asp Cys Leu His Glu Lys Tyr Gly Gly Leu Asn
    290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335
```

-continued

```
Tyr Arg Pro Pro Ala Lys Leu Leu Lys Glu Gln Gly Phe Phe Gly Ala
            340             345             350

Ile Ala Gly Phe Leu Glu Gly Gly Ala Gly Trp Ile Gly Tyr Thr Ser
        355             360             365

His Gly Ala His Gly Val Ala Val Ala Ala Asp Leu Lys Ser Thr Gln
        370             375             380

Glu Ala Ile Asn Lys Ile Thr Lys Asn Leu Asn Ser Leu Ser Glu Leu
385             390             395             400

Glu Val Lys Asn Leu Gln Arg Leu Ser Gly Ala Met Asp Glu Leu His
            405             410             415

Asn Glu Ile Leu Glu Leu Asp Glu Lys Val Asp Asp Leu Arg Ala Asp
            420             425             430

Thr Ile Ser Ser Gln Ile Glu Leu Arg Val Leu Leu Ser Asn Glu Gly
        435             440             445

Ile Ile Asn Ser Glu Asp Glu Ile Leu Leu Ala Leu Glu Arg Lys Leu
        450             455             460

Lys Lys Met Leu Gly Pro Ser Ala Val Glu Ile Gly Asn Gly Cys Phe
465             470             475             480

Glu Thr Lys His Lys Cys Asn Gln Thr Cys Leu Asp Arg Ile Ala Ala
            485             490             495

Gly Thr Phe Asp Ala Gly Glu Phe Ser Leu Pro Thr Phe Asp Ser Leu
            500             505             510

Asn Ile Thr Ala
        515
```

```
<210> SEQ ID NO 100
<211> LENGTH: 521
<212> TYPE: PRT
<213> ORGANISM: Artificial Sequence
<220> FEATURE:
<223> OTHER INFORMATION: UFV180849 Secreted

<400> SEQUENCE: 100

Asp Arg Ile Cys Thr Gly Ile Thr Ser Ser Asn Ser Pro His Val Val
1               5               10              15

Lys Thr Ala Thr Gln Gly Glu Val Asn Val Thr Gly Val Ile Pro Leu
            20              25              30

Thr Thr Thr Pro Thr Lys Ser His Phe Ala Asn Leu Lys Gly Thr Glu
        35              40              45

Thr Arg Gly Lys Leu Cys Pro Lys Cys Leu Asn Cys Thr Asp Leu Asp
    50              55              60

Val Ala Leu Gly Arg Pro Lys Cys Thr Gly Lys Ile Pro Ser Ala Arg
65              70              75              80

Val Ser Ile Leu His Glu Val Arg Pro Val Thr Ser Gly Cys Phe Pro
            85              90              95

Ile Met His Asp Arg Thr Lys Ile Arg Gln Leu Pro Asn Leu Leu Arg
            100             105             110

Gly Tyr Glu His Ile Arg Leu Ser Glu His Asn Val Ile Asn Ala Thr
        115             120             125

Asn Ala Pro Gly Gly Pro Tyr Asn Ile Thr Thr Ser Gly Ser Cys Pro
        130             135             140

Asn Ile Thr Asn Gly Asn Gly Phe Phe Ala Thr Met Ala Trp Ala Val
145             150             155             160

Pro Lys Asn Asp Lys Asn Lys Thr Ala Thr Asn Pro Leu Thr Ile Glu
            165             170             175
```

-continued

```
Val Pro Tyr Ile Cys Thr Glu Gly Glu Asp Gln Ile Thr Val Trp Gly
            180                 185                 190

Phe His Ser Asp Asn Glu Thr Gln Met Ala Lys Leu Tyr Gly Asp Ser
            195                 200                 205

Lys Pro Gln Gln Phe Thr Ser Ser Ala Asn Gly Val Thr Thr Ile Tyr
        210                 215                 220

Val Ser Gln Ile Gly Gly Phe Pro Asn Gln Thr Glu Asp Gly Gly Leu
225                 230                 235                 240

Pro Glu Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
            275                 280                 285

Leu Ile Gly Glu Ala Asp Cys Leu His Glu Lys Tyr Gly Gly Leu Asn
        290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Gln Gly Phe Phe Gly Ala
            340                 345                 350

Ile Ala Gly Phe Leu Glu Gly Gly Trp Glu Gly Met Ile Ala Gly Trp
        355                 360                 365

Ile Gly Tyr Thr Ser His Gly Ala His Gly Val Ala Val Ala Ala Asp
        370                 375                 380

Leu Lys Ser Thr Gln Glu Ala Ile Asn Lys Ile Thr Lys Asn Leu Asn
385                 390                 395                 400

Ser Leu Ser Glu Leu Glu Val Lys Asn Leu Gln Arg Leu Ser Gly Ala
                405                 410                 415

Met Asp Glu Leu His Asn Glu Ile Leu Glu Leu Asp Glu Lys Val Asp
            420                 425                 430

Asp Leu Arg Ala Asp Thr Ile Ser Ser Gln Ile Glu Leu Arg Val Leu
            435                 440                 445

Leu Ser Asn Glu Gly Ile Ile Asn Ser Glu Asp Glu Ile Leu Leu Ala
        450                 455                 460

Leu Glu Arg Lys Leu Lys Lys Met Leu Gly Pro Ser Ala Val Glu Ile
465                 470                 475                 480

Gly Asn Gly Cys Phe Glu Thr Lys His Lys Cys Asn Gln Thr Cys Leu
                485                 490                 495

Asp Arg Ile Ala Ala Gly Thr Phe Asp Ala Gly Glu Phe Ser Leu Pro
            500                 505                 510

Thr Phe Asp Ser Leu Asn Ile Thr Ala
            515                 520
```

```
<210> SEQ ID NO 101
<211> LENGTH: 541
<212> TYPE: PRT
<213> ORGANISM: Artificial Sequence
<220> FEATURE:
<223> OTHER INFORMATION: UFV180567

<400> SEQUENCE: 101
```

```
Met Lys Ala Ile Ile Val Leu Leu Met Val Val Thr Ser Asn Ala Asp
1               5                   10                  15
```

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Arg Ser His Phe Ala Asn Leu Lys Gly Thr Gln Thr
        50                  55                  60

Arg Gly Lys Leu Cys Pro Asn Cys Phe Asn Cys Thr Asp Leu Asp Val
65                  70                  75                  80

Ala Leu Gly Arg Pro Lys Cys Met Gly Asn Ile Pro Ser Ala Lys Val
                85                  90                  95

Ser Ile Leu His Glu Val Lys Pro Val Thr Ser Gly Cys Phe Pro Ile
                100                 105                 110

Met His Asp Arg Thr Lys Ile Arg Gln Leu Pro Asn Leu Leu Arg Gly
        115                 120                 125

Tyr Glu Asn Ile Arg Leu Ser Thr Ser Asn Val Ile Asn Ala Glu Thr
        130                 135                 140

Ala Pro Gly Gly Pro Tyr Lys Val Gly Thr Ser Gly Ser Cys Pro Asn
145                 150                 155                 160

Val Ala Asn Arg Asn Gly Phe Phe Asn Thr Met Ala Trp Val Ile Pro
                165                 170                 175

Lys Asp Asn Asn Lys Thr Ala Ile Asn Pro Val Thr Val Glu Val Pro
                180                 185                 190

Tyr Ile Cys Ser Glu Gly Glu Asp Gln Ile Thr Val Trp Gly Phe His
                195                 200                 205

Ser Asp Asp Lys Thr Gln Met Glu Arg Leu Tyr Gly Asp Ser Asn Pro
        210                 215                 220

Gln Lys Phe Thr Ser Ser Ala Asn Gly Val Thr Thr His Tyr Val Ser
225                 230                 235                 240

Gln Ile Gly Gly Phe Pro Asn Gln Thr Glu Asp Glu Gly Leu Lys Gln
                245                 250                 255

Ser Gly Arg Ile Val Val Asp Tyr Met Val Gln Lys Pro Gly Lys Thr
                260                 265                 270

Gly Thr Ile Val Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
        290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
        370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asn
                420                 425                 430

Gly Leu His Asp Glu Ile Leu Glu Leu Asp Glu Lys Val Asp Asp Leu

-continued

```
          435              440              445

Arg Ala Asp Thr Ile Ser Ser Gln Ile Glu Leu Ala Val Leu Leu Ser
    450              455              460

Asn Glu Gly Ile Ile Asn Ser Glu Asp Glu His Leu Leu Ala Leu Glu
465              470              475              480

Arg Lys Leu Lys Lys Met Leu Gly Pro Ser Ala Val Glu Ile Gly Asn
                485              490              495

Gly Cys Phe Glu Thr Lys His Lys Cys Asn Gln Thr Cys Leu Asp Arg
            500              505              510

Ile Ala Ala Gly Thr Phe Asn Ala Gly Asp Phe Ser Leu Pro Thr Phe
            515              520              525

Asp Ser Leu Asn Ile Thr Ala His His His His His His
    530              535              540

<210> SEQ ID NO 102
<211> LENGTH: 553
<212> TYPE: PRT
<213> ORGANISM: Artificial Sequence
<220> FEATURE:
<223> OTHER INFORMATION: UFV180566

<400> SEQUENCE: 102

Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Arg Ser His Phe Ala Asn Leu Lys Gly Thr Gln Thr
    50              55              60

Arg Gly Lys Leu Cys Pro Asn Cys Phe Asn Cys Thr Asp Leu Asp Val
65              70              75              80

Ala Leu Gly Arg Pro Lys Cys Met Gly Asn Ile Pro Ser Ala Lys Val
            85              90              95

Ser Ile Leu His Glu Val Lys Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu Asn Ile Arg Leu Ser Thr Ser Asn Val Ile Asn Ala Glu Thr
    130             135             140

Ala Pro Gly Gly Pro Tyr Lys Val Gly Thr Ser Gly Ser Cys Pro Asn
145             150             155             160

Val Ala Asn Arg Asn Gly Phe Phe Asn Thr Met Ala Trp Val Ile Pro
            165             170             175

Lys Asp Asn Asn Lys Thr Ala Ile Asn Pro Val Thr Val Glu Val Pro
            180             185             190

Tyr Ile Cys Ser Glu Gly Glu Asp Gln Ile Thr Val Trp Gly Phe His
            195             200             205

Ser Asp Asp Lys Thr Gln Met Glu Arg Leu Tyr Gly Asp Ser Asn Pro
    210             215             220

Gln Gln Phe Thr Ser Ser Ala Asn Gly Val Thr Thr Ile Tyr Val Ser
225             230             235             240

Gln Ile Gly Gly Phe Pro Asn Gln Thr Glu Asp Glu Gly Leu Lys Gln
                245             250             255

Ser Gly Arg Ile Val Val Asp Tyr Met Val Gln Lys Pro Gly Lys Thr
```

-continued

```
                260             265             270
Gly Thr Ile Val Tyr Gln Arg Gly Ile Leu Leu Pro Gln Lys Val Trp
            275             280             285
Cys Ala Ser Gly Arg Ser Lys Val Ile Lys Gly Ser Leu Pro Leu Ile
    290             295             300
Gly Glu Ala Asp Cys Leu His Glu Lys Tyr Gly Gly Leu Asn Lys Ser
305             310             315             320
Lys Pro Tyr Tyr Thr Gly Glu His Ala Lys Ala Ile Gly Asn Cys Pro
            325             330             335
Ile Trp Val Lys Thr Pro Leu Lys Leu Ala Asn Gly Thr Lys Tyr Arg
            340             345             350
Pro Pro Ala Lys Leu Leu Lys Glu Arg Gly Phe Phe Gly Ala Ile Ala
            355             360             365
Gly Phe Glu Gly Met Ile Ala Gly Trp Ile Gly Tyr Thr Ser His Gly
    370             375             380
Ala His Gly Val Ala Val Ala Ala Asp Leu Lys Ser Thr Gln Glu Ala
385             390             395             400
Ile Asn Lys Ile Thr Lys Asn Leu Asn Ser Leu Ser Glu Leu Glu Val
            405             410             415
Lys Asn Leu Gln Arg Leu Ser Gly Ala Met Asn Gly Leu His Asp Glu
            420             425             430
Ile Leu Glu Leu Asp Glu Lys Val Asp Asp Leu Arg Ala Asp Thr Ile
            435             440             445
Ser Ser Gln Ile Glu Leu Arg Val Leu Leu Ser Asn Glu Gly Ile Ile
    450             455             460
Asn Ser Glu Asp Glu Ile Leu Leu Ala Leu Glu Arg Lys Leu Lys Lys
465             470             475             480
Met Leu Gly Pro Ser Ala Val Glu Ile Gly Asn Gly Cys Phe Glu Thr
            485             490             495
Lys His Lys Cys Asn Gln Thr Cys Leu Asp Arg Ile Ala Ala Gly Thr
            500             505             510
Phe Asn Ala Gly Asp Phe Ser Leu Pro Thr Phe Asp Ser Leu Asn Ile
            515             520             525
Thr Ala Ser Gly Ser Leu Val Pro Ser Gly Ser Leu Pro Glu Thr Gly
    530             535             540
Gly Gly Ser His His His His His His
545             550
```

```
<210> SEQ ID NO 103
<211> LENGTH: 540
<212> TYPE: PRT
<213> ORGANISM: Artificial Sequence
<220> FEATURE:
<223> OTHER INFORMATION: UFV180565

<400> SEQUENCE: 103
```

```
Met Lys Ala Ile Ile Val Leu Leu Met Val Val Thr Ser Asn Ala Asp
1               5               10              15
Arg Ile Cys Thr Gly Ile Thr Ser Ser Asn Ser Pro His Val Val Lys
            20              25              30
Thr Ala Thr Gln Gly Glu Val Asn Val Thr Gly Val Ile Pro Leu Thr
            35              40              45
Thr Thr Pro Thr Lys Ser His Phe Ala Asn Leu Lys Gly Thr Lys Thr
    50              55              60
Arg Gly Lys Leu Cys Pro Asn Cys Leu Asn Cys Thr Asp Leu Asp Val
```

-continued

```
65              70              75              80

Ala Leu Gly Arg Pro Met Cys Met Gly Thr Ile Pro Ser Ala Lys Ala
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu Asn Ile Arg Leu Ser Thr His Asn Val Ile Asn Ala Glu Arg
        130             135             140

Ala Pro Gly Gly Pro Tyr Arg Leu Gly Thr Ser Gly Ser Cys Pro Asn
145             150             155             160

Val Thr Ser Arg Asn Gly Phe Phe Ala Thr Met Ala Trp Ala Val Pro
            165             170             175

Arg Asp Asn Lys Thr Ala Thr Asn Pro Leu Thr Val Glu Val Pro Tyr
            180             185             190

Ile Cys Thr Lys Gly Glu Asp Gln Ile Thr Val Trp Gly Phe His Ser
            195             200             205

Asp Asp Lys Thr Gln Met Lys Asn Leu Tyr Gly Asp Ser Asn Pro Gln
        210             215             220

Lys Phe Thr Ser Ser Ala Asn Gly Val Thr Thr His Tyr Val Ser Gln
225             230             235             240

Ile Gly Asp Phe Pro Asn Gln Thr Glu Asp Gly Gly Leu Pro Gln Ser
            245             250             255

Gly Arg Ile Val Val Asp Tyr Met Val Gln Lys Pro Gly Lys Thr Gly
            260             265             270

Thr Ile Val Tyr Gln Arg Gly Val Leu Leu Pro Gln Lys Val Trp Cys
            275             280             285

Ala Ser Gly Arg Ser Lys Val Ile Lys Gly Ser Leu Pro Leu Ile Gly
            290             295             300

Glu Ala Asp Cys Leu His Glu Lys Tyr Gly Gly Leu Asn Lys Ser Lys
305             310             315             320

Pro Tyr Tyr Thr Gly Glu His Ala Lys Ala Ile Gly Asn Cys Pro Ile
            325             330             335

Trp Val Lys Thr Pro Leu Lys Leu Ala Asn Gly Thr Lys Tyr Arg Pro
            340             345             350

Pro Ala Lys Leu Leu Lys Glu Arg Gly Phe Phe Gly Ala Ile Ala Gly
            355             360             365

Phe Leu Glu Gly Gly Trp Glu Gly Met Ile Ala Gly Trp His Gly Tyr
        370             375             380

Thr Ser His Gly Ala His Gly Val Ala Val Ala Ala Asp Leu Lys Ser
385             390             395             400

Thr Gln Glu Ala Ile Asn Lys Ile Thr Lys Asn Leu Asn Ser Leu Ser
            405             410             415

Glu Leu Glu Val Lys Asn Leu Gln Arg Leu Ser Gly Ala Met Asp Glu
            420             425             430

Leu His Asn Glu Ile Leu Glu Leu Asp Glu Lys Val Asp Asp Leu Arg
        435             440             445

Ala Asp Thr Ile Ser Ser Gln Ile Glu Leu Ala Val Leu Leu Ser Asn
        450             455             460

Glu Gly Ile Ile Asn Ser Glu Asp Glu His Leu Leu Ala Leu Glu Arg
465             470             475             480

Lys Leu Lys Lys Met Leu Gly Pro Ser Ala Val Asp Ile Gly Asn Gly
            485             490             495
```

```
Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
            515                 520                 525

Ser Leu Asn Ile Thr Ala His His His His His His
            530                 535                 540

<210> SEQ ID NO 104
<211> LENGTH: 552
<212> TYPE: PRT
<213> ORGANISM: Artificial Sequence
<220> FEATURE:
<223> OTHER INFORMATION: UFV180400

<400> SEQUENCE: 104

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Lys Thr
            50                  55                  60

Arg Gly Lys Leu Cys Pro Asn Cys Leu Asn Cys Thr Asp Leu Asp Val
65                  70                  75                  80

Ala Leu Gly Arg Pro Met Cys Met Gly Thr Ile Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu Asn Ile Arg Leu Ser Thr His Asn Val Ile Asn Ala Glu Arg
            130                 135                 140

Ala Pro Gly Gly Pro Tyr Arg Leu Gly Thr Ser Gly Ser Cys Pro Asn
145                 150                 155                 160

Val Thr Ser Arg Asn Gly Phe Phe Ala Thr Met Ala Trp Ala Val Pro
            165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
            195                 200                 205

Asp Asp Lys Thr Gln Met Lys Asn Leu Tyr Gly Asp Ser Asn Pro Gln
            210                 215                 220

Gln Phe Thr Ser Ser Ala Asn Gly Val Thr Thr Ile Tyr Val Ser Gln
225                 230                 235                 240

Ile Gly Asp Phe Pro Asn Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
            275                 280                 285

Ala Ser Gly Arg Ser Lys Val Ile Lys Gly Ser Leu Pro Leu Ile Gly
            290                 295                 300

Glu Ala Asp Cys Leu His Glu Lys Tyr Gly Gly Leu Asn Lys Ser Lys
305                 310                 315                 320
```

-continued

```
Pro Tyr Tyr Thr Gly Glu His Ala Lys Ala Ile Gly Asn Cys Pro Ile
            325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
            355                 360                 365

Phe Glu Gly Met Ile Ala Gly Trp Ile Gly Tyr Thr Ser His Gly Ala
    370                 375                 380

His Gly Val Ala Val Ala Ala Asp Leu Lys Ser Thr Gln Glu Ala Ile
385                 390                 395                 400

Asn Lys Ile Thr Lys Asn Leu Asn Ser Leu Ser Glu Leu Glu Val Lys
                405                 410                 415

Asn Leu Gln Arg Leu Ser Gly Ala Met Asp Glu Leu His Asn Glu Ile
            420                 425                 430

Leu Glu Leu Asp Glu Lys Val Asp Asp Leu Arg Ala Asp Thr Ile Ser
            435                 440                 445

Ser Gln Ile Glu Leu Arg Val Leu Leu Ser Asn Glu Gly Ile Ile Asn
    450                 455                 460

Ser Glu Asp Glu Ile Leu Leu Ala Leu Glu Arg Lys Leu Lys Lys Met
465                 470                 475                 480

Leu Gly Pro Ser Ala Val Asp Ile Gly Asn Gly Cys Phe Glu Thr Lys
            485                 490                 495

His Lys Cys Asn Gln Thr Cys Leu Asp Arg Ile Ala Ala Gly Thr Phe
            500                 505                 510

Asn Ala Gly Glu Phe Ser Leu Pro Thr Phe Asp Ser Leu Asn Ile Thr
            515                 520                 525

Ala Ser Gly Ser Leu Val Pro Ser Gly Ser Leu Pro Glu Thr Gly Gly
    530                 535                 540

Gly Ser His His His His His His
545                 550
```

```
<210> SEQ ID NO 105
<211> LENGTH: 541
<212> TYPE: PRT
<213> ORGANISM: Artificial Sequence
<220> FEATURE:
<223> OTHER INFORMATION: UFV180571

<400> SEQUENCE: 105
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
            85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125
```

```
Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
                180                 185                 190

Tyr Ile Cys Thr Glu Gly Glu Asp Gln Ile Thr Val Trp Gly Phe His
                195                 200                 205

Ser Asp Asp Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
                260                 265                 270

Gly Thr Ile Val Tyr Gln Arg Gly Val Leu Leu Pro Gln Lys Val Trp
                275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
                420                 425                 430

Glu Leu His Asn Glu Ile Leu Glu Leu Asp Glu Lys Val Asp Asp Leu
    435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
                500                 505                 510

Ile Ala Ala Gly Thr Phe Asn Ala Gly Glu Phe Ser Leu Pro Thr Phe
                515                 520                 525

Asp Ser Leu Asn Ile Thr Ala His His His His His His
    530                 535                 540
```

-continued

```
<210> SEQ ID NO 106
<211> LENGTH: 553
<212> TYPE: PRT
<213> ORGANISM: Artificial Sequence
<220> FEATURE:
<223> OTHER INFORMATION: UFV180570

<400> SEQUENCE: 106

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Arg Thr
        50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu Asn Ile Arg Leu Ser Thr Gln Asn Val Ile Asp Ala Glu Lys
        130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
            195                 200                 205

Ser Asp Asp Lys Thr Gln Met Lys Asn Leu Tyr Gly Asp Ser Asn Pro
        210                 215                 220

Gln Gln Phe Thr Ser Ser Ala Asn Gly Val Thr Thr Ile Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
            275                 280                 285

Cys Ala Ser Gly Arg Ser Lys Val Ile Lys Gly Ser Leu Pro Leu Ile
        290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
            355                 360                 365
```

```
Gly Phe Glu Gly Met Ile Ala Gly Trp Ile Gly Tyr Thr Ser His Gly
    370             375             380

Ala His Gly Val Ala Val Ala Ala Asp Leu Lys Ser Thr Gln Glu Ala
385             390             395             400

Ile Asn Lys Ile Thr Lys Asn Leu Asn Ser Leu Ser Glu Leu Glu Val
            405             410             415

Lys Asn Leu Gln Arg Leu Ser Gly Ala Met Asp Glu Leu His Asn Glu
            420             425             430

Ile Leu Glu Leu Asp Glu Lys Val Asp Asp Leu Arg Ala Asp Thr Ile
            435             440             445

Ser Ser Gln Ile Glu Leu Arg Val Leu Leu Ser Asn Glu Gly Ile Ile
    450             455             460

Asn Ser Glu Asp Glu Ile Leu Leu Ala Leu Glu Arg Lys Leu Lys Lys
465             470             475             480

Met Leu Gly Pro Ser Ala Val Glu Ile Gly Asn Gly Cys Phe Glu Thr
            485             490             495

Lys His Lys Cys Asn Gln Thr Cys Leu Asp Arg Ile Ala Ala Gly Thr
            500             505             510

Phe Asn Ala Gly Glu Phe Ser Leu Pro Thr Phe Asp Ser Leu Asn Ile
            515             520             525

Thr Ala Ser Gly Ser Leu Val Pro Ser Gly Ser Leu Pro Glu Thr Gly
    530             535             540

Gly Gly Ser His His His His His His
545             550
```

<210> SEQ ID NO 107
<211> LENGTH: 540
<212> TYPE: PRT
<213> ORGANISM: Artificial Sequence
<220> FEATURE:
<223> OTHER INFORMATION: UFV190909

<400> SEQUENCE: 107

```
Met Lys Ala Ile Ile Val Leu Leu Met Val Val Thr Ser Asn Ala Asp
1               5               10              15

Arg Ile Cys Thr Gly Ile Thr Ser Ser Asn Ser Pro His Val Val Lys
            20              25              30

Thr Ala Thr Gln Gly Glu Val Asn Val Thr Gly Val Ile Pro Leu Thr
            35              40              45

Thr Thr Pro Thr Lys Ser His Phe Ala Asn Leu Lys Gly Thr Glu Thr
    50              55              60

Arg Gly Lys Leu Cys Pro Lys Cys Leu Asn Cys Thr Asp Leu Asp Val
65              70              75              80

Ala Leu Gly Arg Pro Lys Cys Thr Gly Lys Ile Pro Ser Ala Arg Val
            85              90              95

Ser Ile Leu His Glu Val Arg Pro Val Thr Ser Gly Cys Phe Pro Ile
            100             105             110

Met His Asp Arg Thr Lys Ile Arg Gln Leu Pro Asn Leu Leu Arg Gly
            115             120             125

Tyr Glu His Val Arg Leu Ser Thr His Asn Val Ile Asn Ala Glu Gly
    130             135             140

Ala Pro Gly Gly Pro Tyr Lys Ile Gly Thr Ser Gly Ser Cys Pro Asn
145             150             155             160

Ile Thr Asn Gly Asn Gly Phe Phe Ala Thr Met Ala Trp Ala Val Pro
            165             170             175
```

-continued

```
Asp Lys Asn Lys Thr Ala Thr Asn Pro Leu Thr Ile Glu Val Pro Tyr
            180                 185                 190

Val Cys Thr Glu Gly Glu Asp Gln Ile Thr Val Trp Gly Phe His Ser
            195                 200                 205

Asp Asn Glu Thr Gln Met Ala Lys Leu Tyr Gly Asp Ser Lys Pro Gln
    210                 215                 220

Lys Phe Thr Ser Ser Ala Asn Gly Val Thr Thr His Tyr Val Ser Gln
225                 230                 235                 240

Ile Gly Gly Phe Pro Asn Gln Thr Glu Asp Gly Gly Leu Pro Gln Ser
                245                 250                 255

Gly Arg Ile Val Val Asp Tyr Met Val Gln Lys Ser Gly Lys Thr Gly
            260                 265                 270

Thr Ile Thr Tyr Gln Arg Gly Ile Leu Leu Pro Gln Lys Val Trp Cys
            275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
            355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
            435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Glu Ile Gly Asn Gly
                485                 490                 495

Cys Phe Glu Thr Lys His Lys Cys Asn Gln Thr Cys Leu Asp Lys Ile
            500                 505                 510

Ala Ala Gly Thr Phe Asp Ala Gly Glu Phe Ser Leu Pro Thr Phe Asp
            515                 520                 525

Ser Leu Asn Ile Thr Ala His His His His His
    530                 535                 540
```

```
<210> SEQ ID NO 108
<211> LENGTH: 551
<212> TYPE: PRT
<213> ORGANISM: Artificial Sequence
<220> FEATURE:
<223> OTHER INFORMATION: UFV190521

<400> SEQUENCE: 108
```

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Val Arg Leu Ser Thr His Asn Val Ile Asn Ala Glu Gly
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Asp Lys Asn Lys Thr Ala Thr Asn Pro Leu Thr Ile Glu Val Pro Tyr
            180                 185                 190

Val Cys Thr Glu Gly Glu Asp Gln Ile Thr Val Trp Gly Phe His Ser
            195                 200                 205

Asp Asn Glu Thr Gln Met Ala Lys Leu Tyr Gly Asp Ser Lys Pro Gln
    210                 215                 220

Gln Phe Thr Ser Ser Ala Asn Gly Val Thr Thr Ile Tyr Val Ser Gln
225                 230                 235                 240

Ile Gly Gly Phe Pro Asn Gln Thr Glu Asp Gly Gly Leu Pro Gln Ser
                245                 250                 255

Gly Arg Ile Val Val Asp Tyr Met Val Gln Lys Ser Gly Lys Thr Gly
            260                 265                 270

Thr Ile Thr Tyr Gln Arg Gly Ile Leu Leu Pro Gln Lys Val Trp Cys
    275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
            325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
            355                 360                 365

Phe Leu Glu Gly Gly Trp Glu Gly Met Ile Ala Gly Trp Ile Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
            405                 410                 415

Glu Leu Glu Val Lys Asn Leu Gln Arg Leu Ser Gly Ala Met Asp Glu
```

-continued

```
                420                    425                       430

Leu His Asn Glu Ile Leu Glu Leu Asp Glu Lys Val Asp Asp Leu Arg
        435                    440                       445

Ala Asp Thr Ile Ser Ser Gln Ile Glu Leu Arg Val Leu Leu Ser Asn
        450                    455                       460

Glu Gly Ile Ile Asn Ser Glu Asp Glu Ile Leu Leu Ala Leu Glu Arg
465                          470                    475                480

Lys Leu Lys Lys Met Leu Gly Pro Ser Ala Val Glu Ile Gly Asn Gly
                485                    490                       495

Cys Phe Glu Thr Lys His Lys Cys Asn Gln Thr Cys Leu Asp Lys Ile
                500                    505                       510

Ala Ala Gly Thr Phe Asp Ala Gly Glu Phe Ser Leu Pro Thr Phe Asp
        515                    520                       525

Ser Leu Asn Ile Thr Ala Ser Gly Ser Leu Pro Glu Thr Gly Gly Gly
        530                    535                       540

Ser His His His His His His
545                    550
```

The invention claimed is:

1. An isolated mutant influenza hemagglutinin polypeptide comprising at least two mutations that increase thermal stability of the polypeptide relative to wild-type influenza hemagglutinin, wherein the mutations comprise substitution mutations at:

a. amino acid positions 227 and/or 238; and/or b. amino acid positions 384 and/or 476, wherein the amino acid position corresponds to the amino acid position of SEQ ID NO:1.

2. The isolated mutant influenza hemagglutinin polypeptide of claim 1, wherein a. amino acid position 227 is substituted with an amino acid selected from the group consisting of Q, N, F, I, and Y, and/or amino acid position 238 is substituted with an amino acid selected from the group consisting of N, Q, I, and F; and/or b. amino acid position 384 is substituted with an amino acid selected from the group consisting of W, F, N, Q, and I, and/or amino acid position 476 is substituted with an amino acid selected from the group consisting of W, F, Y, I, N, and Q.

3. The isolated mutant influenza hemagglutinin polypeptide of claim 2, wherein a. amino acid position 227 is substituted with a Q and amino acid position 238 is substituted with an I; and/or b. amino acid position 384 is substituted with an I and amino acid position 476 is substituted with an I.

4. The isolated mutant influenza hemagglutinin polypeptide of claim 1, further comprising one mutation in the polypeptide, wherein the mutation is a substitution at amino acid position 461 and the mutation increases thermal stability of the polypeptide relative to wild-type influenza hemagglutinin, wherein the amino acid position corresponds to the amino acid position in SEQ ID NO:1.

5. The isolated mutant influenza hemagglutinin polypeptide of claim 4, wherein amino acid position 461 is substituted with an amino acid selected from the group consisting of M, L, W, Y, and R.

6. The isolated mutant influenza hemagglutinin polypeptide of claim 5, wherein amino acid position 461 is substituted with an R.

7. The isolated mutant influenza hemagglutinin polypeptide of claim 3, wherein the mutant influenza hemagglutinin polypeptide comprises an amino acid sequence selected from SEQ ID NO:19, SEQ ID NO:35, SEQ ID NO:39, or SEQ ID NO:40.

8. The isolated mutant influenza hemagglutinin polypeptide of claim 6, wherein the mutant influenza hemagglutinin polypeptide comprises an amino acid sequence of SEQ ID NO:8 or SEQ ID NO: 108.

9. The isolated mutant influenza hemagglutinin polypeptide of claim 1, further comprising at least one additional glycan motif in a head domain of the polypeptide.

10. The isolated mutant influenza hemagglutinin polypeptide of claim 9, wherein the glycan motif comprises a substitution of an amino (N)-linked glycosylation motif in at least one amino acid position selected from the group consisting of:

a. 136 or 137, b. 141, and c. 151, wherein the amino acid position corresponds to the amino acid position of SEQ ID NO:1.

11. The isolated mutant influenza hemagglutinin polypeptide of claim 10, wherein the glycan motif comprises the substitution of the N-linked glycosylation motif at amino acid positions 136 and 141, 136 and 151, 137 and 141, 137 and 151, or 141 and 151.

12. The isolated mutant influenza hemagglutinin polypeptide of claim 11, wherein the glycan motif comprises the substitution of the N-linked glycosylation motif at amino acid positions 141 and 151.

13. The isolated mutant influenza hemagglutinin polypeptide of claim 10, wherein the mutant influenza hemagglutinin polypeptide comprises an amino acid sequence selected from SEQ ID NO:42, SEQ ID NO:43, SEQ ID NO:44, or SEQ ID NO:45.

14. The isolated mutant influenza hemagglutinin polypeptide of claim 1, further comprising a receptor binding site mutation in the polypeptide.

15. The isolated mutant influenza hemagglutinin polypeptide of claim 14, wherein the receptor binding site mutation comprises a substitution at an amino acid position selected from the group consisting of:

a. 175, b. 219, c. 257, and d. 258, wherein the amino acid position corresponds to the amino acid position of SEQ ID NO:1.

16. The isolated mutant influenza hemagglutinin polypeptide of claim 15, wherein a. 175 is substituted with an amino acid selected from the group consisting of F, W, and Y;

b. 219 is substituted with an amino acid selected from the group consisting of F, W, Y, R, and E;

c. 257 is substituted with an amino acid selected from the group consisting of E, D, V, and F; or d. 258 is substituted with an amino acid selected from the group consisting of E, D, V, and F.

17. The isolated mutant influenza hemagglutinin polypeptide of claim 16, wherein a. 175 is substituted with a W, b. 219 is substituted with an E, c. 257 is substituted with an E, or d. 258 is substituted with an E.

18. The isolated mutant influenza hemagglutinin polypeptide of claim 17, wherein the mutant influenza hemagglutinin polypeptide comprises an amino acid sequence selected from SEQ ID NO:50, SEQ ID NO:51, SEQ ID NO:55, or SEQ ID NO:61.

19. The isolated mutant influenza hemagglutinin polypeptide of claim 1, wherein the polypeptide further comprises an amino acid substitution at position 136, wherein the amino acid position corresponds to the amino acid position of SEQ ID NO:1.

20. The isolated mutant influenza hemagglutinin polypeptide of claim 1, further comprising a fusion peptide proximal region (FPPR) deletion mutation.

21. The isolated mutant influenza hemagglutinin polypeptide of claim 20, wherein the FPPR deletion mutation comprises a deletion of at least three to seven amino acid residues between amino acid position 369 and 382, wherein the amino acid position corresponds to the amino acid position of SEQ ID NO:1.

22. The isolated mutant influenza hemagglutinin polypeptide of claim 21, wherein the FPPR deletion mutation comprises a deletion selected from the group consisting of Δ372-376, Δ372-378, Δ373-377, Δ373-376, Δ374-379, Δ374-376, Δ376-380, and Δ377-381.

23. The isolated mutant influenza hemagglutinin polypeptide of claim 22, wherein the FPPR deletion mutation comprises a deletion selected from Δ372-376 or Δ376-380.

24. The isolated mutant influenza hemagglutinin polypeptide of claim 23, wherein the mutant influenza hemagglutinin polypeptide comprises an amino acid sequence selected from SEQ ID NO:62 or SEQ ID NO:68.

25. The isolated mutant influenza hemagglutinin polypeptide of claim 1, wherein the mutant hemagglutinin polypeptide comprises an amino acid sequence selected from SEQ ID NO:70, SEQ ID NO:81, SEQ ID NO:82, SEQ ID NO:83, SEQ ID NO:84, SEQ ID NO:91, SEQ ID NO:92, SEQ ID NO:93, SEQ ID NO:102, SEQ ID NO:104, or SEQ ID NO:106.

26. The isolated mutant influenza hemagglutinin polypeptide of claim 1, wherein the mutant influenza hemagglutinin polypeptide comprises a heterologous trimerization domain.

27. The isolated mutant influenza hemagglutinin polypeptide of claim 1, wherein the mutant influenza hemagglutinin polypeptide further comprises a carboxy (C)-terminal truncation starting at an amino acid position from amino acid position 532 to amino acid position 549, wherein the amino acid position corresponds to the amino acid position of SEQ ID NO:1.

28. The isolated mutant influenza hemagglutinin polypeptide of claim 27, wherein the C-terminal truncation starts at amino acid position 532, 534, 536, 539, 541, 543, 545, 547, or 549.

29. The isolated mutant influenza hemagglutinin polypeptide of claim 1, wherein the mutant influenza hemagglutinin polypeptide further comprises an amino acid substitution at a cleavage site at amino acid position 362, wherein the amino acid position corresponds to the amino acid position of SEQ ID NO:1.

30. The isolated mutant influenza hemagglutinin polypeptide of claim 29, wherein amino acid position 362 is substituted with a Q.

31. An isolated nucleic acid encoding a mutant influenza hemagglutinin polypeptide comprising at least two mutations that increase thermal stability of the polypeptide relative to wild-type influenza hemagglutinin, wherein the mutations are substitutions at:

a. amino acid positions 227 and/or 238; and/or b. amino acid positions 384 and/or 476;

wherein the amino acid position corresponds to the amino acid position of SEQ ID NO:1.

32. A vector comprising the isolated nucleic acid of claim 31.

33. A host cell comprising the vector of claim 32.

34. A pharmaceutical composition comprising the isolated mutant influenza hemagglutinin polypeptide of claim 1 and a pharmaceutically acceptable carrier.

35. A pharmaceutical composition comprising the isolated nucleic acid of claim 31.

36. A pharmaceutical composition comprising the vector of claim 32.

37. A method of inducing an immune response against an influenza virus in a subject in need thereof, the method comprising administering to the subject in need thereof the pharmaceutical composition of claim 34.

38. A method of producing an isolated mutant influenza hemagglutinin polypeptide, the method comprising culturing the host cell of claim 33 under conditions capable of producing the mutant influenza hemagglutinin polypeptide and recovering the mutant influenza hemagglutinin polypeptide from the cell or culture.

39. A method of producing the pharmaceutical composition of claim 34, the method comprising combining the isolated mutant influenza polypeptide with a pharmaceutically acceptable carrier.

\* \* \* \* \*